(12) United States Patent
Cameron

(10) Patent No.: US 9,458,192 B1
(45) Date of Patent: Oct. 4, 2016

(54) COVALENT GRANZYME B INHIBITORS

(71) Applicant: viDA Therapeutics Inc., Vancouver (CA)

(72) Inventor: Dale R. Cameron, Richmond (CA)

(73) Assignee: viDA Therapeutics Inc., Vancouver (CA)

( * ) Notice: Subject to any disclaimer, the term of this patent is extended or adjusted under 35 U.S.C. 154(b) by 0 days.

(21) Appl. No.: 14/815,717

(22) Filed: Jul. 31, 2015

Related U.S. Application Data

(60) Provisional application No. 62/032,465, filed on Aug. 1, 2014.

(51) Int. Cl.
  *C07K 5/097*   (2006.01)
  *A61K 38/06*   (2006.01)

(52) U.S. Cl.
  CPC ............. *C07K 5/0821* (2013.01); *A61K 38/06* (2013.01)

(58) Field of Classification Search
  None
  See application file for complete search history.

(56) References Cited

U.S. PATENT DOCUMENTS

| | | |
|---|---|---|
| 2003/0148511 A1 | 8/2003 | Ashton-Rickardt |
| 2005/0208000 A1 | 9/2005 | Bernstein |

FOREIGN PATENT DOCUMENTS

| | | |
|---|---|---|
| WO | 03/065987 A2 | 8/2003 |
| WO | 2007/101354 A1 | 9/2007 |
| WO | 2012/076985 A2 | 6/2012 |
| WO | 2014/153666 A1 | 10/2014 |

OTHER PUBLICATIONS

Willoughby, C.A., et al, "Discovery of potent, selective human granzyme B inhibitors that inhibit CTL mediated apoptosis," Bioorganic & Medicinal Chemistry Letters (2002), 12(16), 2197-2200.*

Buzza, M.S., et al., "Extracellular Matrix Remodeling by Human Granzyme B Via Cleavage of Vitronectin, Fibronectin, and Laminin," Journal of Biological Chemistry 280(25):23549-23558, Jun. 2005.

International Search Report and Written Opinion mailed Jul. 2, 2014, from International Application No. PCT/CA2014/050317, filed Mar. 28, 2014, 12 pages.

International Preliminary Report on Patentability mailed Sep. 29, 2015, from International Application No. PCT/CA2014/050317, filed Mar. 28, 2014, 7 pages.

International Search Report and Written Opinion mailed Jul. 3, 2014, from International Application No. PCT/CA2014/050318, filed Mar. 28, 2014, 8 pages.

International Preliminary Report on Patentability mailed Sep. 29, 2015, from International Application No. PCT/CA2014/050318, filed Mar. 28, 2014, 6 pages.

International Search Report and Written Opinion mailed Oct. 6, 2015, from International Application No. PCT/CA2015/050725, filed Jul. 31, 2015, 11 pages.

International Search Report and Written Opinion mailed Nov. 3, 2015, issued in International Application No. PCT/CA2015/050724, filed Jul. 31, 2015, 13 pages.

Kam, C.-M., et al., "Granzymes (Lymphocyte Serine Proteases): Characterization With Natural and Synthetic Substrates and Inhibitors," Biochimica et Biophysica Acta (BBA)—Protein Structure and Molecular Enzymology 1477(1-2):307-323, Mar. 2000.

Willoughby, C.A., "Discovery of Potent, Selective Human Granzyme B Inhibitors That Inhibit CTL Mediated Apoptosis," Bioorganic & Medicinal Chemistry Letters 12(16):2197-2200, Aug. 2002.

\* cited by examiner

*Primary Examiner* — Thomas S Heard
(74) *Attorney, Agent, or Firm* — Christensen O'Connor Johnson Kindness PLLC

(57) ABSTRACT

Covalent Granzyme B inhibitors, compositions that include the compounds, and methods for using the compounds. A method for treating cutaneous scleroderma, epidermolysis bullosa, radiation dermatitis, alopecia areata, and discoid lupus erythematosus are provided.

9 Claims, 3 Drawing Sheets

COVALENT GRANZYME B INHIBITORS

CROSS-REFERENCE TO RELATED APPLICATION

This application claims the benefit of U.S. Provisional Application No. 62/032,465, filed Aug. 1, 2014, which application is incorporated herein by reference in its entirety.

BACKGROUND OF THE INVENTION

Granzyme B is a pro-apoptotic serine protease found in the granules of cytotoxic lymphocytes (CTL) and natural killer (NK) cells. Granzyme B is released towards target cells, along with the pore-forming protein, perforin, resulting in its perforin-dependent internalization into the cytoplasm and subsequent induction of apoptosis (see, for e.g., Medema et al., *Eur. J. Immunol.* 27:3492-3498, 1997). However, during aging, inflammation and chronic disease, Granzyme B can also be expressed and secreted by other types of immune (e.g., mast cell, macrophage, neutrophil, and dendritic cells) or non-immune (keratinocyte, chondrocyte) cells and has been shown to possess extracellular matrix remodeling activity (Choy et al., *Arterioscler. Thromb. Vasc. Biol.* 24(12):2245-2250, 2004 and Buzza et al., *J. Biol. Chem.* 280:23549-23558, 2005).

Inhibitors of Granzyme B in humans have been limited to (a) relatively weak, nonspecific inhibitors such as isocoumarins (Odake et al., (1991), *Biochemistry*, 30(8), 2217-2227); (b) biological inhibitors such as serpinB9 (Sun et al., (1996), *J. Biol. Chem.*, 271(44), 27802-27809); (c) covalently coupled inhibitors such as aldehydes (Willoughby et al., (2002), *Bioorg. Med. Chem. Lett.*, 12(16), 2197), halomethyl ketones (Kam et al., (2000), *Biochim. Biophy. Acta*, 1477(1-2), 307-323), and phosphonates (Mahrus and Craik, (2005), *Chem. & Biol.*, 12, 567-77 and Kam et al., (2000)); and (d) tricyclic inhibitors (Willoughby et al., (2002)).

Nonspecific inhibitors (such as isocoumarins) are not sufficiently potent or specific to be effective treatments for Granzyme-B-related diseases, disorders, and conditions. Likewise, the use of biological inhibitors such as serpins is limited by the ability to deliver the inhibitor to the target mammal, the cost of manufacturing the biological agents, and other, off-target activities, such as inhibition of other serine proteases such as human neutrophil elastase (Dahlen et al., (1999), *Biochim. Biophys. Acta*, 1451(2-3), 233-41), Caspase-1 (Annaud et al., (1999), *Biochem. J., September 15*; 342 Pt3, 655-65; Krieg et al., (2001), *Mol. Endocrinol.*, 15(11), 1971-82; and Young et al., (2000), *J. Exp. Med.*, 191(9), 1535-1544); Caspase-4 and Caspase-8 (Annaud et al., (1999)).

The tricyclic inhibitors (Willoughby et al. (2001)) also suffer from synthetic complexity/high manufacturing cost due to the complex core and accompanying low water solubility.

Despite the advances in development of Granzyme B inhibitors, there exists a need for covalent compounds that inhibit Granzyme B. The present invention seeks to fulfill this need and provides further related advantages.

SUMMARY OF THE INVENTION

The present invention provides Granzyme B inhibitor compounds, compositions that include the compounds, and methods for using the compounds.

In one aspect of the invention, the invention provides covalent Granzyme B inhibitor compounds.

In one embodiment, the invention provides the compounds having Formula (I):

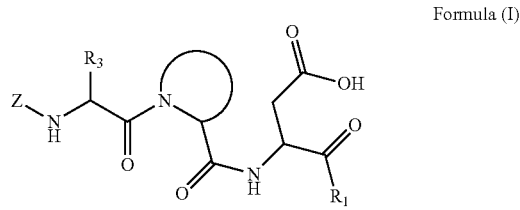

Formula (I)

its stereoisomers, tautomers, and pharmaceutically acceptable salts thereof, wherein:

$R_1$ is selected from
(a) hydrogen,
(b) —C(=O)NH$R_a$, wherein $R_a$ is alkyl or substituted alkyl, or aryl or substituted aryl,
(c) —C(=O)O$R_a$, wherein $R_a$ is hydrogen, alkyl or substituted alkyl, or aryl or substituted aryl, and
(d) —CH$_2$X, wherein X is a halogen;

$R_3$ is selected from
(a) hydrogen,
(b) $C_1$-$C_4$ alkyl optionally substituted with a carboxylic acid, carboxylate, or carboxylate $C_1$-$C_8$ ester group (—CO$_2$H, —CO$_2^-$, —CO$_2C_1$-$C_8$), an amide optionally substituted with an alkylheteroaryl group, or a heteroaryl group;

Z is an acyl group selected from
(a)

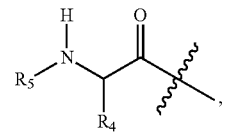

and
(b)

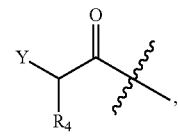

wherein Y is hydrogen or $C_1$-$C_4$ alkyl;
$R_4$ is selected from
(i) hydrogen,
(ii) $C_1$-$C_{12}$ alkyl,
(iii) $C_3$-$C_6$ cycloalkyl,
(iv) $C_6$-$C_{10}$ aryl,
(v) heterocyclyl,
(vi) $C_3$-$C_{10}$ heteroaryl,
(vii) aralkyl, and
$R_5$ is —C(=O)—$R_{10}$,
wherein $R_{10}$ is selected from
(i) $C_1$-$C_{12}$ alkyl optionally substituted with $C_6$-$C_{10}$ aryl, $C_1$-$C_{10}$ heteroaryl, amino, or carboxylic acid,
(ii) $C_1$-$C_{10}$ heteroalkyl optionally substituted with $C_1$-$C_6$ alkyl, carboxylic acid, or heterocyclyl,
(iii) $C_3$-$C_6$ cycloalkyl optionally substituted with $C_1$-$C_6$ alkyl, optionally substituted $C_6$-$C_{10}$ aryl, optionally substituted $C_3$-$C_{10}$ heteroaryl, amino, or carboxylic acid, (iv) $C_6$-$C_{10}$ aryl optionally substituted with $C_1$-$C_6$ alkyl, optionally substituted $C_6$-$C_{10}$ aryl, optionally substituted $C_3$-$C_{10}$ heteroaryl, amino, or carboxylic acid, (v) heterocyclyl,
(vi) $C_3$-$C_{10}$ heteroaryl,
(vii) aralkyl, and
(viii) heteroalkylaryl;
wherein

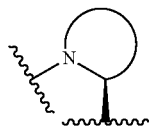

is selected from

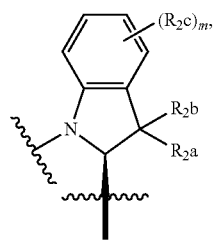

wherein
$R_2a$ and $R_2b$ are independently selected from hydrogen and $C_1$-$C_3$ alkyl, and
$R_2c$ at each occurrence is independently selected from
(a) hydrogen,
(b) halogen,
(c) $C_1$-$C_6$ alkyl,
(d) —$XR_{11}$, wherein X is selected from O, C(=O), S, S=O, or S(=O)$_2$,
(e) —C(=O)N($R_{12}$)($R_{13}$),
(f) —N($R_{11}$) ($R_{12}$)($R_{13}$),
(g) —N—C(=O)—$R_{11}$, and
(h) —N—C(=O)O—$R_{11}$,
wherein $R_{11}$, $R_{12}$, and $R_{13}$ are independently selected from the group consisting of hydrogen, $C_1$-$C_6$ alkyl, $C_1$-$C_6$ heteroalkyl, $C_2$-$C_6$ alkenyl, $C_6$-$C_{10}$ aryl, aralkyl, and $C_3$-$C_{10}$ heteroaryl; and
m is 1, 2, 3, or 4;

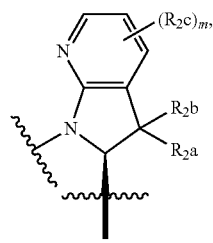

wherein
$R_2a$ and $R_2b$ are independently selected from hydrogen and C1-C6 alkyl; and
$R_2c$ at each occurrence is independently selected from
(a) hydrogen,
(b) halogen,
(c) $C_1$-$C_6$ alkyl,
(d) —$XR_{11}$, wherein X is selected from O, C(=O), S, S=O, or S(=O)$_2$,
(e) —C(=O)N($R_{12}$)($R_{13}$),
(f) —N($R_{11}$) ($R_{12}$)($R_{13}$),
(g) —N—C(=O)—$R_{11}$, and
(h) —N—C(=O)O—$R_{11}$,
wherein $R_{11}$, $R_{12}$, and $R_{13}$ are independently selected from the group consisting of hydrogen, $C_1$-$C_6$ alkyl, $C_1$-$C_6$ heteroalkyl, $C_2$-$C_6$ alkenyl, $C_6$-$C_{10}$ aryl, aralkyl, and $C_3$-$C_{10}$ heteroaryl;
m is 1, 2, or 3;

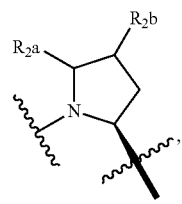

wherein $R_2a$ and $R_2b$ are independently selected from hydrogen, C1-C6 alkyl, C3-C6 cycloalkyl, substituted and unsubstituted aryl, substituted and unsubstituted aralkyl, hydroxy, C1-C6 alkoxy, aryloxy, aralkoxy, alkylthio, arylthio, arylsulfonyl, arylsulfinyl, substituted and unsubstituted —O(C=O)-aryl, substituted and unsubstituted —O(C=O)-aralkyl, and substituted and unsubstituted —O(C=O)—C1-C6 alkyl;

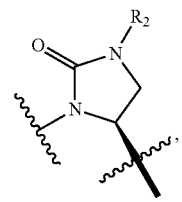

wherein $R_2$ is selected from hydrogen, C1-C6 alkyl, and C3-C6 cycloalkyl; and

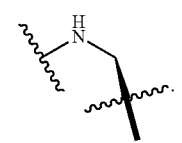

In another embodiment, the invention provides compounds having Formula (II):

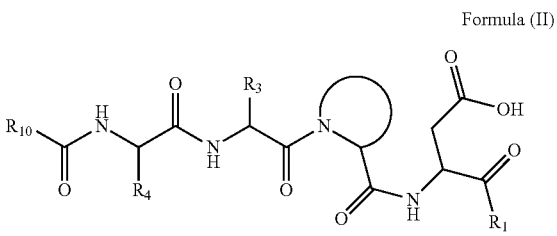

Formula (II)

its stereoisomers, tautomers, and pharmaceutically acceptable salts thereof, wherein $R_1$, $R_3$, $R_4$, and $R_{10}$ are as above for Formula (I).

In another aspect, the invention provides pharmaceutical compositions comprising a Granzyme B inhibitor compound of the invention and a pharmaceutically acceptable carrier.

In a further aspect of the invention, a method for inhibiting Granzyme B is provided. In one embodiment, the method comprises administering an effective amount of a Granzyme B inhibitor compound of the invention or a pharmaceutical composition of the invention to a subject in need thereof.

In a further aspect of the invention, methods for treating a disease, disorder, or condition treatable by inhibiting Granzyme B is provided. In one embodiment, the method comprises administering a therapeutically effective amount of a Granzyme B inhibitor compound of the invention or a pharmaceutical composition of the invention to a subject in need thereof. Representative routes of administration include topical administration, oral administration, and administration by injection.

In one embodiment, the invention provides a method for treating discoid lupus erythematosus (DLE) comprising administering a therapeutically effective amount of a Granzyme B inhibitor compound of the invention or a pharmaceutical composition of the invention to a subject in need thereof. In certain embodiments, the Granzyme B inhibitor compound of the invention or pharmaceutical composition is administered topically.

Cosmetic compositions comprising a Granzyme B inhibitor compound of the invention and a cosmetically acceptable carrier are also provided, as are methods for using the compositions to treat, reduce, and/or inhibit the appearance of ageing in the skin.

DETAILED DESCRIPTION OF THE INVENTION

Figure 1:
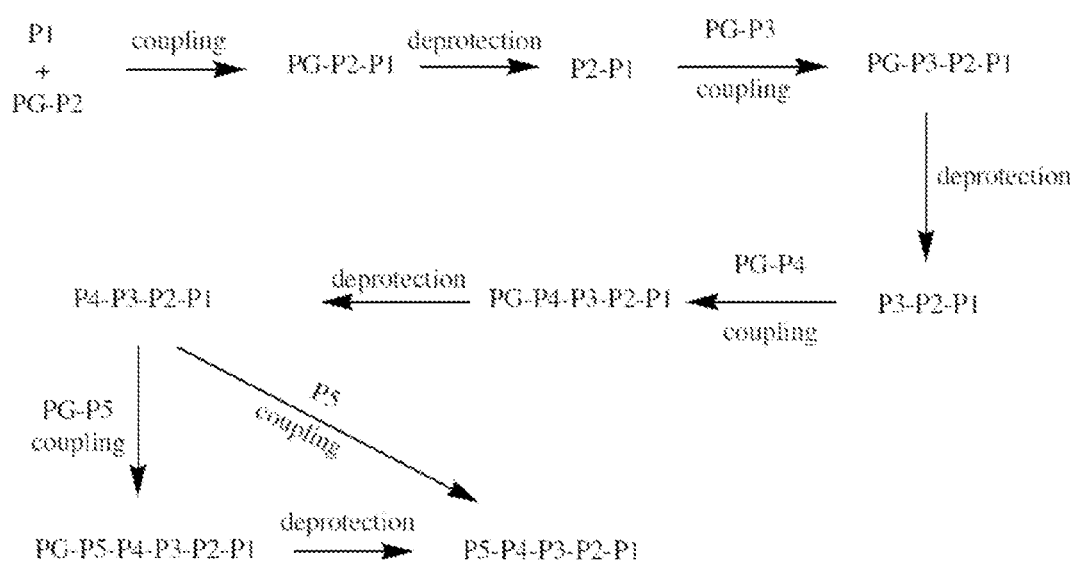
FIG. 1 is a schematic illustration of a representative synthetic pathway for the preparation of representative compounds of the invention P5-P4-P3-P2-P1 starting from P1.

The present invention provides covalent Granzyme B inhibitor compounds, compositions that include the compounds, and methods for using the compounds. The compounds of the invention effectively inhibit Granzyme B.

As used herein, the term "covalent Granzyme B inhibitor compounds" or "covalent inhibitor compound" refers to a Granzyme B inhibitor compound that covalently binds to Granzyme B. In certain embodiments, the covalent binding is reversible. In certain embodiments, the covalent binding is irreversible.

The compounds of the invention include a reactive functional group that is effective to covalently couple the compound to a Granzyme B active site. In certain embodiments, the reactive functional group is an electrophilic serine trap such as an aldehyde, keto-ester, keto-benzothiazole, or keto-oxadiazole. Suitable reactive functional groups are described in Willoughby et al., *Bioorg. Med. Chem. Lett.* 12 (2002) 2197-2200, expressly incorporated herein by reference in its entirety. Other suitable reactive functional groups include trifluoromethyl ketone, pentafluoroethylketone, keto-benzimidazole, keto-benzothiazole, and keto-benzoxazole groups. Representative reactive functional groups are described below.

The compounds of the invention can be used as diagnostics (e.g., irreversible covalent inhibitor compounds such as chloromethylketones) and can be used as probes of active Granzyme B or as active site blocking agents.

In one aspect of the invention, the invention provides covalent Granzyme B inhibitor compounds.

In one embodiment, the invention provides the compounds having Formula (I):

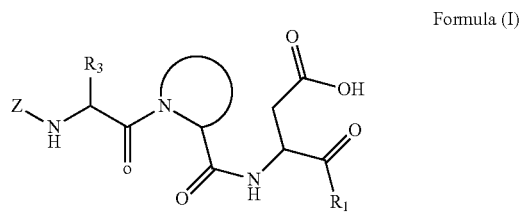

Formula (I)

its stereoisomers, tautomers, and pharmaceutically acceptable salts thereof, wherein:

$R_1$ is selected from
(a) hydrogen,
(b) —C(=O)NHR$_a$, wherein R$_a$ is alkyl or substituted alkyl (e.g., C1-C6 alkyl), or aryl or substituted aryl (e.g., CH$_2$C$_6$H$_5$),
(c) —C(=O)OR$_a$, wherein R$_a$ is hydrogen, alkyl or substituted alkyl (e.g., C1-C6 alkyl) aryl or substituted aryl (e.g., CH$_2$C$_6$H$_5$), and
(d) —CH$_2$X, wherein X is a halogen (e.g., fluoro, chloro, bromo, iodo); $R_3$ is selected from
(a) hydrogen,
(b) $C_1$-$C_4$ alkyl optionally substituted with a carboxylic acid, carboxylate, or carboxylate $C_1$-$C_8$ ester group (—CO$_2$H, —CO$_2^-$, —C(=O)OC$_1$-$C_8$), an amide optionally substituted with an alkylheteroaryl group, or a heteroaryl group;

Z is an acyl group selected from
(a)

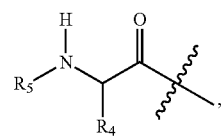

and
(b)

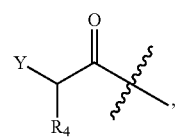

wherein Y is hydrogen or $C_1$-$C_4$ alkyl;
$R_4$ is selected from
(i) hydrogen,
(ii) $C_1$-$C_{12}$ alkyl,
(iii) $C_3$-$C_6$ cycloalkyl, (iv) $C_6$-$C_{10}$ aryl,
(v) heterocyclyl,
(vi) $C_3$-$C_{10}$ heteroaryl,
(vii) aralkyl, and $R_5$ is —C(=O)—$R_{10}$, wherein $R_{10}$ is selected from (i) $C_1$-$C_{12}$ alkyl optionally substituted with $C_6$-$C_{10}$ aryl, $C_1$-$C_{10}$ heteroaryl, amino, or carboxylic acid, (ii) $C_1$-$C_{10}$ heteroalkyl optionally substituted with $C_1$-$C_6$ alkyl, carboxylic acid, or heterocyclyl, (iii) $C_3$-$C_6$ cycloalkyl optionally substituted with $C_1$-$C_6$ alkyl, optionally substituted $C_6$-$C_{10}$ aryl, optionally substituted $C_3$-$C_{10}$ heteroaryl, amino, or carboxylic acid, (iv) $C_6$-$C_{10}$ aryl optionally substituted with $C_1$-$C_6$ alkyl, optionally substituted $C_6$-$C_{10}$ aryl, optionally substituted $C_3$-$C_{10}$ heteroaryl, amino, or carboxylic acid, (v) heterocyclyl,
(vi) $C_3$-$C_{10}$ heteroaryl,
(vii) aralkyl, and
(viii) heteroalkylaryl;

wherein

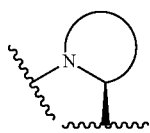

is selected from

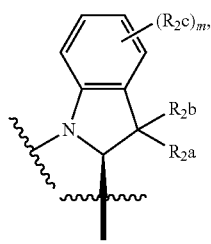

wherein $R_2a$ and $R_2b$ are independently selected from hydrogen and $C_1$-$C_3$ alkyl, and $R_2c$ at each occurrence is independently selected from
(a) hydrogen,
(b) halogen,
(c) $C_1$-$C_6$ alkyl,
(d) —$XR_{11}$, wherein X is selected from O, C(=O), S, S=O, or S(=O)$_2$,
(e) —C(=O)N($R_{12}$)($R_{13}$),
(f) —N($R_{11}$)($R_{12}$)($R_{13}$),
(g) —N—C(=O)—$R_{11}$, and
(h) —N—C(=O)O—$R_{11}$, wherein $R_{11}$, $R_{12}$, and $R_{13}$ are independently selected from the group consisting of hydrogen, $C_1$-$C_6$ alkyl, $C_1$-$C_6$ heteroalkyl, $C_2$-$C_6$ alkenyl, $C_6$-$C_{10}$ aryl, aralkyl, and $C_3$-$C_{10}$ heteroaryl; and m is 1, 2, 3, or 4;

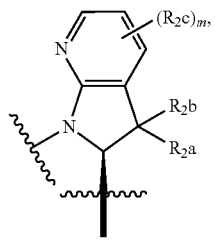

wherein $R_2a$ and $R_2b$ are independently selected from hydrogen and $C_1$-$C_3$ alkyl, and $R_2c$ at each occurrence is independently selected from
(a) hydrogen,
(b) halogen,
(c) $C_1$-$C_6$ alkyl,
(d) —$XR_{11}$, wherein X is selected from O, C(=O), S, S=O, or S(=O)$_2$,
(e) —C(=O)N($R_{12}$)($R_{13}$),
(f) —N($R_{11}$)($R_{12}$)($R_{13}$),
(g) —N—C(=O)—$R_{11}$, and
(h) —N—C(=O)O—$R_{11}$, wherein $R_{11}$, $R_{12}$, and $R_{13}$ are independently selected from the group consisting of hydrogen, $C_1$-$C_6$ alkyl, $C_1$-$C_6$ heteroalkyl, $C_2$-$C_6$ alkenyl, $C_6$-$C_{10}$ aryl, aralkyl, and $C_3$-$C_{10}$ heteroaryl; and m is 1, 2, or 3;

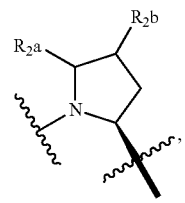

wherein $R_2a$ and $R_2b$ are independently selected from hydrogen, C1-C6 alkyl, C3-C6 cycloalkyl, substituted and unsubstituted aryl, substituted and unsubstituted aralkyl, hydroxy, C1-C6 alkoxy, aryloxy, aralkoxy, alkylthio, arylthio, arylsulfonyl, arylsulfinyl, substituted and unsubstituted —O(C=O)-aryl, substituted and unsubstituted —O(C=O)-aralkyl, and substituted and unsubstituted —O(C=O)—C1-C6 alkyl;

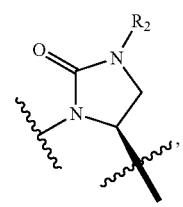

wherein $R_2$ is selected from hydrogen, C1-C6 alkyl, and C3-C6 cycloalkyl; and

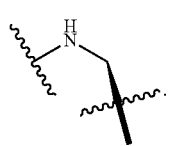

In another embodiment, the invention provides compounds having Formula (II):

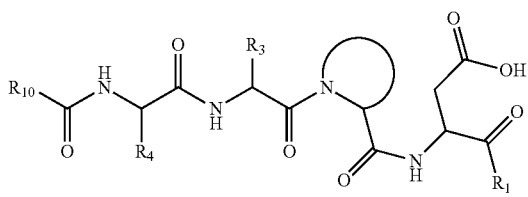

Formula (II)

its stereoisomers, tautomers, and pharmaceutically acceptable salts thereof, wherein $R_1$, $R_3$, $R_4$, and $R_{10}$ are as above for Formula (I).

In further embodiments, the invention provides compounds having Formulae (I) and (II), their stereoisomers, tautomers, and pharmaceutically acceptable salts thereof, wherein $R_4$ is selected from
(i) hydrogen,
(ii) $C_1$-$C_{12}$ alkyl,
(iii) $C_3$-$C_6$ cycloalkyl,
(iv) $C_6$-$C_{10}$ aryl,
(v) $C_3$-$C_{10}$ heteroaryl; and $R_5$ is —C(=O)—$R_{10}$, wherein $R_{10}$ is selected from
(i) $C_1$-$C_{12}$ alkyl optionally substituted with $C_6$-$C_{10}$ aryl, $C_1$-$C_{10}$ heteroaryl, amino, or carboxylic acid,
(ii) $C_1$-$C_{10}$ heteroalkyl optionally substituted with $C_1$-$C_6$ alkyl or carboxylic acid,
(iii) $C_3$-$C_6$ cycloalkyl optionally substituted with $C_1$-$C_6$ alkyl, optionally substituted $C_6$-$C_{10}$ aryl, optionally substituted $C_3$-$C_{10}$ heteroaryl, amino, or carboxylic acid,
(iv) $C_6$-$C_{10}$ aryl optionally substituted with $C_1$-$C_6$ alkyl, optionally substituted $C_6$-$C_{10}$ aryl, optionally substituted $C_3$-$C_{10}$ heteroaryl, amino, or carboxylic acid, and
(v) $C_3$-$C_{10}$ heteroaryl.

In certain embodiments, $R_{10}$, when defined as $C_1$-$C_{12}$ alkyl substituted with a carboxylic acid or carboxylate group, is:
—$(CH_2)_n$—$CO_2H$, where n is 2, 3, 4, 5, or 6;
optionally wherein one or more single methylene carbons are substituted with a fluoro, hydroxy, amino, $C_1$-$C_3$ alkyl (e.g., methyl), or $C_6$-$C_{10}$ aryl group;
optionally wherein one or more single methylene carbons are substituted with two fluoro (e.g., difluoro, perfluoro) or $C_1$-$C_3$ alkyl (e.g., gem-dimethyl) groups;
optionally wherein one or more single methylene carbons are substituted with two alkyl groups that taken together with the carbon to which they are attached form a 3-, 4-, 5-, or 6-membered carbocyclic ring (e.g., spiro groups such as cyclopropyl, cyclobutyl, cyclopentyl, and cyclohexyl); and
optionally wherein adjacent carbon atoms from an unsaturated carbon-carbon bond (e.g., alkenyl such as —CH=CH—) or taken form a benzene ring (e.g., 1,2-, 1,3-, and 1,4-phenylene); or wherein $R_{10}$, when defined as $C_3$-$C_6$ cycloalkyl substituted with a carboxylic acid or carboxylate group, is:

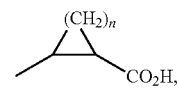

wherein n is 1, 2, 3, or 4; and optionally, for n=3 or 4, wherein adjacent carbon atoms from an unsaturated carbon-carbon bond (e.g., cyclopentenyl or cyclohexenyl).

In certain embodiments, the invention provides compounds having Formulae (I) or (II), their stereoisomers, tautomers, and pharmaceutically acceptable salts thereof, wherein:

$R_4$ is $C_1$-$C_8$ alkyl or $C_3$-$C_6$ cycloalkyl; and
$R_{10}$ is selected from
(a) $C_1$-$C_3$ alkyl substituted with $C_6$-$C_{10}$ aryl (e.g., phenyl) or $C_1$-$C_{10}$ heteroaryl (e.g., triazolyl or tetrazolyl); and
(b) —$(CH_2)_n$—$CO_2H$, where n is 2, 3, 4, 5, or 6.

For the compounds of Formulae (I) and (II), in certain embodiments, $R_1$ is a a group that imparts increased electrophilic character to the adjacent keto group and activates the keto group toward nucleophilic attack (e.g., aminoacids in the Granzyme B active site). In certain embodiments, $R_1$ is —$CH_2Cl$ and the reactive functional group is a a chloromethylketone (i.e., —C(=O)$CH_2Cl$). In other embodiments, $R_1$ is hydrogen and the reactive functional group is an aldehyde (i.e., —CHO).

For the compounds of Formulae (I) or (II), representative substituents $R_3$ include the following:

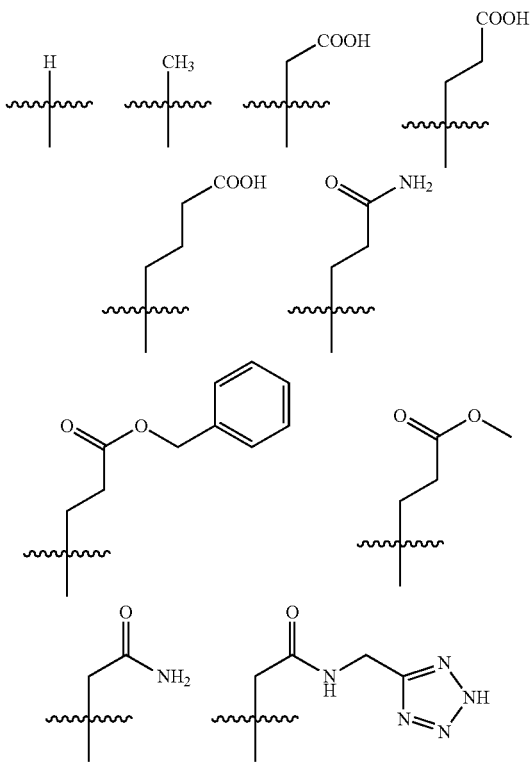

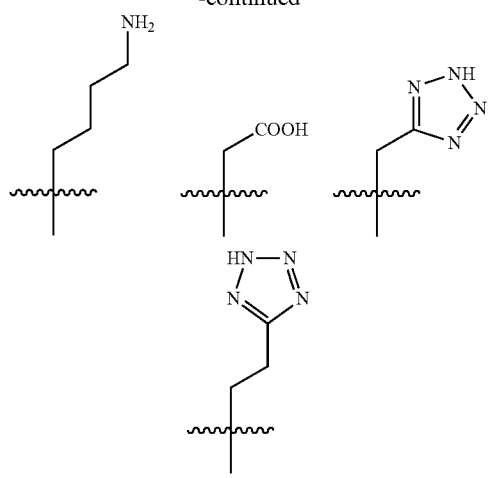
For the compounds of Formulae (I) or (II), representative substituents R$_4$ include the following:
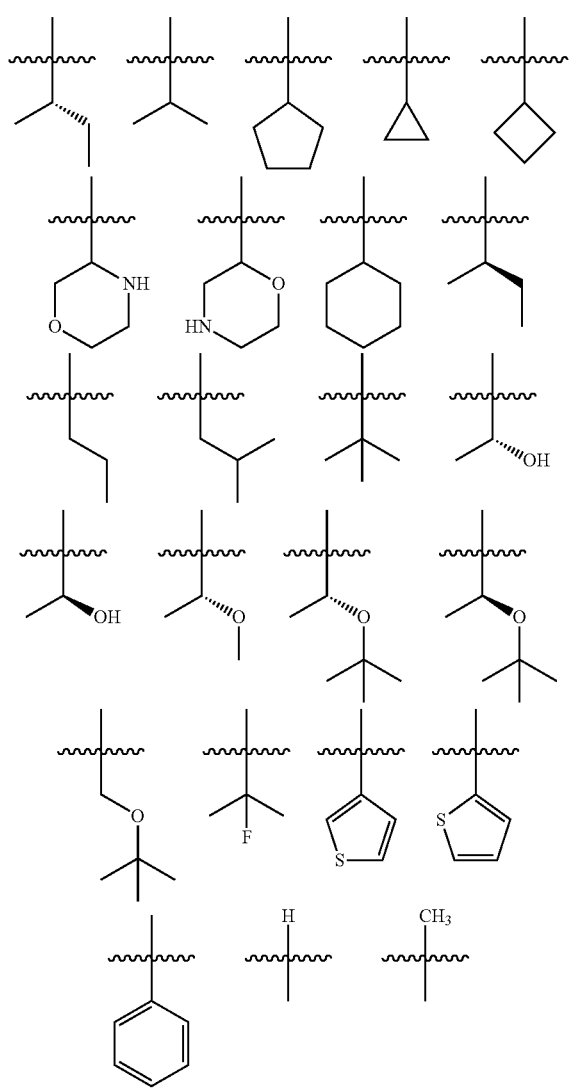
For the compounds of Formulae (I) or (II), representative substituents R$_5$ include the following:
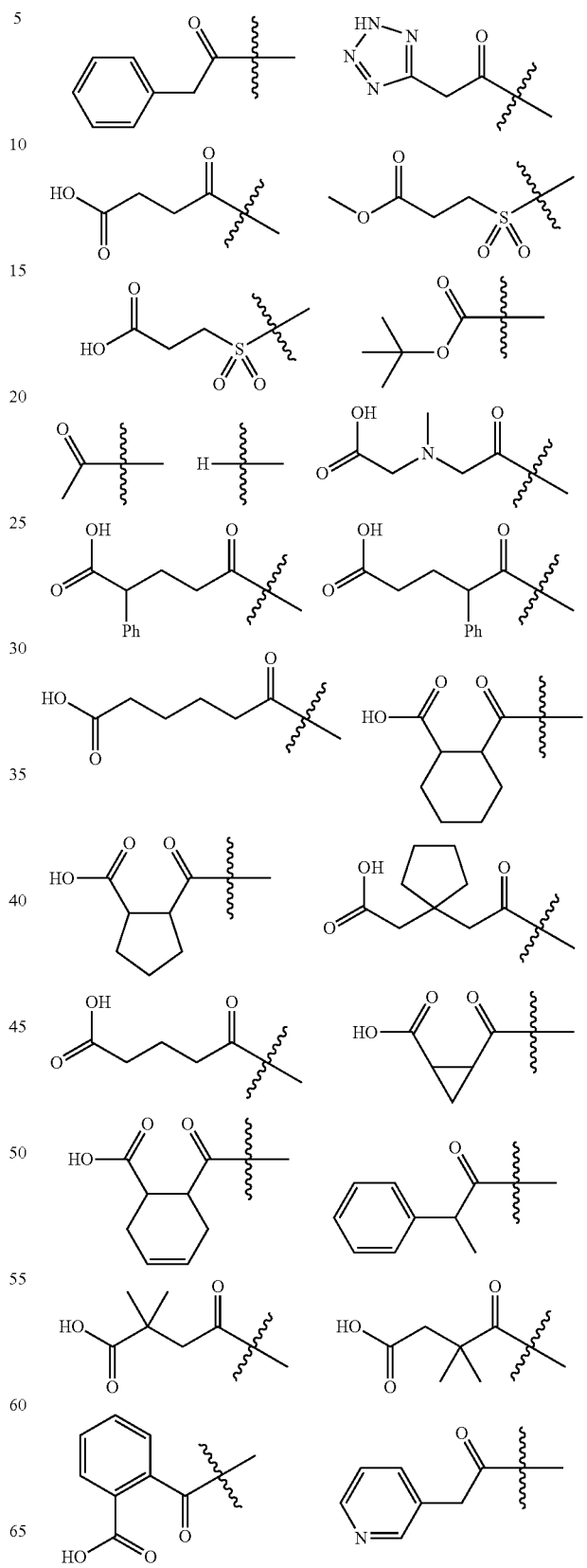

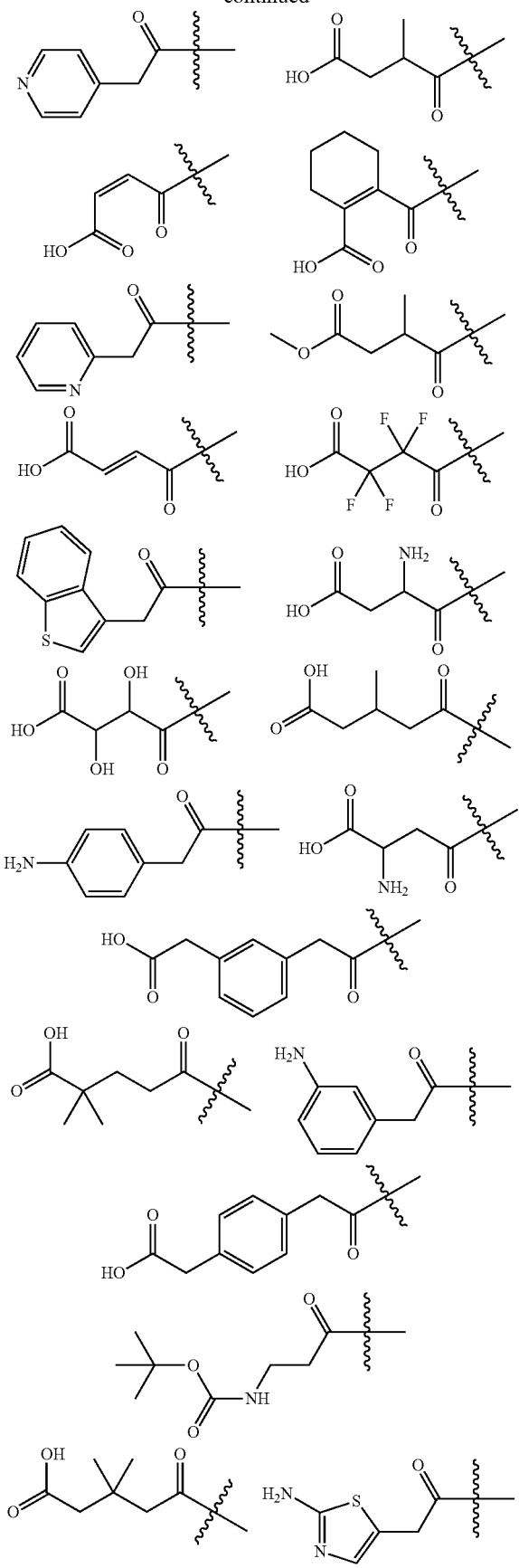
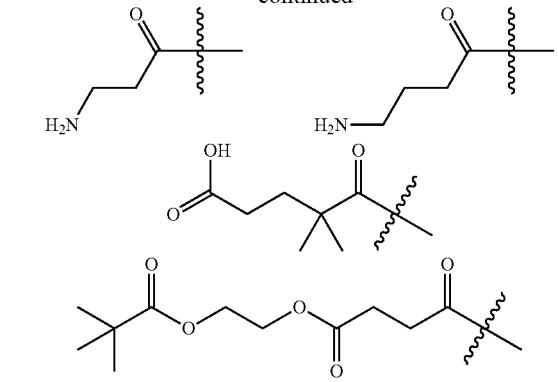

Each of the inhibitor compounds of the invention contain asymmetric carbon centers and give rise to stereoisomers (i.e., optical isomers such as diastereomers and enantiomers). It will be appreciated that the present invention includes such diastereomers as well as their racemic and resolved enantiomerically pure forms. It will also be appreciated that in certain configurations, the relative stereochemistry of certain groups may be depicted as "cis" or "trans" when absolute stereochemistry is not shown.

Some of the compounds described herein contain olefinic double bonds, and unless specified otherwise, are meant to include both E and Z geometric isomers.

Certain of the compounds of the invention may exist in one or more tautomeric forms (e.g., acid or basic forms depending on pH environment). It will be appreciated that the compounds of the invention include their tautomeric forms (i.e., tautomers).

When the compounds of the present invention are basic, salts may be prepared from pharmaceutically acceptable non-toxic acids, including inorganic and organic acids. Examples of such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids.

The invention is described using the following definitions unless otherwise indicated.

As used herein, the term "alkyl" refers to a saturated or unsaturated, branched, straight-chain or cyclic monovalent hydrocarbon group derived by the removal of one hydrogen atom from a single carbon atom of a parent alkane, alkene, or alkyne. Representative alkyl groups include methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl(allyl), cycloprop-1-en-1-yl; cycloprop-2-en-1-yl, prop-1-yn-1-yl, and prop-2-yn-1-yl; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, and but-3-yn-1-yl; and the like. Where a specific level of saturation is intended, the expressions "alkanyl," "alkenyl," and "alkynyl" are used. Alkyl groups include cycloalkyl groups. The term "cycloalkyl" refers to mono-, bi-, and tricyclic alkyl groups having the indicated number of carbon atoms. Representative cycloalkyl groups include cyclopropyl, cyclopentyl, cycloheptyl, adamantyl, cyclododecylmethyl, and 2-ethyl-1-bicyclo[4.4.0]decyl groups. The alkyl group may be unsubstituted or substituted as described below.

"Alkanyl" refers to a saturated branched, straight-chain, or cyclic alkyl group. Representative alkanyl groups include methanyl; ethanyl; propanyls such as propan-1-yl, propan-2-yl(isopropyl), and cyclopropan-1-yl; butanyls such as butan-1-yl, butan-2-yl(sec-butyl), 2-methyl-propan-1-yl (isobutyl), 2-methyl-propan-2-yl(t-butyl), and cyclobutan-1-yl; and the like. The alkanyl group may be substituted or unsubstituted. Representative alkanyl group substituents include —$R_{14}$, —$OR_{14}$, —$SR_{14}$, —$NR_{14}(R_{15})$,
—X, —$CX_3$, —CN, —$NO_2$,
—$C(=O)R_{14}$, —$C(=O)OR_{14}$, —$C(=O)NR_{14}(R_{15})$, —$C(=O)SR_{14}$,
—$C(=NR_{14})R_{14}$, —$C(=NR_{14})OR_{14}$, —$C(=NR_{14})NR_{14}(R_{15})$, —$C(=NR_{14})SR_{14}$,
—$C(=S)R_{14}$, —$C(=S)OR_{14}$, —$C(=S)NR_{14}(R_{15})$, —$C(=S)SR_{14}$,
—$NR_{14}C(=O)NR_{14}(R_{15})$, —$NR_{14}(=NR_{14})NR_{14}(R_{15})$, —$NR_{14}C(=S)NR_{14}(R_{15})$,
—$S(=O)_2R_{14}$, —$S(=O)_2OR_{14}$, —$S(=O)_2NR_{14}(R_{15})$,
—$OC(=O)R_{14}$, —$OC(=O)OR_{14}$, —$OC(=O)NR_{14}(R_{15})$, —$OC(=O)SR_{14}$,
—$OS(=O)_2OR_{14}$, —$OS(=O)_2NR_{14}(R_{15})$, and
—$OP(=O)_2(OR_{14})$, wherein each X is independently a halogen; and $R_{14}$ and $R_{15}$ are independently hydrogen, C1-C6 alkyl, C6-C14 aryl, arylalkyl, C3-C10 heteroaryl, and heteroarylalkyl, as defined herein.

In certain embodiments, two hydrogen atoms on a single carbon atom can be replaced with =O, =$NR_{12}$, or =S.

"Alkenyl" refers to an unsaturated branched, straight-chain, cyclic alkyl group, or combinations thereof having at least one carbon-carbon double bond derived by the removal of one hydrogen atom from a single carbon atom of a parent alkene. The group may be in either the cis or trans conformation about the double bond(s). Representative alkenyl groups include ethenyl; propenyls such as prop-1-en-1-yl, prop-1-en-2-yl, prop-2-en-1-yl(allyl), prop-2-en-2-yl, and cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, but-2-en-2-yl, buta-1,3-dien-1-yl, buta-1,3-dien-2-yl, cyclobut-1-en-1-yl, cyclobut-1-en-3-yl, and cyclobuta-1,3-dien-1-yl; and the like. The alkenyl group may be substituted or unsubstituted. Representative alkenyl group substituents include —$R_{14}$,
—X, —$CX_3$, —CN,
—$C(=O)R_{14}$, —$C(=O)OR_{14}$, —$C(=O)NR_{14}(R_{15})$, —$C(=O)SR_{14}$,
—$C(=NR_{14})R_{14}$, —$C(=NR_{14})OR_{14}$, —$C(=NR_{14})NR_{14}(R_{15})$, —$C(=NR_{14})SR_{14}$,
—$C(=S)R_{14}$, —$C(=S)OR_{14}$, —$C(=S)NR_{14}(R_{15})$, —$C(=S)SR_{14}$, wherein each X is independently a halogen; and $R_{14}$ and $R_{15}$ are independently hydrogen, C1-C6 alkyl, C6-C14 aryl, arylalkyl, C3-C10 heteroaryl, and heteroarylalkyl, as defined herein.

"Alkynyl" refers to an unsaturated branched, straight-chain, or cyclic alkyl group having at least one carbon-carbon triple bond derived by the removal of one hydrogen atom from a single carbon atom of a parent alkyne. Representative alkynyl groups include ethynyl; propynyls such as prop-1-yn-1-yl and prop-2-yn-1-yl; butynyls such as but-1-yn-1-yl, but-1-yn-3-yl, and but-3-yn-1-yl; and the like. The alkynyl group may be substituted or unsubstituted. Representative alkynyl group substituents include those as described above for alkenyl groups.

The term "haloalkyl" refers to an alkyl group as defined above having the one or more hydrogen atoms replaced by a halogen atom. Representative haloalkyl groups include halomethyl groups such as chloromethyl, fluoromethyl, and trifluoromethyl groups; and haloethyl groups such as chloroethyl, fluoroethyl, and perfluoroethyl groups. The term "heteroalkyl" refers to an alkyl group having the indicated number of carbon atoms and where one or more of the carbon atoms is replaced with a heteroatom selected from O, N, or S. Where a specific level of saturation is intended, the expressions "heteroalkanyl," "heteroalkenyl," and "heteroalkynyl" are used. Representative heteroalkyl groups include ether, amine, and thioether groups. Heteroalkyl groups include heterocyclyl groups. The term "heterocyclyl" refers to a 5- to 10-membered non-aromatic mono- or bicyclic ring containing 1-4 heteroatoms selected from O, S, and N. Representative heterocyclyl groups include pyrrolidinyl, piperidinyl, piperazinyl, tetrahydrofuranyl, tetrahydropuranyl, and morpholinyl groups. The heteroalkyl group may be substituted or unsubstituted. Representative heteroalkyl substituents include —$R_{14}$, —$OR_{14}$, —$SR_{14}$, —$NR_{14}(R_{15})$,
—X, —$CX_3$, —CN, —$NO_2$,
—$C(=O)R_{14}$, —$C(=O)OR_{14}$, —$C(=O)NR_{14}(R_{15})$, —$C(=O)SR_{14}$,
—$C(=NR_{14})R_{14}$, —$C(=NR_{14})OR_{14}$, —$C(=NR_{14})NR_{14}(R_{15})$, —$C(=NR_{14})SR_{14}$,
—$C(=S)R_{14}$, —$C(=S)OR_{14}$, —$C(=S)NR_{14}(R_{15})$, —$C(=S)SR_{14}$,
—$NR_{14}C(=O)NR_{14}(R_{15})$, —$NR_{14}(=NR_{14})NR_{14}(R_{15})$, —$NR_{14}C(=S)NR_{14}(R_{15})$,
—$S(=O)_2R_{14}$, —$S(=O)_2OR_{14}$, —$S(=O)_2NR_{14}(R_{15})$,
—$OC(=O)R_{14}$, —$OC(=O)OR_{14}$, —$OC(=O)NR_{14}(R_{15})$, —$OC(=O)SR_{14}$,
—$OS(=O)_2OR_{14}$, —$OS(=O)_2NR_{14}(R_{15})$, and
—$OP(=O)_2(OR_{14})$, wherein each X is independently a halogen; and $R_{14}$ and $R_{15}$ are independently hydrogen, C1-C6 alkyl, C6-C14 aryl, arylalkyl, C3-C10 heteroaryl, and heteroarylalkyl, as defined herein.

In certain embodiments, two hydrogen atoms on a single carbon atom can be replaced with =O, =$NR_{12}$, or =S.

The term "alkoxy" refers to an alkyl group as described herein bonded to an oxygen atom. Representative C1-C3 alkoxy groups include methoxy, ethoxy, propoxy, and isopropoxy groups.

The term "alkylamino" refers an alkyl group as described herein bonded to a nitrogen atom. The term "alkylamino" includes monoalkyl- and dialkylaminos groups. Representative C1-C6 alkylamino groups include methylamino, dimethylamino, ethylamino, methylethylamino, diethylamino, propylamino, and isopropylamino groups.

The term "alkylthio" refers an alkyl group as described herein bonded to a sulfur atom. Representative C1-C6 alkylthio groups include methylthio, propylthio, and isopropylthio groups.

The term "aryl" refers to a monovalent aromatic hydrocarbon group derived by the removal of one hydrogen atom from a single carbon atom of a parent aromatic ring system. Suitable aryl groups include groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, the aryl group is a C5-C14 aryl group. In other embodiments, the aryl group is a C5-C10 aryl group. The number of carbon atoms specified refers to the number of carbon atoms in the aromatic ring system. Representative aryl groups are phenyl, naphthyl, and cyclopentadienyl. The aryl group may be substituted or unsubstituted. Representative aryl group substituents include —$R_{14}$, —$OR_{14}$, —$SR_{14}$, —$NR_{14}(R_{15})$,
—X, —$CX_3$, —CN, —$NO_2$,
—$C(=O)R_{14}$, —$C(=O)OR_{14}$, —$C(=O)NR_{14}(R_{15})$, —$C(=O)SR_{14}$,
—$C(=NR_{14})R_{14}$, —$C(=NR_{14})OR_{14}$, —$C(=NR_{14})NR_{14}(R_{15})$, —$C(=NR_{14})SR_{14}$,
—$C(=S)R_{14}$, —$C(=S)OR_{14}$, —$C(=S)NR_{14}(R_{15})$, —$C(=S)SR_{14}$,
—$NR_{14}C(=O)NR_{14}(R_{15})$, —$NR_{14}(=NR_{15})NR_{14}(R_{15})$, —$NR_{14}C(=S)NR_{14}(R_{15})$,
—$S(=O)_2R_{14}$, —$S(=O)_2OR_{14}$, —$S(=O)_2NR_{14}(R_{15})$, —$OC(=O)R_{14}$, —$OC(=O)OR_{14}$, —$OC(=O)NR_{14}(R_{15})$, —$OC(=O)SR_{14}$,
—$OS(=O)_2OR_{14}$, —$OS(=O)_2NR_{14}(R_{15})$, and —$OP(=O)_2(OR_{14})$, wherein each X is independently a halogen; and $R_{14}$ and $R_{15}$ are independently hydrogen, C1-C6 alkyl, C6-C14 aryl, arylalkyl, C3-C10 heteroaryl, and heteroarylalkyl, as defined herein.

The term "aralkyl" refers to an alkyl group as defined herein with an aryl group, optionally substituted, as defined herein substituted for one of the alkyl group hydrogen atoms. Suitable aralkyl groups include benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the terms aralkanyl, aralkenyl, and aralkynyl are used. In certain embodiments, the aralkyl group is a C6-C20 aralkyl group, (e.g., the alkanyl, alkenyl, or alkynyl moiety of the aralkyl group is a C1-C6 group and the aryl moiety is a C5-C14 group). In other embodiments, the aralkyl group is a C6-C13 aralkyl group (e.g., the alkanyl, alkenyl, or alkynyl moiety of the aralkyl group is a C1-C3 group and the aryl moiety is a C5-C10 aryl group. In certain embodiments, the aralkyl group is a benzyl group.

The term "heteroaryl" refers to a monovalent heteroaromatic group derived by the removal of one hydrogen atom from a single atom of a parent heteroaromatic ring system, which may be monocyclic or fused ring (i.e., rings that share an adjacent pair of atoms). A "heteroaromatic" group is a 5- to 14-membered aromatic mono- or bicyclic ring containing 1-4 heteroatoms selected from O, S, and N. Representative 5- or 6-membered aromatic monocyclic ring groups include pyridine, pyrimidine, pyridazine, furan, thiophene, thiazole, oxazole, and isooxazole. Representative 9- or 10-membered aromatic bicyclic ring groups include benzofuran, benzothiophene, indole, pyranopyrrole, benzopyran, quionoline, benzocyclohexyl, and naphthyridine. Suitable heteroaryl groups include groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group is a 5-14 membered heteroaryl group. In other embodiments, the heteroaryl group is a 5-10 membered heteroaryl group. Preferred heteroaryl groups are those derived from thiophene, pyrrole, benzothiophene, benzofuran, indole, pyridine, quinoline, imidazole, oxazole, and pyrazine. The heteroaryl group may be substituted or unsubstituted. Representative heteroaryl group substituents include those described above for aryl groups.

The term "heteroarylalkyl" refers to an alkyl group as defined herein with a heteroaryl group, optionally substituted, as defined herein substituted for one of the alkyl group hydrogen atoms. Where specific alkyl moieties are intended, the terms heteroarylalkanyl, heteroarylalkenyl, or heteroarylalkynyl are used. In certain embodiments, the heteroarylalkyl group is a 6-20 membered heteroarylalkyl (e.g., the alkanyl, alkenyl or alkynyl moiety of the heteroarylalkyl is a C1-C6 group and the heteroaryl moiety is a 5-14-membered heteroaryl group. In other embodiments, the heteroarylalkyl group is a 6-13 membered heteroarylalkyl (e.g., the alkanyl, alkenyl or alkynyl moiety is C1-C3 group and the heteroaryl moiety is a 5-10-membered heteroaryl group).

The term "acyl" group refers to the —C(=O)—R' group, where R' is selected from optionally substituted alkyl, optionally substituted aryl, and optionally substituted heteroaryl, as defined herein.

The term "halogen" or "halo" refers to fluoro, chloro, bromo, and iodo groups.

The term "substituted" refers to a group in which one or more hydrogen atoms are each independently replaced with the same or different substituent(s).

Representative compounds of the invention and related intermediates were prepared from commercially available starting materials or starting materials prepared by conventional synthetic methodologies. Representative compounds of the invention were prepared according to Methods A to F as described below and illustrated in FIGS. 1-3. The preparations of certain intermediates (I-1 to I-10) useful in the preparation of compounds of the invention are described in the Synthetic Intermediate section below.

Figure 2:
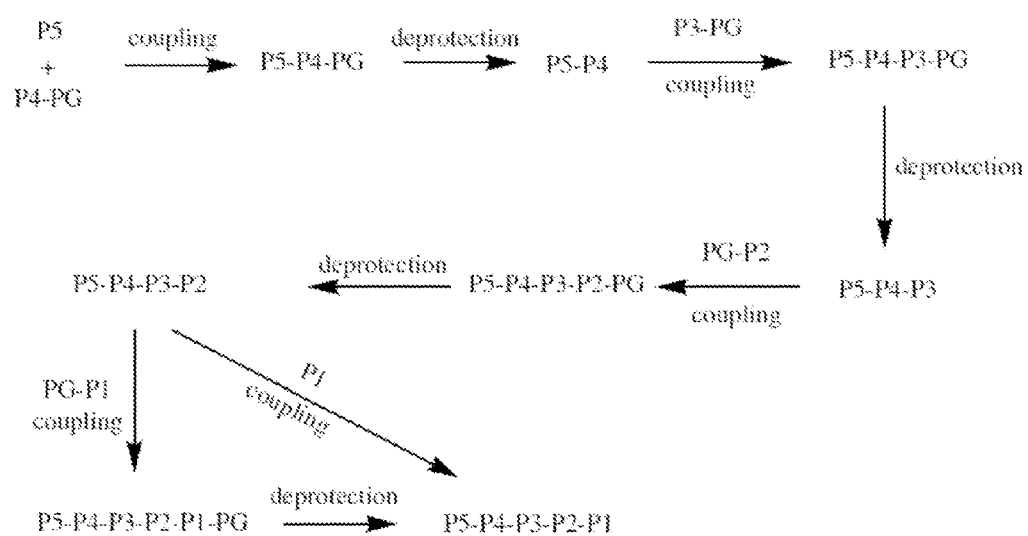
FIG. 2 is a schematic illustration of another representative synthetic pathway for the preparation of representative compounds of the invention P5-P4-P3-P2-P1 starting from P5.)
Figure 3:
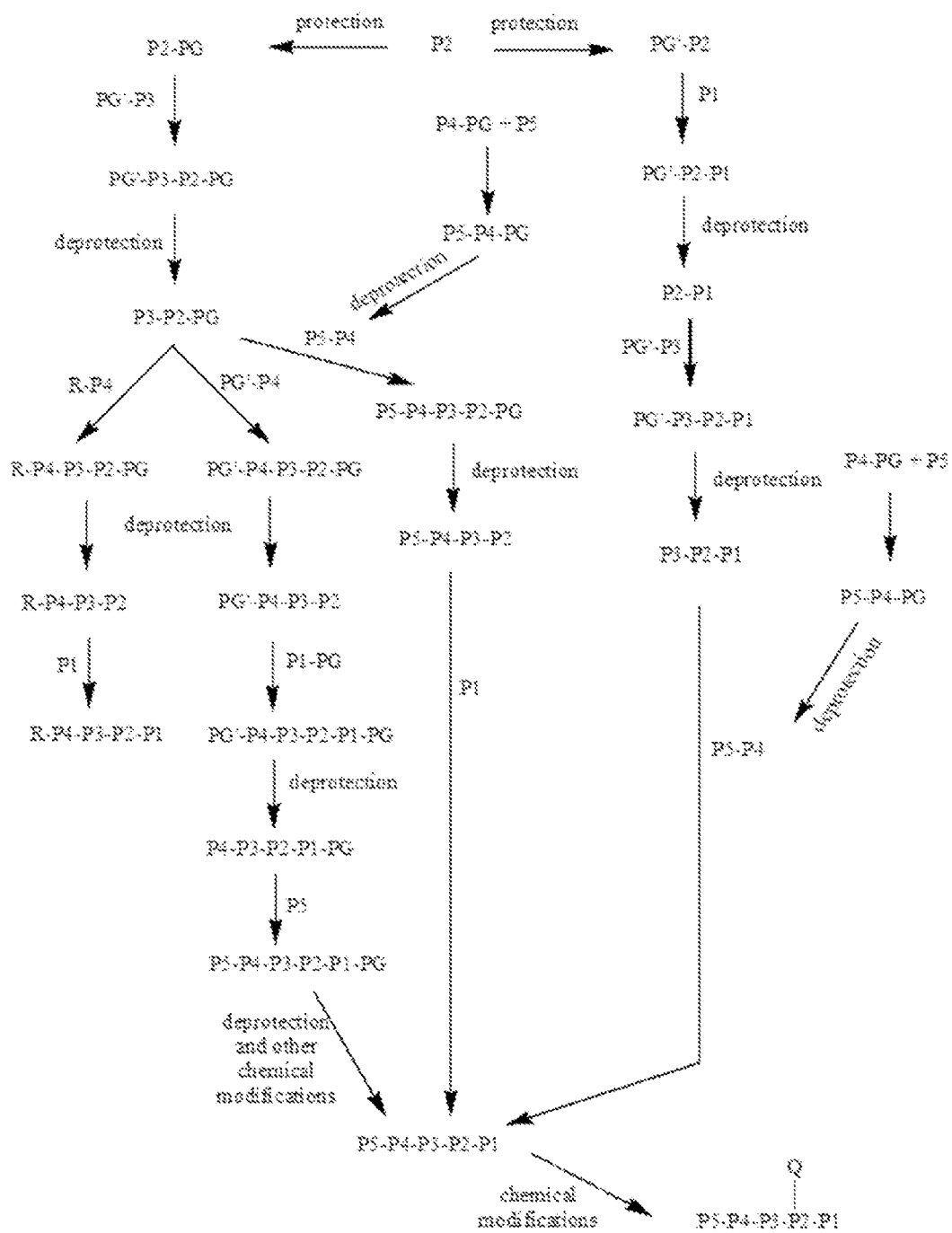
FIG. 3 is a schematic illustration of a further representative synthetic pathway for the preparation of representative compounds of the invention P5-P4-P3-P2-P1 starting from a component other than P1 or P5.

FIGS. 1-3 present schematic illustrations of representative synthetic pathways for the preparation of representative compounds of the invention P5-P4-P3-P2-P1. As used herein, "P5-P4-P3-P2-P1" refers to compounds of the invention prepared from five (5) components: P1, P2, P3, P4, and P5. Protected version of the components useful in the preparation of the compounds of the invention are designated as, for example, "PG-P2," "PG-P2-P1," "PG-P3," and "PG-P3-P2-P1," where "PG" is refers to a protecting group that allows for the coupling of, for example, P1 to P2 or P3 to P1-P2, and that is ultimately removed to provide, for example, P1-P2 or P1-P2-P3.

FIG. 1 is a schematic illustration of another representative synthetic pathway for the preparation of representative compounds of the invention P5-P4-P3-P2-P1 starting from P5. In this pathway, compound P5-P4-P3-P2-P1 is prepared in a stepwise manner starting with P5 by sequential coupling steps, separated as appropriate by deprotection steps and other chemical modifications. As shown in FIG. 1, P5 is coupled with PG-P4 to provide P5-P4-PG, which is then deprotected to provide P5-P4 and ready for coupling with the next component, P3-PG. The process is continued with subsequent couplings PG-P2 with P5-P4-P3 and PG-P1 with P5-P4-P3-P2 to ultimately provide P5-P4-P3-P2-P1.

FIG. 2 is a schematic illustration of a representative synthetic pathway for the preparation of representative compounds of the invention P5-P4-P3-P2-P1 starting from P1. In this pathway, compound P5-P4-P3-P2-P1 is prepared in a stepwise manner starting with P1 by sequential coupling steps, separated as appropriate by deprotection steps and other chemical modifications. As shown in FIG. 2, P1 is coupled with PG-P2 to provide PG-P2-P1, which is then deprotected to provide P2-P1 and ready for coupling with the next component, PG-P3. The process is continued with subsequent couplings PG-P4 with P3-P2-P1 and PG-P5 with P4-P3-P2-P1 to ultimately provide P5-P4-P3-P2-P1.

FIG. 3 is a schematic illustration of a further representative synthetic pathway for the preparation of representative compounds of the invention P5-P4-P3-P2-P1 starting from a component other than P1 or P5. In this pathway, compound P5-P4-P3-P2-P1 is prepared in a stepwise manner starting with P2 by sequential coupling steps, separated as appropriate by deprotection steps and other chemical modifications. As shown in FIG. 3, there are multiple pathways to P5-P4-P3-P2-P1. Examples C1-C8 were prepared by this method.

The preparation of representative compounds and their characterization are described in Examples C1-C8. The structures of representative compounds are set forth in Table 1.

TABLE 1

Representative Compounds.

| Cmpd # | Structure |
|---|---|
| C1 | 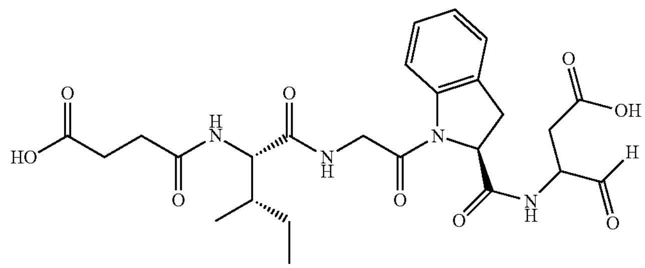 [SMILES: CC[C@H](C)[C@H](NC(=O)CCC(=O)O)C(=O)NCC(=O)N1c2ccccc2C[C@H]1C(=O)NC(C=O)CC(=O)O] |
| C2 | 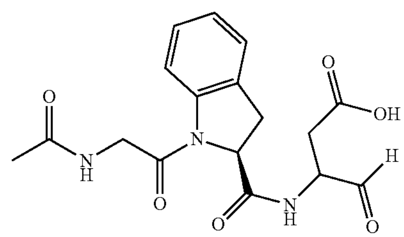 [SMILES: CC(=O)NCC(=O)N1c2ccccc2C[C@H]1C(=O)NC(C=O)CC(=O)O] |
| C3 | 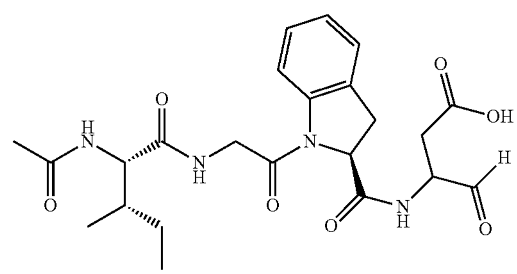 [SMILES: CC[C@H](C)[C@H](NC(C)=O)C(=O)NCC(=O)N1c2ccccc2C[C@H]1C(=O)NC(C=O)CC(=O)O] |
| C4 | 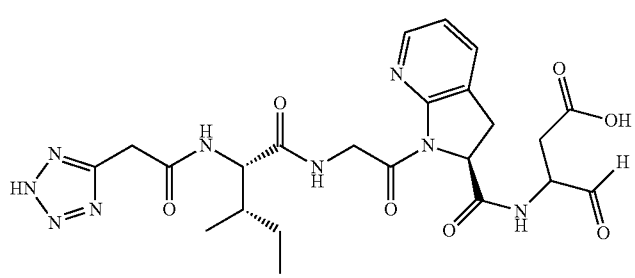 [SMILES: CC[C@H](C)[C@H](NC(=O)Cc1nn[nH]n1)C(=O)NCC(=O)N1c2ncccc2C[C@H]1C(=O)NC(C=O)CC(=O)O] |

TABLE 1-continued

Representative Compounds.

| Cmpd # | Structure |
|---|---|
| C5 | 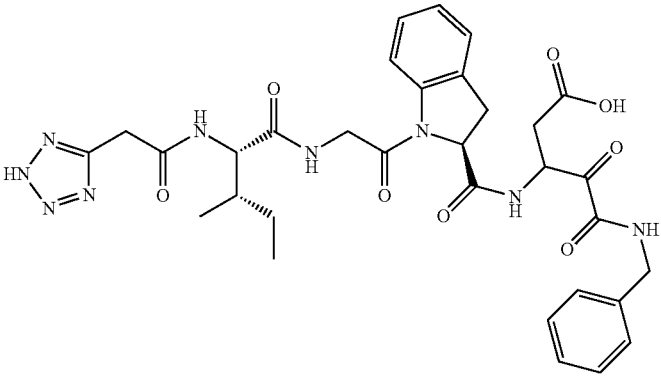 [SMILES: CC[C@H](C)[C@H](NC(=O)Cc1nn[nH]n1)C(=O)NCC(=O)N1c2ccccc2C[C@H]1C(=O)NC(CC(=O)O)C(=O)C(=O)NCc1ccccc1] |
| C6 | 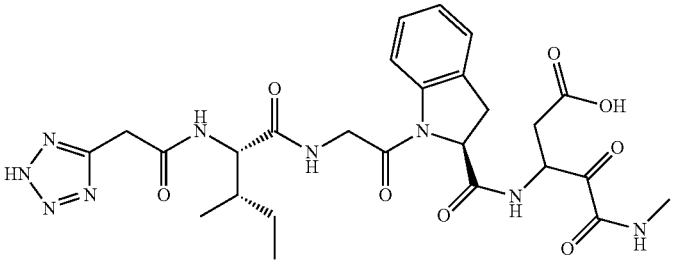 [SMILES: CC[C@H](C)[C@H](NC(=O)Cc1nn[nH]n1)C(=O)NCC(=O)N1c2ccccc2C[C@H]1C(=O)NC(CC(=O)O)C(=O)C(=O)NC] |
| C7 | 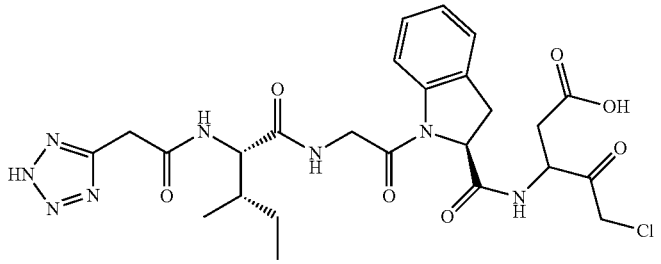 [SMILES: CC[C@H](C)[C@H](NC(=O)Cc1nn[nH]n1)C(=O)NCC(=O)N1c2ccccc2C[C@H]1C(=O)NC(CC(=O)O)C(=O)CCl] |
| C8 | 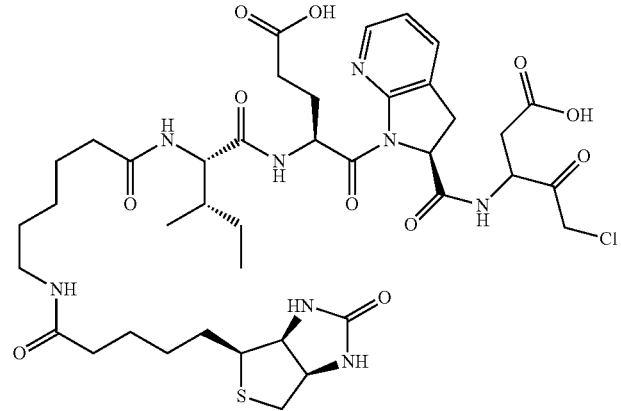 [SMILES: CC[C@H](C)[C@H](NC(=O)CCCCCNC(=O)CCCC[C@@H]1SC[C@@H]2NC(=O)N[C@@H]21)C(=O)N[C@@H](CCC(=O)O)C(=O)N1c2ncccc2C[C@H]1C(=O)NC(CC(=O)O)C(=O)CCl] |

A Granzyme B enzymatic inhibition assay is described in Example D1 and Example D2. The compounds of the invention identified in Table 1 exhibited Granzyme B inhibitory activity. In certain embodiments, select compounds exhibited $IC_{50}$<50,000 nM. In other embodiments, select compounds exhibited $IC_{50}$<10,000 nM. In further embodiments, select compounds exhibited $IC_{50}$<1,000 nM. In still further embodiments, select compounds exhibited $IC_{50}$<100 nM. In certain embodiments, select compounds exhibited $IC_{50}$ from 10 nM to 100 nM, preferably from 1 nM to 10 nM, more preferably from 0.1 nM to 1 nM, and even more preferably from 0.01 nM to 0.1 nM.

A fibronectin cleavage assay is described in Example D3.

Pharmaceutical Compositions

The pharmaceutical compositions of the present invention include an inhibitor compound of the invention (e.g., a compound of Formulae (I) or (II)) as an active ingredient or a pharmaceutically acceptable salt thereof in combination with a pharmaceutically acceptable carrier, and optionally other therapeutic ingredients.

The term "pharmaceutically acceptable salts" refers to salts prepared from pharmaceutically acceptable bases including inorganic bases and organic bases. Representative salts derived from inorganic bases include aluminum, ammonium, calcium, copper, ferric, ferrous, lithium, magnesium, manganic, manganous, ammonium, potassium, sodium, and zinc salts. Representative salts derived from pharmaceutically acceptable organic bases include salts of primary, secondary and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and trimethamine.

Compositions can include one or more carriers acceptable for the mode of administration of the preparation, be it by topical administration, lavage, epidermal administration, sub-epidermal administration, dermal administration, sub-dermal administration, transdermal administration, subcutaneous administration, systemic administration, injection, inhalation, oral, or any other mode suitable for the selected treatment. Topical administration includes administration to external body surfaces (e.g., skin) as well as to internal body surfaces (e.g., mucus membranes for vaginal or rectal applications by, for example, suppositories). Suitable carriers are those known in the art for use in such modes of administration.

Suitable compositions can be formulated by means known in the art and their mode of administration and dose determined by a person of skill in the art. For parenteral administration, the compound can be dissolved in sterile water or saline or a pharmaceutically acceptable vehicle used for administration of non-water soluble compounds. For enteral administration, the compound can be administered in a tablet, capsule, or dissolved or suspended in liquid form. The tablet or capsule can be enteric coated, or in a formulation for sustained release. Many suitable formulations are known including, polymeric or protein microparticles encapsulating a compound to be released, ointments, pastes, gels, hydrogels, foams, creams, powders, lotions, oils, semi-solids, soaps, medicated soaps, shampoos, medicated shampoos, sprays, films, or solutions which can be used topically or locally to administer a compound. A sustained release patch or implant may be employed to provide release over a prolonged period of time. Many techniques known to one of skill in the art are described in Remington: the Science & Practice of Pharmacy by Alfonso Gennaro, 20th ed., Williams & Wilkins, (2000). Formulations can contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers can be used to control the release of a compound. Other potentially useful delivery systems for a modulatory compound include ethylene-vinyl acetate copolymer particles, osmotic pumps, implantable infusion systems, and liposomes. Formulations can contain an excipient, for example, lactose, or may be aqueous solutions containing, for example, polyoxyethylene-9-lauryl ether, glycocholate, and deoxycholate, or can be an oily solution for administration in the form of drops, as a gel, or for other semi-solid formulation.

Compounds or pharmaceutical compositions in accordance with this invention or for use in the methods disclosed herein can be administered in combination with one or more other therapeutic agents as appropriate. Compounds or pharmaceutical compositions in accordance with this invention or for use in the methods disclosed herein can be administered by means of a medical device or appliance such as an implant, graft, prosthesis, stents, and wound dressings. Also, implants can be devised that are intended to contain and release such compounds or compositions. An example would be an implant made of a polymeric material adapted to release the compound over a period of time.

One skilled in the art will appreciate that suitable methods of administering a Granzyme B inhibitor directly to the eye are available (i.e., invasive and noninvasive methods). Although more than one route can be used to administer the Granzyme B inhibitor, a particular route can provide a more immediate and more effective reaction than another route. The present use is not dependent on the mode of administering the agent to an animal, preferably a human, to achieve the desired effect, and the described routes of administration are exemplary. As such, any route of administration is appropriate so long as the agent contacts an ocular cell. Thus, the Granzyme B inhibitor can be appropriately formulated and administered in the form of an injection, eye lotion, ointment, and implant.

The Granzyme B inhibitor can be applied, for example, systemically, topically, intracamerally, subconjunctivally, intraocularly, retrobulbarly, periocularly (e.g., subtenon delivery), subretinally, or suprachoroidally. In certain cases, it can be appropriate to administer multiple applications and employ multiple routes to ensure sufficient exposure of ocular cells to the Granzyme B inhibitor (e.g., subretinal and intravitreous). Multiple applications of the Granzyme B inhibitor can also be required to achieve the desired effect.

Depending on the particular case, it may be desirable to non-invasively administer the Granzyme B inhibitor to a patient. For instance, if multiple surgeries have been performed, the patient displays low tolerance to anesthetic, or if other ocular-related disorders exist, topical administration of the Granzyme B inhibitor may be most appropriate. Topical formulations are well known to those of skill in the art. Such formulations are suitable in the context of the use described herein for application to the skin or to the surface of the eye. The use of patches, corneal shields (see, U.S. Pat. No. 5,185,152), and ophthalmic solutions (see, e.g., U.S. Pat. No. 5,710,182) and ointments is within the skill in the art.

The Granzyme B inhibitor also can be present in or on a device that allows controlled or sustained release, such as an ocular sponge, meshwork, mechanical reservoir, or mechanical implant. Implants (see U.S. Pat. Nos. 5,443,505, 4,853,224 and 4,997,652), devices (see U.S. Pat. Nos. 5,554, 187, 4,863,457, 5,098,443 and 5,725,493), such as an implantable device (e.g., a mechanical reservoir, an intraocular device or an extraocular device with an intraocular conduit, or an implant or a device comprised of a polymeric composition are particularly useful for ocular administration of the expression vector). The Granzyme B inhibitor also can be administered in the form of sustained-release formulations (see U.S. Pat. No. 5,378,475) comprising, for example, gelatin, chondroitin sulfate, a polyphosphoester, such as bis-2-hydroxyethyl-terephthalate, or a polylactic-glycolic acid.

When used for treating an ocular disease the Granzyme B inhibitor is administered via an ophthalmologic instrument for delivery to a specific region of an eye. Use of a specialized ophthalmologic instrument ensures precise administration while minimizing damage to adjacent ocular tissue. Delivery of the Granzyme B inhibitor to a specific region of the eye also limits exposure of unaffected cells to the Granzyme B inhibitor. A preferred ophthalmologic instrument is a combination of forceps and subretinal needle or sharp bent cannula.

Alternatively, the Granzyme B inhibitor can be administered using invasive procedures, such as, for instance, intravitreal injection or subretinal injection, optionally preceded by a vitrectomy, or periocular (e.g., subtenon) delivery. The pharmaceutical composition of the invention can be injected into different compartments of the eye (e.g., the vitreal cavity or anterior chamber).

While intraocular injection is preferred, injectable compositions can also be administered intramuscularly, intravenously, intraarterially, and intraperitoneally. Pharmaceutically acceptable carriers for injectable compositions are well-known to those of ordinary skill in the art (see Pharmaceutics and Pharmacy Practice, J. B. Lippincott Co., Philadelphia, Pa., Banker and Chalmers, eds., pages 238-250 (1982), and ASHP Handbook on Injectable Drugs, Toissel, 4th ed., pages 622-630 (1986)).

An "effective amount" of a Granzyme B inhibitor or a pharmaceutical composition of the invention as described herein includes a therapeutically effective amount or a prophylactically effective amount. A "therapeutically effective amount" refers to an amount effective, at dosages and for periods of time necessary, to achieve the desired therapeutic result, such as reduced levels of Granzyme B activity. A therapeutically effective amount of a compound may vary according to factors such as the disease state, age, sex, and weight of the subject, and the ability of the compound to elicit a desired response in the subject. Dosage regimens can be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as Granzyme B activity. Typically, a prophylactic dose is used in subjects prior to or at an earlier stage of disease, so that a prophylactically effective amount may be less than a therapeutically effective amount.

It is to be noted that dosage values can vary with the severity of the condition to be alleviated. For any particular subject, specific dosage regimens can be adjusted over time according to the individual need and the professional judgment of the person administering or supervising the administration of the compositions. Dosage ranges set forth herein are exemplary only and do not limit the dosage ranges that can be selected by a medical practitioner. The amount of active compound(s) in the composition can vary according to factors such as the disease state, age, sex, and weight of the subject. Dosage regimens can be adjusted to provide the optimum therapeutic response. For example, a single bolus can be administered, several divided doses can be administered over time or the dose can be proportionally reduced or increased as indicated by the exigencies of the therapeutic situation. It may be advantageous to formulate parenteral compositions in dosage unit form for ease of administration and uniformity of dosage.

In general, compounds of the invention should be used without causing substantial toxicity. Toxicity of the compounds of the invention can be determined using standard techniques, for example, by testing in cell cultures or experimental animals and determining the therapeutic index (i.e., the ratio between the $LD_{50}$, the dose lethal to 50% of the population, and the $LD_{100}$, the dose lethal to 100% of the population). In some circumstances however, such as in severe disease conditions, it may be necessary to administer substantial excesses of the composition.

Methods of Use

In a further aspect, the invention provides methods of using the compounds of the invention as Granzyme B inhibitors.

In one embodiment, the invention provides a method for inhibiting Granzyme B in a subject. In the method, an effective amount of a compound of the invention (e.g., a compound of Formulae (I) or (II)) is administered to a subject in need thereof.

In another embodiment, the invention provides a method for treating a disease, disorder, or condition treatable by inhibiting Granzyme B. In the method, a therapeutically effective amount of a compound of the invention (e.g., a compound of Formulae (I) or (II)) is administered to a subject in need thereof.

As used herein, the term "disease, disorder, or condition treatable by inhibiting Granzyme B" refers to a disease, disorder, or condition in which Granzyme B is involved in the pathway related to for the disease, disorder, or condition, and that inhibiting Granzyme B results in the treatment or prevention of the disease, disorder, or condition.

Representative methods of treatment using the compounds of the invention include those described for Granzyme B inhibitors in WO 2007/101354 (Methods of Treating, Reducing, and Inhibiting the Appearance of Ageing in the Skin), WO 2009/043170 (Treatment of Dissection, Aneurysm, and Atherosclerosis Using Granzyme B Inhibitors), WO 2012/076985 (Granzyme B Inhibitor Compositions, Methods and Uses for Promoting Wound Healing), each expressly incorporated herein by reference in its entirety. The compounds of the invention are useful for treating, reducing, and inhibiting the appearance of aging of the skin; treating dissection, aneurysm, and atherosclerosis; and promoting wound healing.

Other disease and disorders described as treatable using the Granzyme B inhibitors are disclosed in WO 2003/065987 (Granzyme B Inhibitors), expressly incorporated herein by reference in its entirety. Disease and disorders described as treatable by Granzyme B inhibitors in this reference include autoimmune or chronic inflammatory diseases, such as systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy, asthma, scleroderma and Sjogren's syndrome. The Granzyme B inhibitors described in the reference are noted as more particularly useful to treat or prevent diseases or disorders including diseases or disorders resulting from transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fasciitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection. To the extent that the diseases and disorders noted in the reference are treatable by the Granzyme B inhibitors described in the reference, the Granzyme B inhibitors of the present invention are also useful in treating and/or ameliorating a symptom associated with these diseases and conditions.

Elevated Granzyme B levels have been identified in cells and tissues from subjects suffering from a variety of diseases and conditions including Rasmussen encephalitis, amyotrophic lateral sclerosis (ALS), chronic inflammation, Stevens-Johnson syndrome (SJS), toxic epidermal necrolysis (TEN), Kawasaki disease, idiopathic pulmonary fibrosis, chronic obstructive pulmonary disease (COPD), coronary artery disease (CAD), transplant vascular disease (TVD), restenosis, acute respiratory distress syndrome (ARDS), chronic obstructive sialadentis (associated with sialolithiasis), vitiligo, allergic contact dermatitis (ACD), atopic dermatitis (AD), pityriasis rosea (PR), rheumatoid arthritis (RA), osteoarthritis (OA), vasculitic neuropathy, sensory perineuritis, ischemic stroke, spinal cord injury, myasthenia gravis (MG), lymphocytic gastritis, autoimmune cholangitis (AIC), nodular regenerative hyperplasia (NRH) of the liver, achalasia, esophagitis, eosinophilic fasciitis, cryptorchidism, necrotizing lymphadenitis, Duchenne muscular dystrophy, facioscapulo humeral muscular dystrophy, and Higashi syndrome. Other diseases and conditions in which elevated Granzyme B levels have been identified include those described in WO 2009/043167 (Granzyme A and Granzyme B Diagnostics), expressly incorporated herein by reference in its entirety. The Granzyme B inhibitors of the invention may be useful for treating, alleviating or ameliorating a symptom of, diminishing the extent of, stabilizing, or ameliorating or palliating the diseases and conditions noted above in which elevated Granzyme B levels have been identified. A description of intracellular versus extracellular Granzyme B in immunity and disease is provided in Granville et al., Laboratory Investigation, 2009, 1-26, expressly incorporated herein by reference in its entirety. The reference provides a listing of conditions in which the pathogenic role of Granzyme B has been identified.

The compounds of the invention are useful in treating cutaneous scleroderma, epidermolysis bullosa, radiation dermatitis, alopecia areata, and discoidal lupus erythematosus.

Cutaneous Scleroderma.

Scleroderma refers to a heterogeneous group of autoimmune fibrosing disorders. Limited cutaneous systemic sclerosis (CREST syndrome or LcSSc) develop sclerosis of the skin distal to their elbows and knees and have facial involvement. Patients with diffuse cutaneous systemic sclerosis (DcSSc) develop proximal, in addition to distal, skin sclerosis. Both groups of patients are also at high risk of developing internal organ involvement. Patients with LcSSc and DcSSc suffer from Raynaud's phenomenon (excessively reduced blood flow in response to cold or emotional stress, causing discoloration of the fingers, toes, and occasionally other areas believed to be the result of vasospasms that decrease blood supply to the respective regions) with high frequencies. Management of progressive skin involvement is dependent on additional comorbidities. In patients with skin involvement only, mycophenolate mofetil (Cellsept, immunomodulator) or methotrexate (T cell modulator) have been recommended.

Epidermolysis Bullosa.

Epidermolysis bullosa acquisita (EBA) is a chronic mucocutaneous autoimmune skin blistering disease. EBA patients can be classified into two major clinical subtypes: noninflammatory (classical or mechanobullous) and inflammatory EBA, which is characterized by cutaneous inflammation. In patients with inflammatory EBA, widespread vesiculobullous eruptions are observed, typically involving the trunk, central body, extremities, and skin folds. Usually the patients suffer from pruritus (rashes). Autoantibodies targeting type VII collagen (COLT) has been implicated in the pathogenesis. Therefore, EBA is a prototypical autoimmune disease with a well-characterized pathogenic relevance of autoantibody binding to the target antigen. EBA is a rare disease with an incidence of 0.2-0.5 new cases per million and per year. The current treatment of EBA relies on general immunosuppressive therapy, which does not lead to remission in all cases.

Radiation Dermatitis.

Radiation Dermatitis (acute skin reaction) ranges from a mild rash to severe ulceration. Approximately 85-90% of patients treated with radiation therapy will experience a moderate-to-severe skin reaction. Acute radiation-induced skin reactions often lead to itching and pain, delays in treatment, and diminished aesthetic appearance—and subsequently to a decrease in quality of life. Skin reactions related to radiation therapy usually manifest within 1-4 weeks of radiation start, persist for the duration of radiation therapy, and may require 2-4 weeks to heal after completion of therapy. The severity of the skin reaction ranges from mild erythema (red rash) and dry desquamation (itchy, peeling skin) to more severe moist desquamation (open wound) and ulceration. Treatments that have been assessed for the management of radiation-induced skin reactions include topical steroid creams, nonsteroidal creams, dressings, and herbal remedies. Only three trials have showed a significant difference: one in favor of a corticosteroid cream, one favoring a nonsteroidal cream, and one for a dressing. However, all three of these trials were small and had limitations, thus there is still an unmet medical need.

Late effects of radiation therapy, typically months to years post exposure, occur at doses greater than a single dose of 20-25 Gy or fractionated doses of 70 Gy or higher. The major underlying histopathological findings at the chronic stage include telangiectasia, dense dermal fibrosis (round fibrosis), sebaceous and sweat gland atrophy, loss of hair follicles, and with higher doses, increased melanin deposition or depigmentation and skin ulcers.

Ramipril was very effective in reducing the late effects of skin injury, whereas its mitigating effects on the acute and sub-acute injury were modest. However, the dose required to mitigate these late effects may be pharmacologically too high to be clinically relevant. More recently, it has been shown that significant mitigation of acute skin injury using an adeno-associated virus encoding the manganese SOD gene, when injected subcutaneously shortly after irradiation. However, difficulties in delivery, application and cost limit the utility of this treatment strategy.

Alopecia Aerata.

Alopecia areata (AA) is a CD8+ T-cell dependent autoimmune disease of the hair follicle (HF) in which the collapse of HF immune privilege (IP) plays a key role. Mast cells (MCs) are crucial immunomodulatory cells implicated in the regulation of T cell-dependent immunity, IP, and hair growth. Many of these infiltrating immune cells express GzmB, suggesting it may be a key mediator in immune cell-mediated follicular attack. The peptide substance P was shown to increase the CD8+ cells expressing GzmB in the intrafollicular dermis, co-relating to a regression of follicles into the catagen stage of follicle growth cessation (Siebenhaar et al., *J Invest Dermatol,* 2007, 127: 1489-1497).

In mice fed a diet with excess vitamin A, AA was accelerated and GzmB expressing cells were found in excess surrounding hair follicles, including in the isthmus (the region of the follicle containing stem cells) (Duncan et al., *J Invest Dermatol* 2013, 133: 334-343). As GzmB is expressed in the immune cell infiltrate within and surrounding growing follicles, it may be a key protease involved in hair loss through autoimmunity, apoptosis and ECM degradation.

No drug is currently approved by the US FDA for the treatment of alopecia areata. A number of treatments have been found to be effective using the American College of Physician's criteria, for example, topical and oral corticosteroids and the sensitizing agents diphenylcyclopropenone and dinitrochlorobenzene. However, there is no cure for alopecia areata, nor is there any universally proven therapy that induces and sustains remission.

Discoid Lupus Erythematosus.

Granzyme B is a serine protease found in cytoplasmic granules of cytotoxic lymphocytes and natural killer cells that plays an important role in inducing apoptotic changes in target cells during granule exocytosis-induced cytotoxicity. When Granzyme B is secreted into the cytoplasm of a target cell through the pore formed by perforin, it triggers cytotoxic-induced cell death (Shah et al., *Cell Immunology* 2011, 269:16-21).

Lupus erythematosus (LE) is a chronic, autoimmune, multisystem disease that displays many diverse symptoms in which localized cutaneous LE (CLE) is on one end of the spectrum and severe systemic LE (SLE) on the other end. CLE is a disfiguring, chronic skin disease, with a significant impact on the patients' everyday life. CLE are further divided into four main subsets: Acute CLE (ACLE), sub-acute CLE (SCLE) and chronic CLE (CCLE), where classic discoid LE (DLE) is the most common form. There is also a drug-induced form of the disease. The disease often has a chronic and relapsing course that can be induced or aggravated by UV light. CLE patients display well-defined skin lesions, often in sun-exposed areas. Discoid LE is the most common subtype of CLE, 60-80% is localized above the neck and 20-40% is generalized (lesions both above and below the neck). 70-90% of the DLE patients suffer from photosensitivity and sun exposed areas such as the scalp, ears and cheeks, which are most commonly involved areas. The lesions start as erythematosus maculae or papules with a scaly surface and then grow peripherally into larger discoid plaques that heal with atrophic scar and pigmentary changes. DLE often results in scarring and alopecia. Mutilation with tissue loss can be seen when the lesions affect the ears and tip of the nose. CLE can be managed but so far, not cured. Avoidance of trigger factors is of utmost importance, such as, cessation of smoking and avoidance of sun exposure. The treatment is about the same for the different CLE subsets where first-line of treatment is sun-protection and local therapy with corticosteroids or calcineurin inhibitors. Antimalarial are the first choice of systemic treatment.

Strong co-expression of Granzyme B and the skin-homing molecule, cutaneous lymphocyte antigen (CLA) was found in lesional lymphocytes of patients with scarring localized chronic DLE and disseminated chronic DLE, which was enhanced compared with nonscarring subacute CLE and healthy controls (Wenzel et al., *British Journal of Dermatology* 2005, 153: 1011-1015). Wenzel et al. conclude that skin-homing cytotoxic Granzyme B-positive lymphocytes play an important role in the pathophysiology of scarring chronic DLE and that the potentially autoreactive cytotoxic lymphocytes targeting adnexal structures may lead to scarring lesions in chronic DLE.

Correlation between Granzyme B-positive lymphocytes and the presence of CLE was shown by Grassi (Grassi et al.,

*Clinical and Experimental Dermatology* 2009, 34:910-914). Granzyme B is an apoptosis immunological mediator that, once synthesized and free from activated cytotoxic lymphocytes, enters the target cell and starts apoptotic mechanisms involved at different levels in all apoptotic pathways. In CLE, apoptosis is characterized by the presence of colloid or Civatte bodies, which are evident in the epidermis and papillary dermis of CLE lesions, and since Granzyme B is mainly expressed in CLE lesions, Grassi et al. conclude that Granzyme B could play a role in the induction of apoptotic mechanisms in CLE.

The expression of Granzyme B and perforin was correlated with clinicopathological features in patients with DLE, where both Granzyme B and perform were expressed in DLE, with absent expression in normal skin (Abdou et al., *Ultrastructural Pathology* 2013, Early Online 1-9). Abdou et al. concluded that cytotoxicity in dermal lymphocytic inflammation was due to expression of both Granzyme B and perforin.

Extracellular Granzymes B is also reported to play a role in DLE by Grassi et al. Further, UV light increases Granzyme B expression in keratinocytes as well as mast cells (Hernandez-Pigeon, *J. Biol. Chem.,* 2007, 282:8157-8164). As Granzymes B is in abundance at the dermal-epidermal junction (DEJ), where many key extracellular matrix substrates are present (for example, laminin, fibronectin, decorin), it follows that Granzymes B may also be damaging the DEJ, as is observed in DLE. Given its expression in adnexal structures, Granzyme B may also be contributing to alopecia, as reduced Granzymes B is associated with reduced hair loss in a murine model of skin aging. Similarly, reduced extracellular Granzyme B activity is associated with improved collagen organization and reduced scarring in the skin and aorta.

In view of the established connection between Granzyme B and DLE, by virtue of their ability to inhibit Granzyme B, the compounds of the invention are useful in methods for treating lupus erythematosus (LE) including severe systemic LE (SLE) and localized cutaneous LE (CLE) (e.g., acute CLE (ACLE), subacute CLE (SCLE), chronic CLE (CCLE) and the most common form classic discoid LE (DLE)). In one embodiment, the invention provides a method for treating DLE comprising administering a therapeutically effective amount of a compound of the invention to a subject suffering from DLE.

Administration.

In the above methods, the administration of the Granzyme B inhibitor can be a systemic administration, a local administration (e.g., administration to the site, an inflamed microenvironment, an inflamed joint, an area of skin, a site of a myocardial infarct, an eye, a neovascularized tumor), or a topical administration to a site (e.g., a site of inflammation or a wound).

The term "subject" or "patient" is intended to include mammalian organisms. Examples of subjects or patients include humans and non-human mammals, e.g., nonhuman primates, dogs, cows, horses, pigs, sheep, goats, cats, mice, rabbits, rats, and transgenic non-human animals. In specific embodiments of the invention, the subject is a human.

The term "administering" includes any method of delivery of a Granzyme B inhibitor or a pharmaceutical composition comprising a Granzyme B inhibitor into a subject's system or to a particular region in or on a subject. In certain embodiments, a moiety is administered topically, intravenously, intramuscularly, subcutaneously, intradermally, intranasally, orally, transcutaneously, intrathecal, intravitreally, intracerebral, or mucosally.

As used herein, the term "applying" refers to administration of a Granzyme B inhibitor that includes spreading, covering (at least in part), or laying on of the inhibitor. For example, a Granzyme B inhibitor may be applied to an area of inflammation on a subject or applied to, for example the eye or an area of inflammation by spreading or covering the surface of the eye with an inhibitor, by injection, oral or nasal administration.

As used herein, the term "contacting" includes contacting a cell or a subject with a Granzyme B inhibitor. Contacting also includes incubating the Granzyme B inhibitor and the cell together in vitro (e.g., adding the inhibitor to cells in culture) as well as administering the inhibitor to a subject such that the inhibitor and cells or tissues of the subject are contacted in vivo.

As used herein, the terms "treating" or "treatment" refer to a beneficial or desired result including, but not limited to, alleviation or amelioration of one or more symptoms, diminishing the extent of a disorder, stabilized (i.e., not worsening) state of a disorder, amelioration or palliation of the disorder, whether detectable or undetectable. "Treatment" can also mean prolonging survival as compared to expected survival in the absence of treatment.

Cosmetic Compositions and Related Methods

In further aspects, the invention provides cosmetic compositions that include one or more granzyme B inhibitors of the invention and methods for using the compositions to treat, reduce, and/or inhibit the appearance of ageing of the skin.

This aspect of the invention is based, in part, on the observation that granzyme B expression is induced in keratinocytes and immune cells, such as mast cells in the skin during aging. When released by these cells, granzyme B cleaves extracellular matrix proteins such as decorin which can result in collagen disorganization. This invention is also based in part on the observation that granzyme B cleaves decorin, in addition to other extracellular matrix proteins, in the interstitial space surrounding cells.

Skin is comprised of three main layers: the epidermis, the dermis and subcutaneous layers. Each of these three layers has individual compositions. The functions and structures of these layers are known to a person of skill in the art. The epidermis is the outermost layer of skin and includes both living and dead cell layers. The dermis is the middle layer of skin and is comprised of arrangements of collagen fibers, which surround many specialized cells and structures. Hair follicles are found within the dermis, and produce the hair shaft which grows out through layers of the dermis and epidermis to become visible as hair. The lowermost layer of the skin is the subcutaneous layer, often called the subdermis. The subcutaneous layer is comprised largely of fat and connective tissue and houses larger blood vessels and nerves. Collagen may be found in all layers of the skin, but is most prominently in the dermis layer.

A youthful appearance is achieved by not having at least one of the characteristic signs of age. This is often achieved by being young. Nevertheless, there are circumstances in which being young does not confer a youthful appearance as a disease or disorder or other non-time related event has conferred the characteristics associated with age. A youthful appearance is often characterized by the condition of the skin and the following skin qualities are typically associated with, but not limited to, a youthful appearance: small pore size, healthy skin tone, radiance, clarity, tautness, firmness, plumpness, suppleness, elasticity, softness, healthy skin texture, healthy skin contours, such as few or no wrinkles, shallow wrinkle depth, few or no fine lines, healthy skin luster and brightness, moisturized skin, healthy skin thickness and resilient skin. If a skin of a subject comprises any one or more of these characteristics then a youthful appearance is achieved.

The appearance of ageing can occur for a variety of reasons, but typically happens at a normal rate associated with the passage of time. A rate of appearance of ageing will be different for different subjects, depending on a variety of factors including age, gender, diet and lifestyle. An appearance of ageing is often characterized by the condition of the skin. Characteristics associated with an appearance of ageing in the skin include, but are not limited to, skin fragility, skin atrophy, skin wrinkles, fine lines, skin discoloration, skin sagging, skin fatigue, skin stress, skin inelasticity, skin fragility, skin softening, skin flakiness, skin dryness, enlarged pore size, skin thinning, reduced rate of skin cell turnover, deep and deepening of skin wrinkles. The rate of appearance of ageing can be measured by measuring the rate at which any one or more of the above characteristics appear. An appearance of ageing may be inhibited, reduced, or treated by reducing or maintaining a state of any one or more of these skin characteristics.

In many circumstances a reduction in the appearance of ageing of skin occurs when the rate of collagen cleavage exceeds the rate of collagen formation. In many other circumstances, a youthful appearance of skin is maintained when the rate of collagen formation is equal to the rate of collagen cleavage. In many other circumstances, a reduction in a rate of appearance of ageing of skin is achieved when the rate of decorin cleavage and collagen disorganization and cleavage is slowed such that the rate of collagen fibrillogenesis exceeds the rate of collagen cleavage and the ratio of the rate of collagen fibrillogenesis to the rate of collagen cleavage is greater after application of granzyme B inhibitor compound compared to the ratio before application of the compound. In many other circumstances, an extracellular protein, other than decorin, is also cleaved by granzyme B, and the beneficial effects of inhibiting granzyme B can be enhanced beyond what is realized by inhibiting decorin cleavage alone.

In one aspect, the invention provides a cosmetic composition. The composition comprises a cosmetically acceptable carrier and one or more compounds of the invention (e.g., a compound of Formulae (I) or (II), or stereoisomers, tautomers, and cosmetically acceptable salts thereof, as described herein).

As used herein, the term "cosmetically acceptable salt" refers to a salt prepared from a cosmetically acceptable base, such as an inorganic base and an organic base, or a salt prepared from a cosmetically acceptable acid. Representative salts derived from inorganic bases include aluminum, ammonium, calcium, copper, ferric, ferrous, lithium, magnesium, manganic, manganous, ammonium, potassium, sodium, and zinc salts. Representative salts derived from cosmetically acceptable organic bases include salts of primary, secondary and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and trimethamine.

The cosmetic compositions can be formulated by means known in the art and their mode of administration and the amount of granzyme B inhibitor compound as described herein can be determined by a person of skill in the art. Compositions for use in the methods described herein can comprise one of more of a granzyme B inhibitor compound or a cosmetically acceptable salt thereof as an active ingredient, in combination with a cosmetically acceptable carrier.

The cosmetic compositions can include diluents, excipients, solubilizing agents, emulsifying agents, and salts known to be useful for cosmetic compositions. Examples of suitable agents include thickeners, buffers, preservatives, surface active agents, neutral or cationic lipids, lipid complexes, liposomes, and penetration enhancers. In certain embodiments, the cosmetic compositions further include other cosmetic ingredients known in the art.

In certain embodiments, the cosmetic composition can include one or more penetration enhancers. Numerous types of penetration enhancers are known, such as fatty acids, bile salts, chelating agents, surfactants and non-surfactants (Lee et al., Critical Reviews in Therapeutic Drug Carrier Systems 8:91-192, 1991; Muranishi, Critical Reviews in Therapeutic Drug Carrier Systems 7:1-33, 1990). Fatty acids and their derivatives which act as penetration enhancers include, for example, cabrylic acid, oleic acid, lauric acid, capric acid, caprylic acid, hexanoic acid, myristic acid, palmitic acid, valeric acid, stearic acid, linoleic acid, linolenic acid, arachidonic acid, oleic acid, elaidic acid, erucic acid, nervonic acid, dicaprate, tricaprate, recinleate, monoolein (also known as 1-monooleoyl-rac-glycerol), dilaurin, arachidonic acid, glyceryll-monocaprate, 1-dodecylazacycloheptan-2-one, acylcarnitines, acylcholines, mono- and di-glycerides and physiologically acceptable salts thereof (e.g., oleate, laurate, caprate, myristate, palmitate, stearate, linoleate) (Lee et al., Critical Reviews in Therapeutic Drug Carrier Systems page 92, 1991; Muranishi, Critical Reviews in Therapeutic Drug Carrier Systems 7:1, 1990; El-Hariri et al., *J. Pharm. Pharmacol.* 44:651-654, 1992).

In certain embodiments, the cosmetic composition further includes other cosmetic ingredients known in the art to be useful for cosmetic, skincare, and/or dermatological applications (e.g., anti-wrinkle active ingredients including flavone glycosides such as alpha-glycosylrutin; coenzyme Q10; vitamin E and derivatives; as well as sunblock ingredients, moisturizers, and perfumes).

The cosmetic compositions of the invention can be administered for "cosmetic" or "skincare" (e.g., dermatologic) applications, either alone or as an "additive" in combination with other suitable agents or ingredients. As used herein, "cosmetic" and "skincare" applications includes, for example, preventive and/or restorative applications in connection with dermatological changes in the skin, such as, for example, during pre-mature skin aging; dryness; roughness; formation of dryness wrinkles; itching; reduced re-fatting (e.g., after washing); visible vascular dilations (e.g., telangiectases, cuperosis); flaccidity; formation of wrinkles and lines; local hyperpigmentation; hypopigmentation; incorrect pigmentation (e.g., age spots); increased susceptibility to mechanical stress (e.g., cracking); skin-sagging (e.g., lack of firmness) and the appearance of dry or rough skin surface features.

The cosmetic compositions of the invention can be formulated for topical administration. Such compositions can be administered topically in any of a variety of forms. Such compositions are suitable in the context of the use described herein for application to the skin or to the surface of the eye. The use of patches, corneal shields (see, U.S. Pat. No.

5,185,152), and ophthalmic solutions (see, for example, U.S. Pat. No. 5,710,182) and ointments is within the skill in the art.

Compositions for topical administration include dermal patches, ointments, lotions, serums, creams, gels, hydrogels, pastes, foams, oils, semi-solids, shampoos, soaps, drops, sprays, films, liquids, and powders. Examples of such compositions include those in which a cosmetically effective amount of a compound of the invention is encapsulated in a vehicle selected from macro-capsules, micro-capsules, nano-capsules, liposomes, chylomicrons and microsponges. Another example of such a composition includes absorption of a compound of the invention on or to a material selected from powdered organic polymers, talcs, bentonites, and other mineral supports. A third example of such a composition or formulation includes a mixture of a cosmetically effective amount of a compound of the invention with other ingredients selected from extracted lipids, vegetable extracts, liposoluble active principles, hydrosoluble active principles, anhydrous gels, emulsifying polymers, tensioactive polymers, synthetic lipids, gelifying polymers, tissue extracts, marine extracts, vitamin A, vitamin C, vitamin D, vitamin E, solar filter compositions, and antioxidants. Other examples of suitable composition ingredients can be found in US2005/0249720.

In the cosmetic compositions, the compounds of the invention can be incorporated into any gelanic form, such as oil/water emulsions and water/oil emulsions, milks, lotions, gelifying and thickening tensioactive and emulsifying polymers, pomades, lotions, capillaries, shampoos, soaps, powders, sticks and pencils, sprays, and body oils.

Regardless of the compound or formulation described herein, application/administration to a subject as a colloidal dispersion system can be used as a delivery vehicle to enhance the in vivo stability of the compound and/or to target the granzyme B inhibitor compound to a particular skin layer, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:inhibitor complexes of uncharacterized structure. An example of a colloidal dispersion system is a plurality of liposomes. Liposomes are microscopic spheres having an aqueous core surrounded by one or more outer layers made up of lipids arranged in a bilayer configuration (see, generally, Chonn et al., *Current Op. Biotech.* 6:698-708, 1995). Sustained-release dosage forms of the compounds described herein can also be used.

The amount of the granzyme B inhibitor compound administered or applied to a subject is not critical, except that it should be an amount sufficient to effect improvement of the condition for which the composition is administered/applied. Application can be dependent on a number of factors, including severity and responsiveness of the condition to be treated, and with the course of treatment lasting from several days to several months, or until improvement of a condition is effected or a diminution of a symptom is achieved.

A "cosmetically effective amount" of a granzyme B inhibitor compound includes a cosmetically effective amount or a prophylactically effective amount. A "cosmetically effective amount" refers to an amount effective, at dosages and for periods of time necessary, to achieve the desired cosmetic result, such as improved skin elasticity, skin durability, skin firming, skin texture, decrease the appearance or decrease rate of appearance of aging, and the like. A cosmetically effective amount of a compound may vary according to factors such as the skin state, age, sex, and weight of the subject, and the ability of the compound to elicit a desired response in the subject. Dosage regimens can be adjusted to provide the optimum cosmetic response. A cosmetically effective amount is also one in which any toxic or detrimental effects of the compound are outweighed by the cosmetically beneficial effects. A "prophylactically effective amount" refers to an amount effective, at dosages and for periods of time necessary, to achieve the desired prophylactic result, such as improved skin elasticity, skin durability, skin firming, skin texture, a decrease appearance or a decrease in the rate of appearance of aging, and the like. Typically, a prophylactic dose is used in subjects prior to or at an earlier stage of skin deterioration, so that a prophylactically effective amount may be less than a cosmetically effective amount.

The amount of granzyme B inhibitor administered/applied may vary with the severity of the appearance, or rate of appearance, of age of the skin. For any particular subject, specific dosage regimens may be adjusted over time according to the individual need and the judgment of the person applying or supervising the applying of the compositions. Dosage ranges set forth herein are exemplary only and do not limit the dosage ranges that may be selected. The amount of granzyme B inhibitor compound(s) in the composition or formulation can vary according to factors such as the skin state, age, sex, and weight of the subject. Dosage regimens can be adjusted to provide the optimum response. For example, a single application can be administered/applied, several divided doses can be administered/applied over time or the amount of the composition administered/applied can be proportionally reduced or increased as indicated by the exigencies of the situation. It can be advantageous to formulate the granzyme B inhibitor compounds in a composition into a dosage unit form for ease of administration and uniformity of application.

By way of example, a granzyme B inhibitor compound of the cosmetic composition can be administered/applied to achieve from about 0.01 micrograms per milliliter (μg/mL) to about 10 milligrams per milliliter, from about 0.1 μg/mL to about 500 μg/mL, from about 0.1 μg/mL to about 1500 μg/mL, from about 1 μg/mL to about 2000 μg/mL, and from about 0.1 μg/mL to about 5000 μg/mL, including any range within these ranges, final concentrations at a target site.

Appropriate dosage values can depend on the characteristics of the site to which the composition is to be applied/administered and on the form of the granzyme B inhibitor compound used. Guidance as to particular dosages and methods of delivery is provided in the literature and generally available to practitioners in the art. Those skilled in the art will employ different formulations for different uses and the granzyme B inhibitor compound used. Persons of ordinary skill in the art can easily estimate repetition rates for dosing based on measured residence times and concentrations of the granzyme B inhibitor compound in, for example, a bodily fluid or a tissue. Following successful treatment, it can be desirable to have the subject undergo maintenance therapy to prevent the recurrence of the condition, wherein a selected compound is administered/applied in maintenance doses applied, for example, once or more daily, to once every few days. In certain embodiments, granzyme B inhibitor compounds are administered/applied in an amount to achieve ex vivo concentrations from about 1 micromolar to about 10 millimolar, from about 10 micromolar to about 5000 micromolar, or from about 30 micromolar to about 3000 micromolar, and from about 25 micromolar to about 3000 micromolar final concentration over a site of interest, and including, about 25 micromolar, or about 1600 micromolar, or about 3000 micromolar final concentration over the site, and still more typically between about 1 micromolar to about 1000 micromolar.

Compounds or compositions of granzyme B inhibitors can be administered/applied by means of a device or appliance such as an implant, graft, prosthesis, garment of clothing, stent, and the like. Also, implants can be devised which are intended to contain and release such compounds or compositions. An example would be an implant made of a polymeric material adapted to release the compound over a period of time. Such implants can be placed into a garment to be worn by a subject, for example a glove, shirt, mask or hat.

The cosmetic compositions of the invention can be used to inhibit or reduce the appearance of ageing. Ageing is a natural phenomenon that cannot be reversed per se, but the appearance of ageing, such as skin deterioration including, but not limited to, skin inelasticity, skin fragility, skin softening, skin flakiness, skin dryness, enlarged pore size, skin thinning, reduced rate of skin cell turnover, skin wrinkling, deepening of skin wrinkles, skin sagging, fine lines, and skin discoloration may be inhibited or reduced.

The cosmetic compositions can be used to increase or decrease a rate of increasing or a rate of decreasing occurrences of a particular skin characteristic. In other words, the composition, when applied to the skin or a portion of the skin of a subject delays the onset of an appearance of aging. For example, in a population of subjects where half of the population applies a granzyme B inhibitor to their skin and another half of the population does not apply a granzyme B inhibitor to their skin, the half which applied a granzyme B inhibitor would not appear as aged as the half which did not apply the granzyme B inhibitor after a period of time had elapsed. The half of the population which applied a granzyme B inhibitor to the skin would also have maintained a youthful appearance.

The rate at which a particular subject experiences a change in the rate of appearance of a particular skin characteristic, i.e., an increasing or decreasing rate of the appearance of a particular skin characteristic, will depend on a variety of factors, including, but not limited to age, weight, sex and lifestyle of the subject. As such, rates are not necessarily constant, but a normal rate of increase or of decrease of an appearance of a characteristic, defined as being the new occurrence of a particular characteristic over a predetermined period of time under a set of conditions that do not include the presence of a granzyme B inhibitor applied by a method or use of this invention, is increased or decreased by applying a granzyme B inhibitor in accordance with a method or use of this invention. Methods of measuring skin characteristics, rates of increasing appearance of skin characteristics and rates of decreasing appearance of skin characteristics are known to a person of skill in the art, see for example, *Measuring the Skin* by Agache et al., Springer (2004).

Surprisingly, granzyme B inhibitors can also be used to increase the density of hair follicles of a skin of a subject and may be used to reduce the occurrences of cutaneous xanthomas of a skin of a subject. Actively growing hair follicles contain melanocytes that transfer pigment to matrix keratinocytes, imparting color to hair. Additionally, sebum, produced in sebaceous glands, is often secreted via hair follicles. Increased density of hair follicles results in increased pigment production and increased sebum secretion resulting in improved hair appearance (e.g., hair that is less grey in color or not grey at all) as well as healthier hair and skin. Granzyme B inhibitors also cause hair follicles to appear deeper in the skin which provide stronger hair that is less susceptible to mechanical damage. Additionally, a characteristic sign of ageing is the reduction in hair follicle density. It is known in the art that age and follicular miniaturization are weak predictors of total hair count (see Chapman et al., *Brit. J. Dermatol.* 152:646-649, 2005). Consequently, the characteristic sign of age associated with hair follicle density is not predictive of hair density.

The cosmetic composition may be applied to a portion of the skin of a subject or to the whole of the skin of the subject. For example, the composition may be applied to the skin, only on the face, only on the scalp, on the whole head or to each part of the body.

INCORPORATION BY REFERENCE

Each reference cited is incorporated herein by reference in its entirety.

Abbreviations

As used herein, the following abbreviations have the indicated meanings.

$^1$H NMR: proton nuclear magnetic resonance
$^{19}$F NMR: fluorine-19 nuclear magnetic resonance
% Inh: Percent inhibition
Ac-IEPD-AMC: acetyl-isoleucyl-glutamyl-prolyl-aspartyl-(7-amino-4-methylcoumarin) substrate
ACN: acetonitrile
BHET: bis-2-hydroxyethyl-terephthalate
Boc: tert-butoxycarbonyl
BSA: Bovine serum albumin
CHAPS: 3-[(3-cholamidopropyl)dimethylammonio]-1-propanesulfonate
DAPI: 4',6-diamidino-2-phenylindole
DCM: dichloromethane
DIPEA: diisopropylethylamine
DMAP: 4-dimethylaminopyridine
DMF: dimethylformamide
DMSO: dimethylsulfoxide
DMSO-d6: dimethylsulfoxide-d6
DTT: dithiothreitol
EDC: 1-(3-dimethylaminopropyl)-3-ethylcarbodiimide hydrochloride
EDTA: 2-({2-[Bis(carboxymethyl)amino]ethyl}(carboxymethyl)amino)acetic acid
ESI: Electrospray ionization
EtOAc: ethyl acetate
eq.: equivalent(s)
GzmB: Granzyme B
HATU: 2-(7-aza-1H-benzotriazole-1-yl)-1,1,1,1-tetramethyluronium hexafluorophosphate
HCl: hydrochloric acid
HEPES: 4-(2-hydroxyethyl)-1-piperazineethanesulfonic acid
hGzmB: human Granzyme B
HPLC: high performance liquid chromatography
HOBt: 1-hydroxy-benzotriazol
$IC_{50}$: inhibitory concentration that provides 50% inhibition
LC/MS: liquid chromatography/mass spectrometry
MeOH: methanol
mGzmB: murine Granzyme B
MS: mass spectrometry
m/z: mass to charge ratio.
Oxyma: ethyl 2-cyano-2-(hydroxyimino)acetate PBS: phosphate buffered saline (pH 7.4)
RPM: revolution per minute
RT: room temperature
tert-BuOH: tert-butyl alcohol
THF: tetrahydrofuran
TFA: trifluoroacetic acid
wt %: weight percent General Methods A-F Representative compounds of the invention were prepared according to Methods A to F as described below and illustrated in FIGS. 1-3.

It will be appreciated that in the following general methods and preparation of synthetic intermediates, reagent levels and relative amounts or reagents/intermediates can be changed to suit particular compounds to be synthesized, up or down by up to 50% without significant change in expected results.

Method A: General Method for Deprotection Followed by Coupling Reaction Using EDC/HOBt/DIPEA.

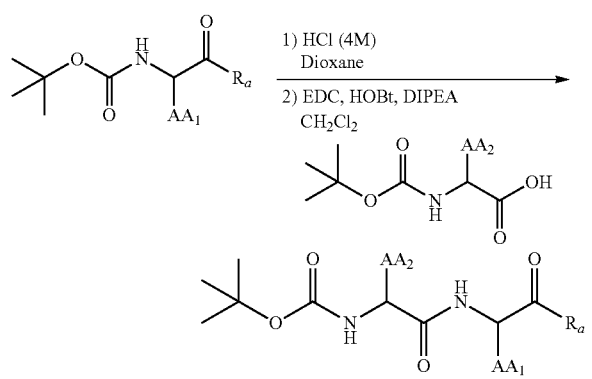

HCl Solution in dioxane (4M, 5 ml) was added to respective carbamate compound (0.125 mmol) and stirred for 2 hrs at RT. The reaction mixture was concentrated to dryness under vacuum and swapped with MeOH (5 ml) three times. The resulting residue was dried well under vacuum and subjected to next reaction as it was. The residue obtained above, respective acid moiety (0.125 mmol), EDC (0.19 mmol), HOBt (0.16 mmol) and DIPEA (0.5 mmol) were stirred in anhydrous DCM (5 ml) for 16 hrs. The reaction mixture was concentrated under vacuum to give the crude product which was purified on a C18 column using 10-50% MeOH in water to yield product as an off-white solid (35-55%).

Method B: General Method for Deprotection Followed by Reaction with Anhydride.

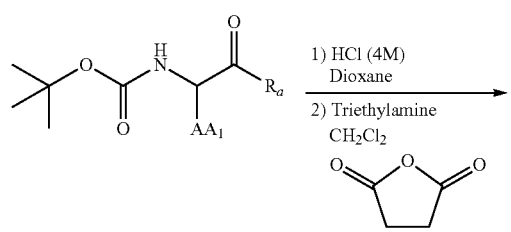

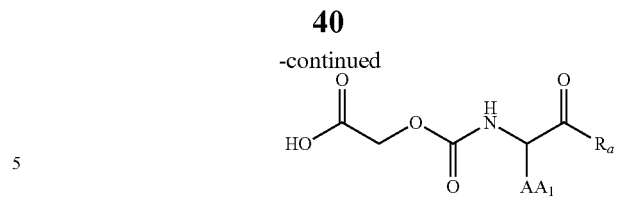

The above scheme and following description illustrates is representative method utilizing an azaindoline P2 component.

HCl Solution in dioxane (4M, 5 ml) was added to a representative Boc-protected compound (0.125 mmol) and stirred for 2 hrs at RT. The reaction mixture was concentrated to dryness under vacuum and washed with MeOH (5 ml) three times. Resulting residue was dried well under vacuum and subjected to next reaction as it is. The residue obtained above, the respective anhydride moiety (0.125 mmol), and triethylamine (0.5 mmol) were added to anhydrous DCM (5 mL) and stirred for 16 hrs. The mixture was concentrated under vacuum to give the crude product which was purified on a C18 column using 10-50% MeOH in water to yield product as an off-white solid (40-60%).

Method C: General Method of Coupling Reaction Using HATU/DIPEA.

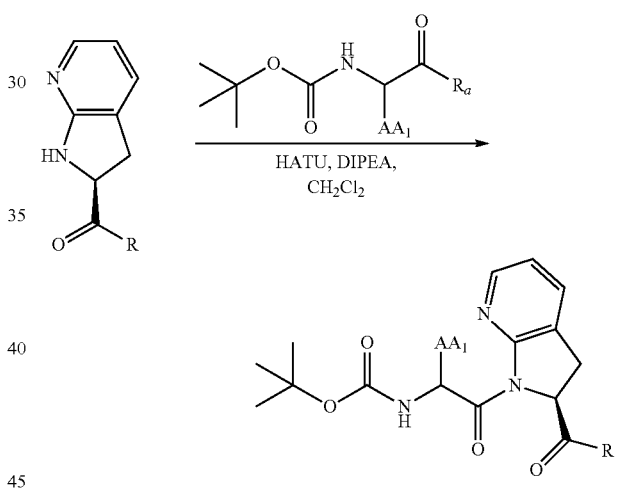

The above scheme and following description illustrates is representative method utilizing an azaindoline P2 component.

The respective acid moiety (0.125 mmol), HATU (0.17 mmol), DIPEA (0.5 mmol) and respective amine moiety (0.125 mmol) were stirred in anhydrous DCM (5 ml) for 16 hrs. The reaction mixture was concentrated under vacuum to give the crude product which was purified on a C18 column using 10-50% MeOH in water (or similar ratio as needed) to yield product as an off-white solid (35-55%).

Method D: General Method of Hydrolysis Using LiOH.

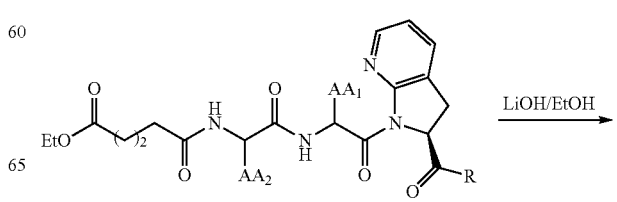

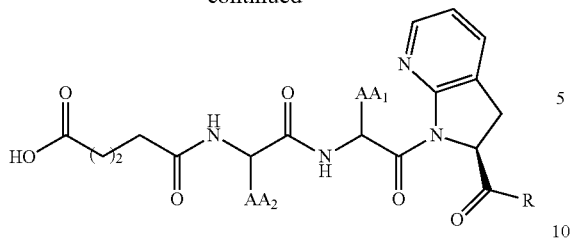

The above scheme and following description illustrates is representative method utilizing an azaindoline P2 component.

To the stirring solution of the ester compound (0.08 mmol) in ethanol (1 ml) was added solution of lithium hydroxide monohydrate (0.4 mmol) in water (0.5 ml). After stirring the reaction mixture for 5 hrs at RT, the mixture was acidified using citric acid (saturated solution) and concentrated under vacuum to give the crude product which was purified on a C18 column using 10-40% MeOH in water to yield product as an off-white solid (50-65%).

Method E: General Method for Boc Deprotection.

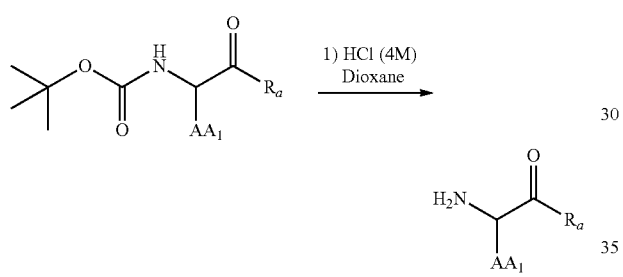

HCl Solution in dioxane (4M, 0.5 ml) was added to the respective carbamate compound (0.06 mmol) and stirred for 3 hrs at RT. The reaction mixture was concentrated under vacuum to give the crude product which was purified on a C18 column using 10-40% MeOH in water to yield product as an off-white solid (50-60%).

Method F: General Method for Hydrogenative Deprotection of Benzyl Esters or Benzyl carbamates.

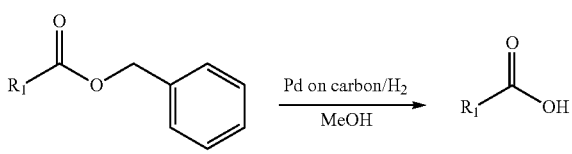

To a flask containing the respective benzylated compound (1.0 eq.) under a nitrogen atmosphere was added palladium on carbon (10 wt %, wetted, 0.2 eq.) then MeOH (0.05 M). The atmosphere was changed to hydrogen (vacuum+$H_2$ backfill×3) and the suspension of black solids was stirred for 3 hrs, then filtered over a pad of CELITE™ and washed with excess MeOH. The reaction mixture was concentrated under vacuum to give the crude product which was purified on a C18 column using 10-50% MeOH in water to yield the product (50-95%).

The following examples are provided for the purpose of illustrating, not limiting, the invention.

EXAMPLES

Synthetic Intermediates

The following is a description of synthetic intermediates (I-1 to I-10) useful for making representative compounds of the invention.

Intermediate I-1

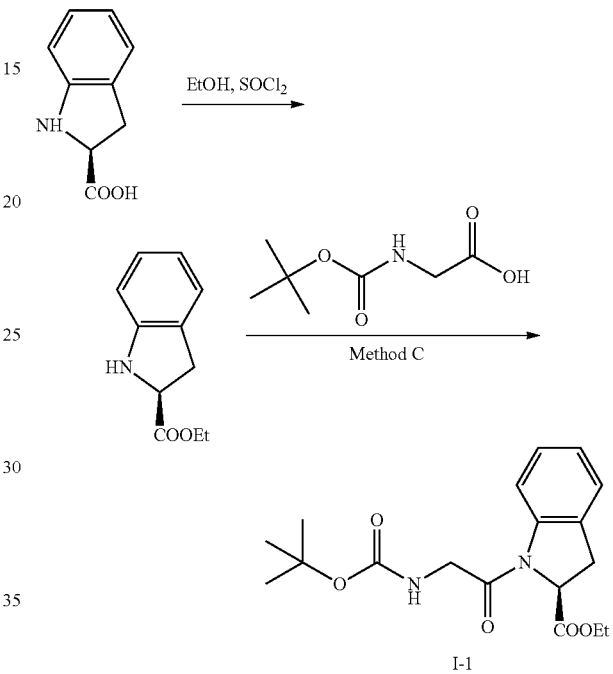

Ethyl(2S)-1-(2-{[(tert-butoxy)carbonyl]amino}acetyl)-2,3-dihydro-1H-indole-2-carboxylate (I-1)

(2S)-2,3-dihydro-1H-indole-2-carboxylic acid (500 mg, 306 mmol) was suspended in EtOH (5 mL) at 0° C. and thionyl chloride (0.45 mL, 6.13 mmol, 2 eq.) was added. The resulting clear mixture was allowed to come to RT and stirred for 16 hours. The reaction mixture was then concentrated to dryness and swapped with EtOH (2×10 mL). The solid obtained was dried well under reduced pressure to give ethyl(2S)-2,3-dihydro-1H-indole-2-carboxylate hydrochloride as a light brown solid (0.58 g, quantitative). $^1$H NMR (400 MHz, DMSO-d6) δ 1.18 (3H, s), 3.10-3.18 (1H, m), 3.30-3.40 (1H, m), 4.05-4.17 (2H, m), 4.55 (1H, bs), 6.80 (2H, bs), 7.02-7.08 (2H, m), 7.7 (2H, bs). Compound was used further as described.

I-1 was prepared from ethyl(2S)-2,3-dihydro-1H-indole-2-carboxylate hydrochloride and 2-((tert-butoxycarbonyl)amino)acetic acid using method C however the purification was performed on normal phase using 0% to 50% ethyl acetate in hexanes as the eluent. $^1$H NMR (400 MHz, DMSO-d6) δ1.18 (3H, t, J=6 Hz), 1.38 (9H, s), 3.19 (1H, d, J=16 Hz), 3.48-3.62 (2H, m), 3.95-4.20 (3H, m), 5.35 (1H, d, J=11 Hz), 7.00 (2H, t, J=8 Hz), 7.15-7.25 (2H, m), 8.01 (1H, d, J=8 Hz), MS (LC/MS) m/z 370.95 [M+Na]

Intermediate I-2

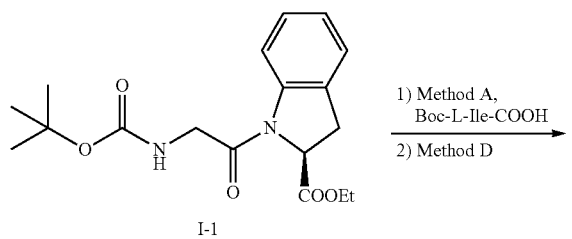

(2S)-1-[2-((2S,3S)-2-tert-Butoxycarbonylamino-3-methyl-pentanoylamino)-acetyl]-2,3-dihydro-1H-indole-2-carboxylic acid (I-2)

(2S)-Ethyl 1-(2-((2S,3S)-2-((tert-butoxycarbonyl)amino)-3-methylpentanamido)acetyl)indoline-2-carboxylate was prepared from I-1 and Boc-L-isoleucine using method A. MS (LC/MS) m/z observed 461.98, expected 462.26 [M+H]. Compound was confirmed using LC/MS and moved to next step as it was.

(2S)-1-[2-((2S,3S)-2-tert-Butoxycarbonylamino-3-methyl-pentanoylamino)-acetyl]-2,3-dihydro-1H-indole-2-carboxylic acid (I-2) was prepared from (2S)-1-[2-((2S,3S)-2-tert-butoxycarbonylamino-3-methyl-pentanoylamino)-acetyl]-2,3-dihydro-1H-indole-2-carboxylic acid ethyl ester using method D with 2 eq. of LiOH H$_2$O. MS (LC/MS) m/z observed 433.96, expected 434.23 [M+H]. Compound was confirmed using LC/MS and moved to next step as it was.

Intermediate I-3

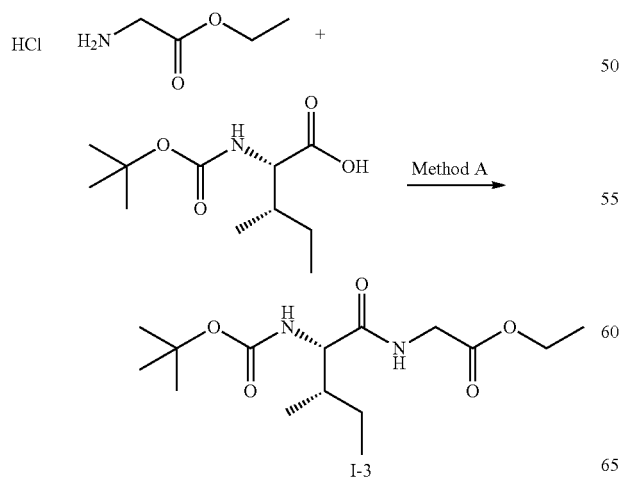

Ethyl 2-((2S,3S)-2-((tert-butoxycarbonyl)amino)-3-methylpentanamido)acetate (I-3)

I-3 was prepared from Boc-L-Isoleucine and Glycine ethyl ester hydrochloride using method A but the purification was performed on normal phase using 0% to 30% ethyl acetate in hexanes as the eluent. $^1$H NMR (400 MHz, CDCl$_3$) δ 0.91 (3H, t, J=7 Hz), 0.96 (3H, d, J=7 Hz), 1.14 (1H, m), 1.28 (3H, t, J=7 Hz), 1.45 (9H, s), 1.51 (1H, m), 1.92 (1H, m), 3.95-4.12 (3H, m), 4.22 (2H, q, J=7 Hz), 5.55 (1H, d, J=9 Hz), 6.52 (1H, bs), MS (LC/MS) m/z observed 317.42, expected 317.21 [M+H].

Intermediate I-4

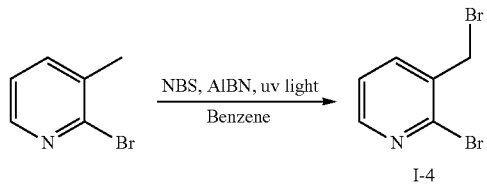

2-Bromo-3-(bromomethyl)pyridine (I-4)

This intermediate was generated by a modified procedure based on that disclosed in Rebek, J., et al., *J. Am. Chem. Soc.*, 107, 7487 (1985)). A three-neck round bottom flask with a stir bar was flame dried, cooled under vacuum and purged with N$_2$. To the flask were added 2-bromo-3-methylpyridine (5.2 mL, 29.1 mmol), N-bromosuccinimide (5.5 g, 32.0 mmol), and degassed benzene (126 mL). The flask was fitted with a condenser, heated to 40° C. and AIBN (0.24 g, 1.5 mmol) was added in several portions. The reaction was irradiated using a sun lamp as it was stirred at 40° C. The reaction was monitored using TLC and HPLC and was stopped after 80% conversion of the pyridine reagent (approximately 8 hrs). The reaction was concentrated under reduced pressure, then redissolved in DCM/EtOAc (120 mL, 4:1 (v/v)) and extracted once with 50 mL of NaHCO$_3$ (sat'd, aqueous), water and brine. The organic phase was dried over anhydrous sodium sulphate, filtered and concentrated. Upon standing the residue could not be fully redissolved in DCM and the resultant suspension was filtered to remove the insoluble solid. The filtrate was concentrated to near dryness and the residue was purified by normal phase flash chromatography (EtOAc/Hexanes) to give the title compound 1-4 (3.0 g, 11.9 mmol, 41%) as a yellow solid. $^1$H NMR (400 MHz, CDCl$_3$) δ 8.33 (1H, dd, J=5.2 Hz), 7.78 (1H, dd, J=7.2 Hz), 7.28 (1H, dd, J=5.4 Hz), 4.57 (2H, s), MS (LC/MS) m/z observed 249.97, expected 249.89 [M+H]

Intermediate I-5

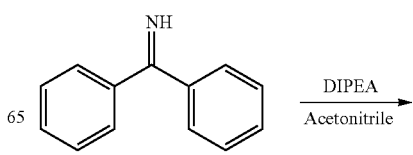

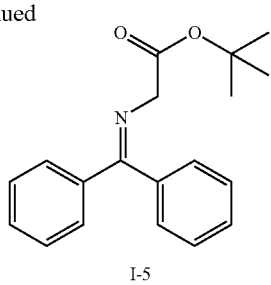

tert-Butyl 2-((diphenylmethylene)amino)acetate (I-5)

This intermediate was generated by a generic procedure based on that disclosed in US2010/0189644 and O'Donnell, *Acc. Chem. Res.*, 37, 506 (2004). A round bottom flask was charged with a stir-bar, diphenylmethanimine (8.6 g, 47.5 mmol), tert-butyl 2-bromoacetate (9.3 g, 47.5 mmol), and acetonitrile (40 mL). The reaction was heated to 70° C. and DIPEA (8.3 mL, 47.5 mmol) was added slowly. The flask was fitted with a reflux condenser and heated at 70° C. for 16 hrs. Analysis of the reaction by HPLC and TLC showed complete conversion of the reactants and the reaction was cooled to room temperature. A solution of 5:3 water/formic acid (1 mL) was added the reaction was concentrated under reduced pressure. The resultant solid was filtered and washed 2×60 mL of a cold solution of water/ethanol (3:3 (v/v)) and once with 30 mL of a cold solution of water/ethanol (1:1 (v/v)). The solid was dried under high vacuum to give tert-butyl 2-((diphenylmethylene)amino)acetate (I-5) as a white solid (14.9 g, 47.0 mmol, 99%). $^1$H NMR (400 MHz, CDCl$_3$) δ 7.66 (2H, m), 7.47 (3H, m), 7.41 (1H, t, J=8 Hz), 7.34 (1H, t, J=8 Hz), 7.20 (2H, m), 4.13 (2H, s), 1.48 (9H, s), MS (LC/MS) m/z observed 295.93, expected 296.16 [M+H].

Intermediate I-6

(1S,2S,4S,5R)-1-(Anthracen-9-ylmethyl)-2-(hydroxy(quinolin-4-yl)methyl)-5-vinylquinuclidin-1-ium chloride (I-6)

This intermediate was generated by a procedure based on that disclosed in Corey, E. J., et al., *J. Am. Chem. Soc.*, 119, 12414 (1997). A round bottom flask was charged with a stir-bar, quinolin-4-yl((1S,2S,4S,5R)-5-vinylquinuclidin-2-yl)methanol (1.5 g, 5.10 mmol) also known as cinchonine, 9-(chloromethyl)anthracene (1.21 g, 5.35 mmol) and toluene (15 mL). The flask was fitted with a condenser and heated for 2 hrs at 110° C. Conversion of the amine was confirmed by LCMS and the reaction was cooled to room temperature and poured into 100 mL of diethyl ether. The formed yellow precipitate was filtered and washed with 2×10 mL of cold DCM. The solid was set aside and the filtrate was concentrated and suspended overnight in 10% Et$_2$O/DCM at 0° C. The cold suspension was filtered. The solids were pooled together and dried on high vacuum to give the title compound (1S,2S,4S,5R)-1-(anthracen-9-ylmethyl)-2-(hydroxy(quinolin-4-yl)methyl)-5-vinylquinuclidin-1-ium chloride (I-6) as a bright yellow solid (2.6 g, 5.0 mmol, 98%). $^1$H NMR (400 MHz, CDCl$_3$) δ 9.06 (1H, d, J=8 Hz), 8.84 (2H, d, J=4 Hz), 8.73 (1H, d, J=8 Hz), 8.20 (1H, d, J=4 Hz), 8.03 (1H, d, J=4 Hz), 7.99 (1H, s), 7.70-7.55 (3H, m), 7.40 (1H, d, J=8 Hz), 7.30-7.15 (6H, m), 7.15-7.05 (2H, m), 6.83 (1H, t, J=14 Hz), 6.68 (1H, t, J=14 Hz), 5.44 (1H, m), 4.91 (1H, dd, J=10.4 Hz), 4.74 (2H, m), 6.83 (1H, d, J=14 Hz), 6.68 (1H, d, J=14 Hz), 5.44 (1H, m), 5.27 (1H, d, J=16 Hz), 6.68 (1H, dd, J=8.3 Hz), 4.74 (2H, m), 2.59 (1H, dd, J=14.12 Hz), 2.42 (1H, m), 2.36 (2H, s), 2.13 (1H, m), 1.90-1.75 (3H, m), 1.70 (1H, m), 2.42 (1H, m), 1.12 (1H, m), 1.01 (1H, m), MS (LC/MS) m/z observed 485.08, expected 485.26 [M−Cl].

Intermediate I-7

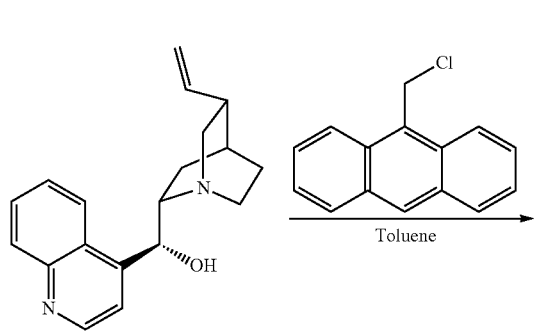

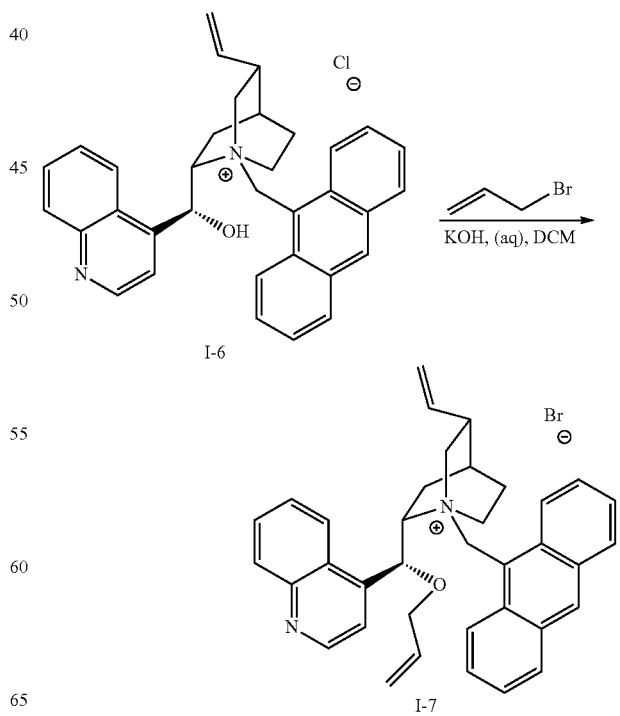

(1S,2S,4S,5R)-2-((Allyloxy)(quinolin-4-yl)methyl)-1-(anthracen-9-ylmethyl)-5-vinylquinuclidin-1-ium bromide (I-7)

This catalyst was generated by a procedure based on that disclosed in Corey, E. J., et al., *J. Am. Chem. Soc.*, 119, 12414 (1997). A round bottom flask with a stir bar was flame dried, cooled under vacuum and purged with $N_2$. To the flask were added 1-6 (1.0 g, 1.92 mmol), allyl bromide (0.5 mL 5.76 mmol) and DCM (8 mL). To the yellow foamy mixture was added a solution of 50% w/w KOH (2 mL, 9.60 mmol) at RT. A slight exotherm was observed. Analysis of the reaction by HPLC after 4 hrs showed complete conversion of I-6 and the reaction was diluted with 30 mL of DCM and water and transferred to a separatory funnel. The organic phase was collected, then extracted 2×20 mL of water and washed with NaCl (sat'd, aqueous). The organic phase was dried over anhydrous sodium sulphate, filtered and concentrated. To the residue was added 8 mL of methanol, which produced a clear red solution with a small amount of precipitate. Diethyl ether was slowly added to the solution at 0° C. and the solution became cloudy. After the addition of 50 mL of ether the precipitate was filtered, washed once with cold ether (10 mL) and dried under high vacuum to give the title compound (1S,2S,4S,5R)-2-((allyloxy)(quinolin-4-yl)methyl)-1-(anthracen-9-ylmethyl)-5-vinylquinuclidin-1-ium bromide (1-7) (0.63 g, 1.03 mmol, 54%). MS (LC/MS) m/z observed 525.08, expected 525.29 [M+H]. Compound was confirmed using LC/MS and moved to next step as it was.

Intermediate I-8

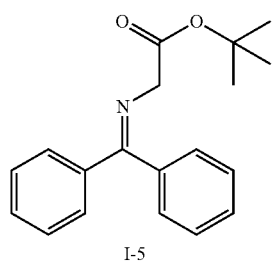

I-5

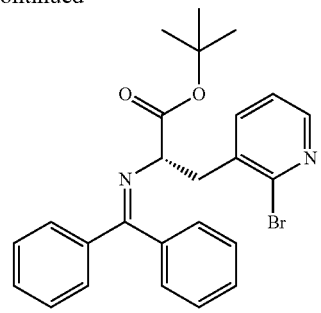

I-8

(S)-tert-Butyl 3-(2-bromopyridin-3-yl)-2-((diphenylmethylene)amino) propanoate (I-8)

This intermediate was generated by a modified procedure based on that disclosed in Viswanathan, R., et al., *J. Am. Chem. Soc.*, 125, 163 (2003) and *Synthesis* 2, 330 (2005). A three neck round bottom flask with a stir bar was charged with 1-5 (40.1 g, 135.7 mmol), 1-7 (8.2 g, 13.6 mmol), powdered KOH (69.1 g, 1221.4 mmol), and DCM (600 mL). The opaque yellow suspension was cooled to −78° C. and the flask fitted with a dropping funnel. A suspension of I-4 (152.0 g, 610.7 mmol) in 400 mL DCM was transferred to the dropping funnel and added to the reaction at −78° C. over about 1 hr. The suspension in the dropping funnel would occasionally settle and the solid would be resuspended. After the end of the addition the funnel was rinsed with an additional 200 mL of DCM and the rinse was added to the reaction. After 10 hrs at −78° C. the reaction was allowed to stir overnight as it warmed to room temperature. Analysis of the reaction by HPLC and TLC showed complete conversion of I-4. The reaction was diluted with 3 L of DCM, transferred to a 15 L reactor and extracted 2×1 L of water. During the separation the organic phase appeared cloudy due to a solid formed from I-4. The organic phase was collected, then washed with NaCl (sat'd, aqueous), dried over anhydrous sodium sulphate, filtered and concentrated to near dryness and purified by normal phase flash chromatography. A three solvent mobile phase was used for the separation; initially DCM/hexanes to elute the excess I-4, followed by EtOAc/Hexanes to elute the title compound (S)-tert-butyl 3-(2-bromopyridin-3-yl)-2-((diphenylmethylene)amino) propanoate (1-8) obtained as a yellow solid (23.1 g, 226.0 mmol, 37%). $^1$H NMR (400 MHz, CDCl$_3$) δ 8.20 (1H, dd, J=4.2 Hz), 7.60 (2H, d, J=8 Hz), 7.56 (1H, dd, J=4.2 Hz), 7.45-7.25 (6H, m), 7.12 (1H, dd, J=8.4 Hz), 6.67 (1H, d, J=d Hz), 4.39 (1H, dd, J=8.4 Hz), 3.39 (1H, dd, J=12.4 Hz), 3.21 (1H, dd, J=12.4 Hz), 1.46 (9H, s), MS (LC/MS) m/z observed 464.87, expected 465.12 [M+H].

Intermediate I-9

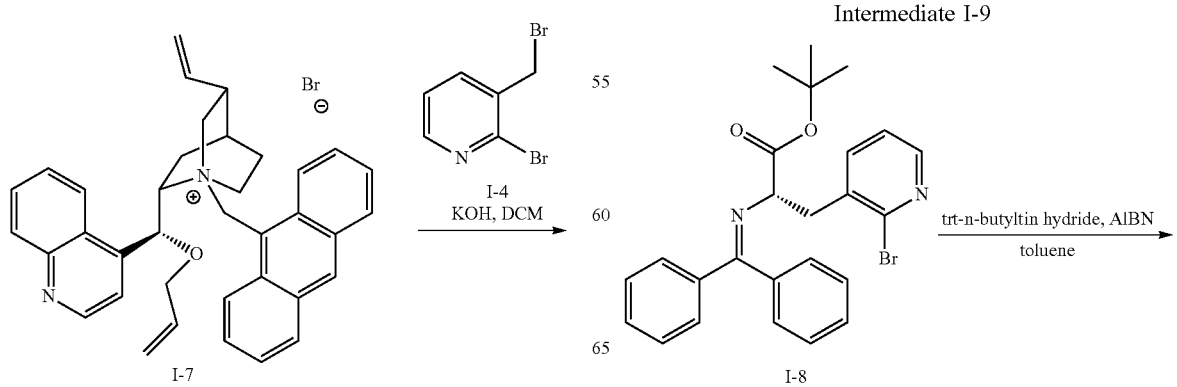

49

-continued

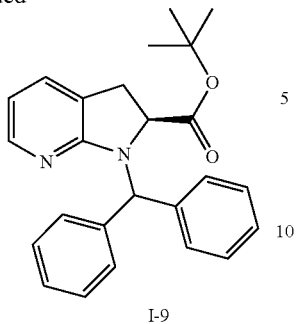

I-9

(S)-tert-Butyl 1-benzhydryl-2,3-dihydro-1H-pyrrolo[2,3-b]pyridine-2-carboxylate (I-9)

This intermediate was generated by a modified procedure based on that disclosed in Viswanathan, R., et al., *J. Am. Chem. Soc.*, 125, 163 (2003) and *Synthesis* 2, 330 (2005). A three-neck round bottom flask with a stir bar was flame dried, cooled under vacuum and purged with $N_2$. To the flask were added 1-8 (3.0 g, 6.46 mmol), tri-n-butyltin hydride (3.8 mL, 14.2 mmol), and degassed toluene (646 mL). The flask was fitted with a condenser, and a dropping funnel and heated to 85° C. A solution of AIBN (1.27 g, 7.8 mmol) in 40 mL toluene was prepared in the dropping funnel and added to the reaction over the course of 1 hr. After 2 hrs the reaction was monitored by LC/MS and approximately 50% conversion. Another portion of tri-n-butyltin hydride was added and the reaction was heated at 85° C. for another 4 hrs. Analysis of the reaction by TLC, HPLC and LC/MS showed complete conversion of I-8. The reaction was concentrated to near dryness and to the residue was added 250 mL of diethyl ether and 100 mL of a KF (sat'd, aqueous). The biphasic mixture was stirred vigorously at room temperature for 3 hrs during with time a white solid formed at the interface and on the flask wall. The mixture was filtered through CELITE™ and the cake washed with 200 mL of diethyl ether. The filtrate was transferred to a separatory funnel, the organic phase was collected, dried over anhydrous sodium sulphate, filtered and concentrated to near dryness. The residue was purified by normal phase flash chromatography (EtOAc/Hexanes) to give the title compound 1-9 as an off-white solid (1.37 g, 3.5 mmol, 55%). $^1$H NMR (400 MHz, CDCl$_3$) δ 7.87 (1H, d, J=4 Hz), 7.41 (2H, d, J=8 Hz), 7.35-7.15 (8H, m), 6.55-6.45 (2H, m), 4.21 (1H, dd, J=10.6 Hz), 3.43 (1H, dd, J=18.10 Hz), 3.21 (1H, dd, J=18.6 Hz), 1.73 (9H, s), MS (LC/MS) m/z observed 487.04, expected 487.21 [M+H].

Intermediate I-10

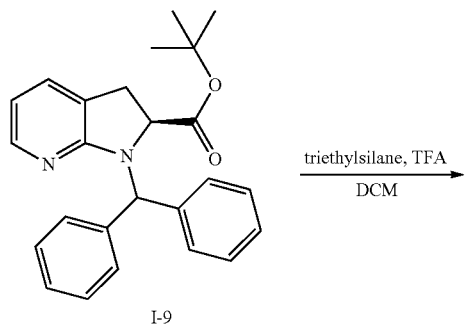

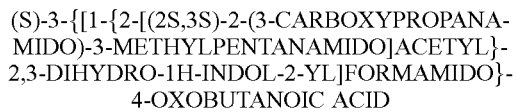

I-9

50

-continued

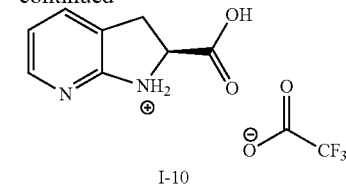

I-10

(2S)-2-Carboxy-2,3-dihydro-1H-pyrrolo[2,3-b]pyridin-1-ium (I-10)

This intermediate was generated by a modified procedure based on that disclosed in Viswanathan, R., et al., *J. Am. Chem. Soc.*, 125, 163 (2003) and *Synthesis* 2, 330 (2005). A round bottom flask was charged with 1-9 (670 mg, 1.7 mmol), DCM (5 mL) and triethylsilane (1 mL, 8.65 mmol). To the clear yellow solution was added TFA (3.3 mL) at room temperature and the yellow/orange reaction was stirred at room temperature for 16 hrs. Analysis of the reaction by HPLC showed complete conversion of I-9 and the reaction was concentrated to approximately one quarter of the volume. Diethyl ether (60 mL) was added slowly to the residue, which resulted in the precipitation of a fine white solid. The mixture was cooled to 0° C. for 10 min then sonicated and filtered. The white solid was washed with 10 mL of cold diethyl ether to give (2S)-2-carboxy-2,3-dihydro-1H-pyrrolo[2,3-b]pyridin-1-ium trifluoroacetate (I-10) (263 mg, 0.93 mmol, 54%). $^1$H NMR (400 MHz, DMSO) δ 8.52 (1H, bs), 7.69 (1H, d, J=4 Hz), 7.55 (1H, d, J=4 Hz), 6.68 (2H, dd, J=8.4 Hz), 4.59 (1H, dd, J=12.4 Hz), 3.45 (1H, dd, J=16.12 Hz), 3.15 (1H, dd, J=20.4 Hz), MS (LC/MS) m/z observed 165.02, expected 165.07 [M-Cl].

Representative Granzyme B Inhibitor Compounds

The following is a description of the preparation of representative Granzyme B inhibitor compounds of the invention.

Examples C1-C8 were prepared by the representative synthetic pathway illustrated schematically in FIG. 3.

Example C1

(S)-3-{[1-{2-[(2S,3S)-2-(3-CARBOXYPROPANAMIDO)-3-METHYLPENTANAMIDO]ACETYL}-2,3-DIHYDRO-1H-INDOL-2-YL]FORMAMIDO}-4-OXOBUTANOIC ACID

A solution of DMSO (0.52 mL, 7.27 mmol) in DCM (20 ml) was cooled to −78° C. To this solution was added oxalyl chloride (0.3 ml, 3.63 mmol) and stirred for 20 min. at −78° C. Solution of (S)-tert-butyl 3-((tert-butoxycarbonyl)amino)-4-hydroxybutanoate (0.5 gm, 1.82 mmol) in DCM (8 ml) was added and stirred for 30 min. at −78° C. Solution of triethylamine (1.2 mL, 8.72 mmol) in DCM (5 ml) was added and stirred for 10 min. at −78° C. Diethyl ether (40 ml) was added and the reaction mixture warmed to RT. The resulting reaction mixture washed with sodium bisulfate (sat'd aqueous) and with brine. Separated organic layer was dried over anhydrous $Na_2SO_4$, filtered and concentrated in vacuo. Flash chromatography (EtOAc: Hexane 0-30%) afforded (S)-tert-butyl 3-((tert-butoxycarbonyl)amino)-4-oxobutanoate (0.4 g, 79.5%) as a pale yellow oil. $^1$H NMR (400 MHz, Chloroform-d) δ 1.44 (9H, s), 1.47 (9H, s), 2.71-2.77 (1H, dd, J=16, 4 Hz), 2.89-2.94 (1H, dd, J=16, 4 Hz), 4.31-4.35 (1H, m), 5.59-5.61 (1H, d, J=8 Hz), 9.65 (1H, s).

HCl solution in dioxane (4 M, 4 ml) was added to (S)-tert-butyl 3-((tert-butoxycarbonyl)amino)-4-oxobutanoate (0.20 g, 0.7326 mmol) and stirred for 2 hrs at RT. EtOH (4 ml) was added and the reaction mixture stirred further for 1 hr. The reaction mixture was concentrated to dryness under vacuum and swapped with EtOH (4 ml) three times. The resulting residue was dried well under vacuum and subjected to next reaction as it is. The residue obtained above, 1-2 (0.32 gm, 0.7326 mmol), EDC (0.24 gm, 1.25 mmol), HOBt (0.17 gm, 1.1 mmol) and DIPEA (0.51 ml, 2.9 mmol) were all stirred in anhydrous DMF (15 ml) for 16 hrs. The reaction mixture was concentrated under vacuum to give the crude product which was purified on a C18 column using 10-50% MeOH in water to yield 3-(S)-({1-[2-(S)-(2-tert-butoxycarbonylamino-3-(S)-methyl-pentanoylamino)-acetyl]-2,3-dihydro-1H-indole-2-(S)-carbonyl}-amino)-4-oxo-butyric acid tert-butyl ester as an off-white solid 0.13 g (30%). MS (LC/MS) m/z observed 589.08, expected 589.32 [M+H]. Compound was confirmed using LC/MS and moved to next step as it was.

3-(S)-[(1-{2-[2-(S)-(3-Carboxy-propionylamino)-3-(S)-methyl-pentanoylamino]-acetyl}-2,3-dihydro-1H-indole-2-(S)-carbonyl)-amino]-4-oxo-butyric acid tert-butyl ester was prepared from 3-(S)-({1-[2-(S)-(2-tert-butoxycarbonylamino-3-(S)-methyl-pentanoylamino)-acetyl]-2,3-dihydro-1H-indole-2-(S)-carbonyl}-amino)-4-oxo-butyric acid tert-butyl ester and succinic anhydride using method B. MS (LC/MS) m/z observed 589.14, expected 589.65 [M+H]. Compound was confirmed using LC/MS and moved to next step as is.

A solution of compound 3-(S)-({1-[2-(S)-(2-tert-butoxycarbonylamino-3-(S)-methyl-pentanoylamino)-acetyl]-2,3-dihydro-1H-indole-2-(S)-carbonyl}-amino)-4-oxo-butyric acid tert-butyl ester (0.07 g, 0.119 mmol) in DCM (2 ml) was cooled to 0° C. To this solution was added TFA (2 ml). Reaction mixture was warmed to RT and stirred for 30 min. The reaction mixture was concentrated to dryness and dried well under vacuum and subjected to next reaction as it was. The residue obtained above was dissolved in EtOH (1 ml) and solution of LiOH H$_2$O (0.05 gm, 1.19 mmol) in water (0.5 ml) was added and stirred for 1 hr. The reaction mixture was concentrated under vacuum to give the crude product which was purified on a C18 column using 10-60% MeOH in water to yield title compound (S)-3-{[1-{2-[(2S,3S)-2-(3-carboxypropanamido)-3-methylpentanamido]acetyl}-2,3-dihydro-1H-indol-2-yl]formamido}-4-oxobutanoic acid (C1) as an off-white solid 0.02 g (32%). $^1$H NMR (400 MHz, DMSO-d6) δ 0.80-0.84 (3H, t, J=8 Hz), 0.86-0.88 (3H, d, J=8 Hz), 1.08-1.15 (1H, m), 1.43-1.49 (1H, m), 1.72-1.78 (1H, m), 2.37-2.46 (4H, m), 3.06-3.10 (2H, d, J=16 Hz), 3.57-3.64 (2H, m), 4.06-4.14 (2H, t, J=16 Hz), 4.23-4.28 (2H, m), 5.09-5.14 (1H, m), 6.99-7.03 (1H, t, J=8 Hz), 7.16-7.24 (2H, m), 7.90-7.93 (1H, d, J=12 Hz), 8.03-8.05 (1H, d, J=8 Hz), 8.17 (1H, s), 8.89 (1H, bs), 12.17 (2H, bs), MS (LC/MS) m/z observed 532.98, expected 533.22 [M–H].

Example C2

3-{[(2S)-1-(2-ACETAMIDOACETYL)-2,3-DIHYDRO-1H-INDOL-2-YL]FORMAMIDO}-4-OXOBUTANOIC ACID

I-1 (368 mg, 1.058 mmol) was dissolved in a HCl in dioxane solution (4 M, 15 mL) at RT and was left under stirring for 2 hrs. The reaction mixture was then concentrated to dryness and swapped with EtOH (2×10 mL). The solid obtained was dried well under vacuum to get a brown solid (300 mg, quantitative), which was suspended in anhydrous DCM (10 mL). DIPEA (551 mL, 3.162 mmol) was then added and the solution became clear. Acetyl chloride (71 mL, 1.58 mmol) was then added slowly to the reaction mixture at RT, which was stirred for 10 minutes and then quenched with MeOH (1 mL). The solvent was then evaporated to dryness and the residue was hydrolyzed following method D to give (S)-1-(2-acetamidoacetyl)indoline-2-carboxylic acid as an off white solid (275 mg, quantitative). MS (LC/MS) m/z observed 262.89, expected 263.27 [M+H]. Compound was confirmed using LC/MS and moved to next step as it was.

(S)-tert-Butyl 3-((tert-butoxycarbonyl)amino)-4-oxobutanoate (1.73 g, 2.12 mmol) was dissolved in HCl in dioxane (4M, 25 mL) at RT and the reaction was left under stirring for 3 hrs. EtOH (10 mL) was then added to the reaction mixture, which was stirred at RT for 2 additional hrs. The reaction mixture was then concentrated and swapped with EtOH (10 mL) twice to yield a mixture of 4-ethoxy-1,4-dioxobutan-2-aminium chloride (aldehyde) and 1,4-diethoxy-4-oxobut-1-en-2-aminium chloride (enol ether) as an orange oil (1.14 g, quantitative). MS (LC/MS) m/z observed 146.00, expected 146.08 [M+H] for the aldehyde and m/z observed 174.05, expected 174.22 [M+H] for the enol ether. The mixture was confirmed using LC/MS and moved to next step as they were.

The mixture (S)-3-{[1-(2-acetylamino-acetyl)-2,3-dihydro-1H-indole-2-carbonyl]-amino}-4-oxo-butyric acid ethyl ester and (S)-3-{[1-(2-acetylamino-acetyl)-2,3-dihydro-1H-indole-2-carbonyl]-amino}-4-ethoxy-but-3-enoic acid ethyl ester was prepared from (S)-1-(2-acetamidoacetyl)indoline-2-carboxylic acid and the mixture of 4-ethoxy-1,4-dioxobutan-2-aminium chloride and 1,4-diethoxy-4-oxobut-1-en-2-aminium chloride using method A in DMF but without HCl treatment. This gave the mixture (S)-3-{[1-(2-acetylamino-acetyl)-2,3-dihydro-1H-indole-2-carbonyl]-amino}-4-oxo-butyric acid ethyl ester (aldehyde) and (S)-3-{[1-(2-acetylamino-acetyl)-2,3-dihydro-1H-indole-2-carbonyl]-amino}-4-ethoxy-but-3-enoic acid ethyl ester (enol ether) as a yellow oil. MS (LC/MS) m/z observed 389.95, expected 390.17 [M+H] for the aldehyde and m/z observed 418.03, expected 418.20 [M+H] for the enol ether. The mixture was confirmed using LC/MS and moved to next step as it was.

The mixture of (S)-3-{[1-(2-acetylamino-acetyl)-2,3-dihydro-1H-indole-2-carbonyl]-amino}-4-oxo-butyric acid ethyl ester and (S)-3-{[1-(2-acetylamino-acetyl)-2,3-dihydro-1H-indole-2-carbonyl]-amino}-4-ethoxy-but-3-enoic acid ethyl ester (180 mg) was dissolved in DCM (5 mL) and cooled to 0° C. TFA (5 mL) was then added and the reaction was stirred at 0° C. for 5 minutes and then allowed to warm up to RT and stirred for an additional two hrs. All enol ether was converted to the aldehyde. The reaction mixture was then concentrated and the residue was dissolved in dioxane (10 mL) and lithium hydroxide (0.5 M, aqueous) was added until a pH of 7 was seen by pH paper. The reaction was left for 15 minutes and then acidified with citric acid (sat'd, aqueous) to pH 4. The solvents were then evaporated and the product was purified on a C18 column using 15-30% MeOH in water to yield title compound 3-{[(2S)-1-(2-acetamidoacetyl)-2,3-dihydro-1H-indol-2-yl]formamido}-4-oxobutanoic acid (C2) as an off-white solid (89 mg, 57%). $^1$H NMR (400 MHz, DMSO-d6) δ 1.89 (3H, s), 2.80-3.12 (2H, m), 3.35 (1H, m), 3.51-3.68 (2H, m), 4.05-4.28 (2H, m), 5.10 (1H, m), 7.01 (1H, t, J=7 Hz), 7.14-7-26 (2H, m), 8.03 (1H, d, J=8 Hz), 8.18 (1H, bs), 8.90 (1H, bs), MS (LC/MS) m/z observed 361.93, expected 362.14 [M+H]

Example C3

(S)-3-{[1-{2-(S)-[(2S,3S)-2-ACETAMIDO-3-METHYLPENTANAMIDO]ACETYL}-2,3-DI-HYDRO-1H-INDOL-2-YL]FORMAMIDO}-4-OXOBUTANOIC ACID

I-2 (300 mg, 0.65 mmol) was dissolved in a HCl in dioxane solution (4 M, 15 mL) at RT and was left under stirring for 2 hrs. The reaction mixture was then concentrated to dryness and swapped with EtOH (2×10 mL). The solid obtained was dried well under vacuum to get a brown solid (258.6 mg, quantitative), which was suspended in anhydrous DCM (10 mL). DIPEA (339 mL, 1.95 mmol) was then added and the solution became clear. Acetyl chloride (69 mL, 0.975 mmol) was then added slowly to the reaction mixture at RT, which was stirred for 10 minutes and then quenched with MeOH (1 mL). The solvent was then evaporated to dryness and the residue was hydrolyzed following method D to give (S)-1-(2-((2S,3S)-2-acetamido-3-methylpentanamido)acetyl)indoline-2-carboxylic acid as an off white solid (244 mg, quantitative). MS (LC/MS) m/z observed 375.97, expected 376.19 [M+H]. Compound was confirmed using LC/MS and moved to next step as it was.

The mixture of (S)-3-({1-[2-((2S,3S)-2-acetylamino-3-methyl-pentanoylamino)-acetyl]-2,3-dihydro-1H-indole-2-carbonyl}-amino)-4-oxo-butyric acid ethyl ester and (S)-3-({1-[2-((2S,3S)-2-acetylamino-3-methyl-pentanoylamino)-acetyl]-2,3-dihydro-1H-indole-2-carbonyl}-amino)-4-ethoxy-but-3-enoic acid ethyl ester was prepared from (S)-1-(2-((2S,3S)-2-acetamido-3-methylpentanamido)acetyl) indoline-2-carboxylic acid and the mixture 4-ethoxy-1,4-dioxobutan-2-aminium chloride and 1,4-diethoxy-4-oxobut-1-en-2-aminium chloride (from Example C2) using method A in DMF but without HCl treatment. This gave a mixture as a yellow solid. MS (LC/MS) m/z observed 502.94, expected 503.25 [M+H] for the aldehyde and m/z observed 531.08, expected 531.28 [M+H] for the enol ether. Compounds were confirmed using LC/MS and moved to next step as they were.

The mixture (S)-3-({1-[2-((2S,3S)-2-acetylamino-3-methyl-pentanoylamino)-acetyl]-2,3-dihydro-1H-indole-2-carbonyl}-amino)-4-oxo-butyric acid ethyl ester and (S)-3-({1-[2-((2S,3S)-2-acetylamino-3-methyl-pentanoylamino)-acetyl]-2,3-dihydro-1H-indole-2-carbonyl}-amino)-4-ethoxy-but-3-enoic acid ethyl ester (164 mg) was dissolved in DCM (5 mL) and cooled to 0° C. TFA (5 mL) was then added and the reaction was stirred at 0° C. for 5 minutes and then allowed to warm up to RT and stirred for an additional two hrs. All enol ether was converted to the aldehyde. The reaction mixture was then concentrated and the residue was dissolved in dioxane (10 mL) and lithium hydroxide (0.5 M, aqueous) was added until a pH of 11 was seen by pH paper. The reaction was left for 15 minutes and then acidified with citric acid (sat'd, aqueous) to pH 4. The solvents were then evaporated and the product was purified on a C18 column using 15-50% MeOH in water to yield (S)-3-{[1-{2-(S)-[(2S,3S)-2-acetamido-3-methylpentanamido]acetyl}-2,3-dihydro-1H-indol-2-yl]formamido}-4-oxobutanoic acid (C3) as an off-white solid (39 mg, 26%). $^1$H NMR (400 MHz, DMSO-d6) δ 0.81 (3H, t, J=7.4 Hz), 0.87 (3H, d, J=7 Hz), 1.06-1.16 (1H, m), 1.45 (1H, m), 1.72 (1H, m), 1.87 (3H, s), 2.90-3.13 (2H, m), 3.35 (1H, m), 3.51-3.68 (2H, m), 4.05- 4.20 (2H, m), 4.25 (1H, m), 5.11 (1H, m), 7.01 (1H, t, J=7 Hz), 7.14-7.26 (2H, m), 7.92 (1H, d, J=8 Hz), 8.03 (1H, d, J=8 Hz), 8.25 (1H, m), 8.90 (1H, bs), MS (LC/MS) m/z observed 474.91, expected 475.22 [M+H].

Example C4

(S)-3-{[(2S)-1-{2-[(2S,3S)-3-METHYL-2-[2-(2H-1,2,3,4-TETRAZOL-5-YL)ACETAMIDO]PENTANAMIDO]ACETYL}-1H,2H,3H-PYRROLO[2,3-B]PYRIDIN-2-YL]FORMAMIDO}-4-OXOBUTANOIC ACID

Ethyl 2-((2S,3S)-2-(2-(1H-tetrazol-5-yl)acetamido)-3-methylpentanamido)acetate (620 mg, 1.64 mmol, 57%) was collected as an off-white solid from I-3 (0.91 g, 2.88 mmol) and 2-(2H-tetrazol-5-yl)acetic (307 mg, 2.4 mmol) using method A in DMF. MS (LC/MS) m/z observed 326.86, expected 327.18 [M+H]. Compound structure was confirmed using LC/MS and moved to next step as it was.

A round bottom flask was charged with a stir bar, Ethyl 2-((2S,3S)-2-(2-(1H-tetrazol-5-yl)acetamido)-3-methylpentanamido)acetate (290 mg, 0.89 mmol), LiOH (94 mg, 2.23 mmol), $^t$BuOH (6.6 ml), and water (3.3 mL). The reaction was stirred at RT for 2 hrs. Analysis of the reaction by LC/MS showed complete conversion and HCl (concentrated, aqueous) was added to reach pH 2. The reaction was concentrated under reduced pressure and reconcentrated from $^t$BuOH. 2-((2S,3S)-2-(2-(1H-Tetrazol-5-yl)acetamido)-3-methylpentanamido)acetic acid was collected as an off white solid. (MS (LC/MS) m/z observed 298.89, expected 299.15 [M+H]. Compound was confirmed using LC/MS and moved to next step as it was.

(S)-1-(2-((2S,3S)-2-(2-(1H-Tetrazol-5-yl)acetamido)-3-methylpentanamido)acetyl)-2,3-dihydro-1H-pyrrolo[2,3-b]pyridine-2-carboxylic acid (129 mg, 0.29 mmol, 46%) was prepared from I-10 (176 mg, 0.63 mmol) via method C with 3 eq. (1.9 mmol) of 2-((2S,3S)-2-(2-(1H-tetrazol-5-yl)acetamido)-3-methylpentanamido)acetic acid. MS (LC/MS) m/z observed 444.94, expected 445.19 [M+H]. Compound was confirmed using LC/MS and moved to next step as it was.

A round bottom flask was charged with a stir bar, (S)-tert-butyl 3-((tert-butoxycarbonyl)amino)-4-oxobutanoate (303 mg, 1.11 mmol, from Example C1) and HCl in dioxane (4 M, 4 mL). The reaction was stirred at room temperature for 1 hr then concentrated to near dryness. Another aliquot of HCl in dioxane (4 M, 2 mL) were added followed by allyl alcohol (1 mL). The reaction was stirred for 40 min at room temperature at which time the reaction changed from cloudy to clear. Analysis of the reaction by LC/MS showed complete conversion and the reaction was concentrated to dryness and reconcentrated twice from diethyl ether. The remaining solid contained the (E)-1,4-bis(allyloxy)-4-oxobut-1-en-2-aminium 2,2,2-trifluoroacetate in quantitative yield. MS (LC/MS) m/z observed 197.96, expected 198.11 [M-C1]. Compound was confirmed using LC/MS and moved to next step as it was.

4-Allyloxy-3-[(1-{2-(S)-[3-(S)-methyl-2-(2-2H-tetrazol-5-yl-acetylamino)-pentanoylamino]-acetyl}-2,3-dihydro-1H-pyrrolo[2,3-b]pyridine-2-(S)-carbonyl)-amino]-but-3-enoic acid allyl ester (15 mg, 0.03 mmol, 10%) was prepared from (S)-1-(2-((2S,3S)-2-(2-(2H-tetrazol-5-yl)acetamido)-3-methylpentanamido)acetyl)-2,3-dihydro-1H-pyrrolo[2,3-b]pyridine-2-carboxylic acid (129 mg, 0.29 mmol) via method A without HCl treatment, and with 3 eq. (0.87 mmol) of (E)-1,4-bis(allyloxy)-4-oxobut-1-en-2-aminium 2,2,2-trifluoroacetate. 4-Allyloxy-3-[(1-{2-(S)-[3-(S)- methyl-2-(2-2H-tetrazol-5-yl-acetylamino)-pentanoylamino]-acetyl}-2,3-dihydro-1H-pyrrolo[2,3-b]pyridine-2-(S)-carbonyl)-amino]-but-3-enoic acid allyl ester was purified by preparative HPLC, 10-70% MeOH/H₂O. During the purification, 3.5 mg of title compound (S)-3-{[(2S)-1-{2-[(2S,3S)-3-methyl-2-[2-(2H-1,2,3,4-tetrazol-5-yl)acetamido]pentanamido]acetyl}-1H,2H,3H-pyrrolo[2,3-b]pyridin-2-yl]formamido}-4-oxobutanoic acid (C4) was also formed and collected separately. MS (LC/MS) m/z observed 624.03, expected 623.28 [M+H]. Compound was confirmed using LC/MS and moved to next step as it was.

A round bottom flask was charged with a stir bar, 4-allyloxy-3-[(1-{2-(S)-[3-(S)-methyl-2-(2-2H-tetrazol-5-yl-acetylamino)-pentanoylamino]-acetyl}-2,3-dihydro-1H-pyrrolo[2,3-b]pyridine-2-(S)-carbonyl)-amino]-but-3-enoic acid allyl ester (15 mg, 0.03 mmol) and TFA (2 mL). The reaction was stirred at room temperature for 1 hr then concentrated to near dryness and reconcentrated twice from diethyl ether. The remaining solid contained desired compound in quantitative yield. MS (LC/MS) m/z observed 583.87, expected 584.26 [M+H]. Compound was confirmed using LC/MS and moved to next step as it was.

A round bottom flask was charged with a stir bar then purged with N₂ and 3-[(1-{2-[3-(S)-methyl-2-(S)-(2-2H-tetrazol-5-yl-acetylamino)-pentanoylamino]-acetyl}-2,3-dihydro-1H-pyrrolo[2,3-b]pyridine-2-(S)-carbonyl)-amino]-4-oxo-butyric acid allyl ester (18 mg, 0.037 mmol), Pd(PPh₃)₄ (2.6 mg, 0.0023 mmol), and DCM (6 mL) were added under N₂. Morpholine (3 mg, 0.039 mmol) was added and the reaction was stirred at RT for 90 min under N₂. Analysis of the reaction by LC/MS showed complete conversion of 3-[(1-{2-[3-(S)-methyl-2-(S)-(2-2H-tetrazol-5-yl-acetylamino)-pentanoylamino]-acetyl}-2,3-dihydro-1H-pyrrolo[2,3-b]pyridine-2-(S)-carbonyl)-amino]-4-oxo-butyric acid allyl ester and the reaction was acidified to pH 5 using formic acid. The reaction was concentrated and the residue was purified by preparative HPLC, 10-70% MeOH/H₂O. The title compound C4 (9.0 mg, 0.017 mmol, 44%) was collected as an off white solid. The ¹H NMR spectrum consistently did not show the aldehyde proton. ¹H NMR (400 MHz, DMSO-d6) δ 8.72 (1H, m), 8.45-8.35 (2H, m), 8.12 (1H, d, J=6 Hz), 7.62 (1H, d, J=6 Hz), 7.00 (1H, t, J=6 Hz), 4.90 (1H, m), 4.70 (1H, m), 4.45 (1H, dd, J=20.4 Hz), 4.28 (1H, m), 3.91 (2H, m), 3.45-3.38 (2H, m), 3.23 (1H, m), 2.98-2.80 (2H, m), 1.74 (1H, m), 1.46 (1H, m), 1.11 (1H, m), 0.86 (3H, d, J=4 Hz), 0.81 (3H, t, J=8 Hz), MS (LC/MS) m/z observed 543.94, expected 544.23 [M+H].

Example C5

(S)-4-(BENZYLCARBAMOYL)-3-{[(2S)-1-{2-[(2S,3S)-3-METHYL-2-[2-(2H-1,2,3,4-TETRAZOL-5-YL)ACETAMIDO]PENTANAMIDO]ACETYL}-2,3-DIHYDRO-1H-INDOL-2-YL]FORMAMIDO}-4-OXOBUTANOIC ACID

Z-L-aspartic acid β-methyl ester (2 g, 7.11 mmol, 1 eq.), EDC (1.77 g, 9.244 mmol, 1.3 eq.) and DMAP (86.9 mg, 0.711 mmol, 0.1 eq.) were combined in a round bottom flask. DCM (40 mL) was then added and within one minute (triphenylphosphoranylidene)acetonitrile (2.79 g, 9.24 mmol, 1.3 eq.) was added in one portion. The reaction was left at RT for 4 hrs and then successively washed with water (1×40 mL) and NaHCO₃ (sat'd, aqueous, 1×40 mL). The organic layer was dried over sodium sulphate and concentrated. The product was purified on normal phase using 0% to 50% ethyl acetate in hexanes as the eluent to give (S)-methyl 3-(((benzyloxy)carbonyl)amino)-5-cyano-4-oxo-5-(triphenylphosphoranylidene)pentanoate as a white foam (1.75 g, 44%). ¹H NMR (400 MHz, CDCl₃) δ 3.15 (1H, dd, J=5, 17 Hz), 3.53 (1H, dd, J=5, 17 Hz), 3.65 (3H, s), 5.12 (2H, s), 5.18 (1H, m), 5.84 (1H, d, J=7 Hz), 7.21-7.42 (20H, m), MS (LC/MS) m/z observed 564.94, expected 565.19 [M+H].

(S)-Methyl 3-(((benzyloxy)carbonyl)amino)-5-cyano-4-oxo-5-(triphenylphosphoranylidene)pentanoate (500 mg, 0.886 mmol, 1 eq.) was ozonized in dry DCM (15 mL) at -78° C. for 1 hour. The blue-green reaction mixture was then purged with O₂ for 10 min and N₂ for 10 min at -78° C. The mixture became yellow. A solution of BnNH₂ (0.145 mL, 1.328 mmol, 1.5 eq.) was added and the reaction was left at -78° C. for 1 hour and then allowed to warm up to RT. The solvent was then concentrated and the product was purified on normal phase using 0% to 35% ethyl acetate in hexanes as the eluent to give (S)-methyl 5-(benzylamino)-3-(((benzyloxy)carbonyl)amino)-4,5-dioxopentanoate as a greenish solid (126.8 mg, 36%). MS (LC/MS) m/z observed 399.05, expected 399.16 [M+H]. Compound was confirmed using LC/MS and moved to next step as it was.

(S)-Methyl 5-(benzylamino)-3-(((benzyloxy)carbonyl)amino)-4,5-dioxopentanoate (126.8 mg, 0.318 mmol) was dissolved in MeOH (20 mL) and treated with Pd/C (10% wt, 60 mg) under a hydrogen atmosphere for 6 hrs. The reaction mixture was then filtered over CELITE™ and the solids were washed with MeOH (3×15 mL). The filtrate and washings were concentrated to give (S)-methyl 3-amino-5-(benzylamino)-4,5-dioxopentanoate (56.7 mg, 68%) as a yellow solid. MS (LC/MS) m/z observed 265.66, expected 265.12 [M+H]. Compound was confirmed using LC/MS and moved to next step as it was.

(S)-4-(Benzylcarbamoyl)-3-{[(2S)-1-{2-[2-amino-(2S,3S)-3-methyl-pentano yl amino]acetyl}-2,3-dihydro-1H-indol-2-yl]formamido}-4-oxobutanoic acid methyl ester was prepared from (S)-methyl 3-amino-5-(benzylamino)-4,5-dioxopentanoate and 1-2 using method A but the purification was performed on normal phase using 10% to 95% ethyl acetate in hexanes as the eluent. MS (LC/MS) m/z observed 680.35, expected 680.33 [M+H]. Compound was confirmed using LC/MS and moved to next step as it was.

(S)-4-(Benzylcarbamoyl)-3-{[(2S)-1-{2-[(2S,3S)-3-methyl-2-[2-(2H-1,2,3,4-tetrazol-5-yl)acetamido]pentanamido]acetyl}-2,3-dihydro-1H-indol-2-yl]formamido}-4-oxobutanoic acid methyl ester was prepared from (S)-4-(benzylcarbamoyl)-3-{[(2S)-1-{2-[2-amino-(2S,3S)-3-methyl-pentanoylamino]acetyl}-2,3-dihydro-1H-indol-2-yl]formamido}-4-oxobutanoic acid methyl ester and 2-(2H-tetrazol-5-yl)acetic acid using method A but with DMF as solvent for the coupling reaction. MS (LC/MS) m/z observed 690.12, expected 690.30 [M+H]. Compound was confirmed using LC/MS and moved to next step as it was.

Title compound (S)-4-(benzylcarbamoyl)-3-{[(2S)-1-{2-[(2S,3S)-3-methyl-2-[2-(2H-1,2,3,4-tetrazol-5-yl)acetamido]pentanamido]acetyl}-2,3-dihydro-1H-indol-2-yl]formamido}-4-oxobutanoic acid (C5) was prepared from (S)-4-(benzylcarbamoyl)-3-{[(2S)-1-{2-[(2S,3S)-3-methyl-2-[2-(2H-1,2,3,4-tetrazol-5-yl)acetamido]pentanamido]acetyl}-2,3-dihydro-1H-indol-2-yl]formamido}-4-oxobutanoic acid methyl ester using method D with 2 eq. of LiOH H₂O. ¹H NMR (400 MHz, DMSO-d6) δ 0.83 (3H, m), 0.88 (3H, d, J=7 Hz), 1.12 (1H, m), 1.48 (1H, m), 1.78 (1H, m), 2.96-3.15 (2H, m), 3.32 (1H, m), 3.48-3.67 (2H, m), 3.93-4.12 (4H, m), 4.20-4.38 (3H, m), 5.08 (1H, m), 7.00 (1H, t, J=7 Hz), 7.12-7.34 (7H, m), 8.04 (1H, m), 8.30-8.48 (3H, m), MS (LC/MS) m/z observed 676.45, expected 676.28 [M+H].

Example C6

(S)-3-{[(2.5)-1-{2-[(2S,3S)-3-METHYL-2-[2-(2H-1,2,3,4-TETRAZOL-5-YL)ACETAMIDO]PENTANAMIDO]ACETYL}-2,3-DIHYDRO-1H-INDOL-2-YL]FORMAMIDO}-4-(METHYLCARBAMOYL)-4-OXOBUTANOIC ACID (S)-Methyl 3-(((benzyloxy)carbonyl)amino)-5-cyano-4-oxo-5-(triphenylphosphoranylidene)pentanoate (800 mg, 1.417 mmol, 1 eq., from Example C5) was ozonized in dry DCM (20 mL) at −78° C. for 1 hour. The blue-green reaction mixture was then purged with O₂ for 10 min and N₂ for 10 min at −78° C. The mixture became yellow. A solution of MeNH₂ 40% wt in water (165 mg, 2.13 mmol, 1.5 eq.) was added and the reaction was left at −78° C. for 1 hour and then allowed to warm up to RT. The solvent was then concentrated and the product was purified on normal phase using 0% to % ethyl acetate in hexanes as the eluent to give (S)-methyl 3-(((benzyloxy)carbonyl)amino)-5-(methylamino)-4,5-dioxopentanoate as a colorless glass (110.9 mg, 24%). MS (LC/MS) m/z observed 322.84, expected 323.12 [M+H]. Compound was confirmed using LC/MS and moved to next step as it was.

(S)-Methyl 3-(((benzyloxy)carbonyl)amino)-5-(methylamino)-4,5-dioxopentanoate (110.9 mg, 0.344 mmol) was dissolved in MeOH (20 mL) and treated with Pd/C (10% wt, 55 mg) under a hydrogen atmosphere for 6 hrs. The reaction mixture was then filtered over CELITE™ and the solids were washed with MeOH (3×15 mL). The filtrate and washings were concentrated to give (S)-methyl 3-amino-5-(methylamino)-4,5-dioxopentanoate (56.7 mg, 68%) as a yellow oil. MS (LC/MS) m/z observed 189.40, expected 189.09 [M+H]. Compound was confirmed using LC/MS and moved to next step as it was.

(S)-3-{[(2S)-1-{2-[2-Amino-(2S,3S)-3-methyl-pentanoylamino]acetyl}-2,3-dihydro-1H-indol-2-yl]formamido}-4-(methylcarbamoyl)-4-oxobutanoic methyl ester was prepared from (S)-methyl 3-amino-5-(methylamino)-4,5-dioxopentanoate and 1-2 using method A. MS (LC/MS) m/z observed 604.66, expected 604.30 [M+H]. Compound was confirmed using LC/MS and moved to next step as it was.

(S)-3-{[(2S)-1-{2-[(2S,3S)-3-Methyl-2-[2-(2H-1,2,3,4-tetrazol-5-yl)acetamido]pentanamido]acetyl}-2,3-dihydro-1H-indol-2-yl]formamido}-4-(methylcarbamoyl)-4-oxobutanoic methyl ester was prepared from (S)-3-{[(2S)-1-{2-[2-amino-(2S,3S)-3-methyl-pentanoylamino]acetyl}-2,3-dihydro-1H-indol-2-yl]formamido}-4-(methylcarbamoyl)-4-oxobutanoic methyl ester and 2-(2H-tetrazol-5-yl)acetic acid using method A but with DMF as solvent for the coupling reaction. MS (LC/MS) m/z observed 614.65, expected 614.27 [M+H]. Compound was confirmed using LC/MS and moved to next step as it was.

Title compound (S)-3-{[(2S)-1-{2-[(2S,3S)-3-methyl-2-[2-(2H-1,2,3,4-tetrazol-5-yl)acetamido]pentanamido]acetyl}-2,3-dihydro-1H-indol-2-yl]formamido}-4-(methylcarbamoyl)-4-oxobutanoic acid (C6) was prepared from (S)-3-{[(2S)-1-{2-[(2S,3S)-3-methyl-2-[2-(2H-1,2,3,4-tetrazol-5-yl)acetamido]pentanamido]acetyl}-2,3-dihydro-1H-indol-2-yl]formamido}-4-(methylcarbamoyl)-4-oxobutanoic methyl ester using method D with 2 eq. of LiOH H₂O.
¹H NMR (400 MHz, DMSO-d6) δ 0.83 (3H, m), 0.88 (3H, d, J=7 Hz), 1.12 (1H, m), 1.48 (1H, m), 1.78 (1H, m), 2.57 (3H, d, J=4 Hz), 2.96-3.15 (2H, m), 3.32 (1H, m), 3.48-3.67 (2H, m), 3.88-4.00 (2H, m), 4.10 (1H, m), 4.28-4.35 (2H, m), 5.08 (1H, m), 7.00 (1H, m), 7.12-7.34 (2H, m), 7.80 (1H, m), 8.04 (1H, m), 8.30-8.48 (2H, m), MS (LC/MS) m/z observed 600.03, expected 600.25 [M+H].

Example C7

(S)-5-CHLORO-3-{[1-{2-[(2S,3S)-3-METHYL-2-[2-(2H-1,2,3,4-TETRAZOL-5-YL)ACETAMIDO]PENTANAMIDO]ACETYL}-2,3-DIHYDRO-1H-INDOL-2-YL]FORMAMIDO}-(S)-4-OXOPENTANOIC ACID (S)-Ethyl 1-(2-((2S,3S)-2-(2-(2H-tetrazol-5-yl)acetamido)-3-methylpentanamido)acetyl)indoline-2-carboxylate was prepared from (S)-ethyl 1-(2-((2S,3S)-2-((tert-butoxycarbonyl)amino)-3-methylpentanamido)acetyl) indoline-2-carboxylate (from the synthesis of I-2) and 2-(2H-tetrazol-5-yl)acetic acid using method A but with DMF as solvent for the coupling reaction. MS (LC/MS) m/z observed 471.82, expected 472.23 [M+H]. Compound was confirmed using LC/MS and moved to next step as it was.

(S)-Ethyl 1-(2-((2S,3S)-2-(2-(2H-tetrazol-5-yl)acetamido)-3-methylpentanamido)acetyl)indoline-2-carboxylate (291.4 mg, 0.618 mmol) was dissolved in tert-butanol (20 mL) and a solution of LiOH H₂O (51.9 mg, 1.236 mmol, 2 eq.) in water (10 mL) was added. The reaction was left at RT for 2 hrs and then acidified to pH 3 with a HCl solution (aqueous, 1 N). The solvents were then concentrated and the residue was suspended in water (20 mL) and the white solid was filtered and washed with water (3×15 mL) to give (S)-1-(2-((2S,3S)-2-(2-(1H-tetrazol-5-yl)acetamido)-3-methylpentanamido)acetyl)indoline-2-carboxylic acid as a white solid (157 mg, 57%). MS (LC/MS) m/z observed 443.82, expected 444.20 [M+H]. Compound was confirmed using LC/MS and moved to next step as it was.

3-tert-Butoxycarbonylamino-5-chloro-4-oxo-pentanoic acid benzyl ester (25 mg, 0.0703 mmol) was treated with HCl in dioxane (2 mL, 4 N) for 30 minutes. The solvent was then evaporated and the residue was swapped with CH₂Cl₂ (2 mL) twice to give a white solid that was dissolved in CH₂Cl₂ (2 mL) and added HOBt (12.9 mg, 0.0844 mmol, 1.2 eq.), EDC (20.2 mg, 0.105 mmol, 1.5 eq) and (S)-1-(2-((2S,3S)-2-(2-(1H-tetrazol-5-yl)acetamido)-3-methylpentanamido)acetyl)indoline-2-carboxylic acid (31.1 mg, 0.0703 mmol, 1 eq.). DIPEA (0.049 mL, 0.281 mmol, 4 eq.) was then added and the reaction was left at RT for 45 minutes and quenched with AcOH (0.2 mL). The reaction went to 40% conversion. The solvent was evaporated and the product was purified by reverse phase C18 chromatography 10% to 60% methanol in water to give 5-chloro-3-(S)-[(1-{2-(S)-[3-(S)-methyl-2-(2-2H-tetrazol-5-yl-acetylamino)-pentanoylamino]-acetyl}-2,3-dihydro-1H-indole-2-(S)-carbonyl)-amino]-4-oxo-pentanoic acid benzyl ester as a white solid (15.5 mg, 32%). MS (LC/MS) m/z observed 680.87, expected 681.26 [M+H]. Compound was confirmed using LC/MS and moved to next step as it was.

Title compound (S)-5-chloro-3-{[1-{2-[(2S,3S)-3-methyl-2-[2-(2H-1,2,3,4-tetrazol-5-yl)acetamido]pentanamido]acetyl}-2,3-dihydro-1H-indol-2-yl]formamido}-(S)-4-oxopentanoic acid (C7) was prepared from 5-chloro-3-(S)-[(1-{2-(S)-[3-(S)-methyl-2-(2-2H-tetrazol-5-yl-acetylamino)-pentanoylamino]-acetyl}-2,3-dihydro-1H-indole-2-(S)-carbonyl)-amino]-4-oxo-pentanoic acid benzyl ester using method F but with a mixture of methanol/CH₂Cl₂ (1:1 (v/v) as the solvent. ¹H NMR (400 MHz, DMSO-d6) δ 0.77-0.93 (6H, m), 1.15 (1H, m), 1.48 (1H, m), 1.79 (1H, m), 2.73 (1H, m), 3.11 (1H, m), 3.20-3.45 (2H, m), 3.55-3.70 (2H, m), 3.97 (2H, s), 4.13 (1H, m), 4.32 (1H, m), 4.52 (1H, m), 4.72 (1H, m), 5.20 (1H, m), 7.02 (1H, m), 7.15-7.30 (2H, m), 8.05 (1H, m), 8.35-8.50 (2H, m), 8.90 (1H, m). MS (LC/MS) m/z observed 590.90, expected 591.21 [M+H].

Example C8

(S)-3-{[1-[(2S)-2-[(2S,3S)-2-(6-{5-[(3AS,4S,6AR)-2-OXO-HEXAHYDRO-1H-THIENO[3,4-D]IMIDAZOLIDIN-4-YL]PENTANAMIDO}HEXANAMIDO)-3-METHYLPENTANAMIDO]-4-CARBOXYBUTANOYL]-1H,2H,3H-PYRROLO[2,3-B]PYRIDIN-2-YL]FORMAMIDO}-5-CHLORO-(S)-4-OXOPENTANOIC ACID

I-10 (200 mg, 0.719 mmol) was dissolved in a mixture of allyl alcohol and HCl in dioxane (4 M) (20 mL, 1:1 (v/v)) and the reaction mixture was stirred at RT for 3 hours. The reaction mixture was then concentrated to dryness and swapped with allyl alcohol (2×25 mL). The solid obtained was dried well under reduced pressure to give (S)-allyl 2,3-dihydro-1H-pyrrolo[2,3-b]pyridine-2-carboxylate hydrochloride as a white solid (173 mg, quantitative). $^{1}$H NMR (400 MHz, DMSO-d6) 3.23 (1H, dd, J=5, 18 Hz), 3.55 (1H, dd, J=11, 18 Hz), 4.65 (2H, d, J=5 Hz), 4.86 (1H, dd, J=5, 11 Hz), 5.25 (1H, d, J=10 Hz), 5.36 (1H, d, J=17 Hz), 5.94 (1H, m), 6.80 (1H, t, J=7 Hz), 7.68-7.74 (2H, m), 9.29 (1H, bs), MS (LC/MS) m/z observed 204.98, expected 205.10 [M+H].

(S)-Allyl 1-((S)-5-(benzyloxy)-2-((tert-butoxycarbonyl)amino)-5-oxopentanoyl)-2,3-dihydro-1H-pyrrolo[2,3-b]pyridine-2-carboxylate was prepared from (S)-allyl 2,3-dihydro-1H-pyrrolo[2,3-b]pyridine-2-carboxylate hydrochloride and Boc-L-glutamic acid γ-benzyl ester (1.2 eq.) using method C in DMF. MS (LC/MS) m/z observed 523.95, expected 524.24 [M+H]. Compound was confirmed using LC/MS and moved to next step as it was.

(S)-Allyl 1-((S)-5-(benzyloxy)-2-((2S,3S)-2-((tert-butoxycarbonyl)amino)-3-methylpentanamido)-5-oxopentanoyl)-2,3-dihydro-1H-pyrrolo[2,3-b]pyridine-2-carboxylate was prepared from (S)-allyl 1-((S)-5-(benzyloxy)-2-((tert-butoxycarbonyl)amino)-5-oxopentanoyl)-2,3-dihydro-1H-pyrrolo[2,3-b]pyridine-2-carboxylate and Boc-L-Isoleucine using method A but without swapping with MeOH. MS (LC/MS) m/z observed 636.97, expected 637.32 [M+H]. Compound was confirmed using LC/MS and moved to next step as it was.

(S)-Allyl 1-((13S,16S)-16-(3-(benzyloxy)-3-oxopropyl)-13-((S)-sec-butyl)-2,2-dimethyl-4,11,14-trioxo-3-oxa-5,12,15-triazaheptadecan-17-oyl)-2,3-dihydro-1H-pyrrolo[2,3-b]pyridine-2-carboxylate was prepared from (S)-Allyl 1-((S)-5-(benzyloxy)-2-((2S,3S)-2-((tert-butoxycarbonyl)amino)-3-methylpentanamido)-5-oxopentanoyl)-2,3-dihydro-1H-pyrrolo[2,3-b]pyridine-2-carboxylate and Boc-6-aminohexanoic acid using method A in DMF as the solvent for the coupling reaction but without swapping with MeOH. MS (LC/MS) m/z observed 749.95, expected 750.41 [M+H]. Compound was confirmed using LC/MS and moved to next step as it was.

(S)-Allyl 1-((13S,16S)-16-(3-(benzyloxy)-3-oxopropyl)-13-((S)-sec-butyl)-2,2-dimethyl-4,11,14-trioxo-3-oxa-5,12,15-triazaheptadecan-17-oyl)-2,3-dihydro-1H-pyrrolo[2,3-b]pyridine-2-carboxylate (655 mg, 0.874 mmol, 1 equiv) and Pd(PPh$_3$)$_4$ (202 mg, 0.175, 0.2 equiv) were dissolved in CH$_2$Cl$_2$ (25 mL) under N$_2$. Morpholine (0.228 mL, 2.622 mmol, 3 equiv) was then added and the reaction was left at RT for 1 h. The solvent was then evaporated and the product was purified by column chromatography reverse phase using 10% to 60% methanol in water as the eluent to give pure (S)-1-((13S,16S)-16-(3-(benzyloxy)-3-oxopropyl)-13-((S)-sec-butyl)-2,2-dimethyl-4,11,14-trioxo-3-oxa-5,12,15-triazaheptadecan-17-oyl)-2,3-dihydro-1H-pyrrolo[2,3-b]pyridine-2-carboxylic acid as a yellow foam (216 mg, 35%). The remaining compound was contaminated with triphenylphosphine oxide. MS (LC/MS) m/z observed 709.78, expected 710.38 [M+H]. Compound was confirmed using LC/MS and moved to next step as it was.

Boc-L-aspartic acid beta-benzyl ester chloromethylketone (50 mg, 0.141 mmol, 2 eq.) was treated with HCl in dioxane (4 N, 4 mL) for 30 minutes. The solvent was then evaporated and the residue was swapped with CH$_2$Cl$_2$ (4 mL) twice to give a white solid that was dissolved in CH$_2$Cl$_2$ (2 mL) and added HOBt (12.9 mg, 0.0844 mmol, 1.2 eq.), EDC (20.2 mg, 0.105 mmol, 1.5 eq) and (S)-1-413S,16S)-16-(3-(benzyloxy)-3-oxopropyl)-13-((S)-sec-butyl)-2,2-dimethyl-4,11,14-trioxo-3-oxa-5,12,15-triazaheptadecan-17-oyl)-2,3-dihydro-1H-pyrrolo[2,3-b]pyridine-2-carboxylic acid (50 mg, 0.070 mmol, 1 eq.). DIPEA (0.049 mL, 0.281 mmol, 4 eq.) was then added and the reaction was left at RT for 45 minutes and quenched with AcOH (0.3 mL). The reaction went to 55% conversion. The solvent was evaporated and the product was purified by reverse phase C18 chromatography 10% to 85% methanol in water to give (13S,16S)-benzyl 16-((S)-2-(((R)-1-(benzyloxy)-5-chloro-1,4-dioxopentan-3-yl)carbamoyl)-2,3-dihydro-1H-pyrrolo[2,3-b]pyridine-1-carbonyl)-13-((S)-sec-butyl)-2,2-dimethyl-4,11,14-trioxo-3-oxa-5,12,15-triazanonadecan-19-oate as a colorless glass (22.4 mg, 33%). MS (LC/MS) m/z observed 946.77, expected 947.43 [M+H]. Compound was confirmed using LC/MS and moved to next step as it was.

(S)-4-((2S,3S)-2-(6-Aminohexanamido)-3-methylpentanamido)-5-((S)-2-(((R)-1-carboxy-4-chloro-3-oxobutan-2-yl)carbamoyl)-2,3-dihydro-1H-pyrrolo[2,3-b]pyridin-1-yl)-5-oxopentanoic acid hydrochloride was prepared from (13S,16S)-benzyl 16-((S)-2-(((R)-1-(benzyloxy)-5-chloro-1,4-dioxopentan-3-yl)carbamoyl)-2,3-dihydro-1H-pyrrolo[2,3-b]pyridine-1-carbonyl)-13-((S)-sec-butyl)-2,2-dimethyl-4,11,14-trioxo-3-oxa-5,12,15-triazanonadecan-19-oate using method F but with a mixture of methanol/CH$_2$Cl$_2$ (1:1 (v/v)) as the solvent, followed by method E but without any purification. MS (LC/MS) m/z observed 666.96, expected 667.29 [M+H]. Compound was confirmed using LC/MS and moved to next step as it was.

D-biotin (140 mg, 0.573 mmol, 10 eq.), HOBt (87.7 mg, 0.573 mmol, 10 eq.) and EDC (110 mg, 0.573 mmol, 10 eq.) were dissolved in DMF (3 mL) and DIEA (0.150 mL, 0.860 mmol, 15 eq.) was added. This mixture was stirred at rt for 5 minutes and was then added quickly a solution of (S)-4-((2S,3S)-2-(6-aminohexanamido)-3-methylpentanamido)-5-((S)-2-(((R)-1-carboxy-4-chloro-3-oxobutan-2-yl)carbamoyl)-2,3-dihydro-1H-pyrrolo[2,3-b]pyridin-1-yl)-5-oxopentanoic acid hydrochloride (40.3 mg, 0.0573 mmol, 1 eq.) in DMF (3 mL). The reaction mixture was left at RT for 30 minutes and then quenched with AcOH (0.5 mL). The solvent was evaporated and the product was purified by preparative HPLC reverse phase using a 10 minutes gradient from 43% to 55% methanol in water as the eluent to give (S)-3-{[1-[(2S)-2-[(2S,3S)-2-(6-{5-[(3aS,4S,6aR)-2-oxo-hexahydro-1H-thieno[3,4-d]imidazolidin-4-yl]pentanamido}hexanamido)-3-methylpentanamido]-4-carboxybutanoyl]-1H,2H,3H-pyrrolo[2,3-b]pyridin-2-yl]formamido}-5-chloro-(S)-4-oxopentanoic acid (C8) as a beige solid (8.7 mg, 17%). $^{1}$H NMR (400 MHz, DMSO-d6) δ 0.74-0.87 (6H, m), 1.10 (1H, m), 1.16-1.71 (16H, m), 1.85

(1H, m), 1.95-2.20 (5H, m), 2.25-2.45 (2H, m), 2.57 (1H, m), 2.82 (1H, dd, J=5, 12 Hz), 2.95-3.02 (2H, m), 3.09 (1H, m), 3.28-3.42 (3H, m), 3.56-3.62 (2H, m), 3.69 (1H, m), 4.11 (1H, m), 4.20 (1H, m), 4.30 (1H, m), 5.02 (0.5H, m), 5.32 (0.5H, m), 5.83 (1H, m), 6.35 (1H, s), 6.42 (1H, s), 7.05 (1H, m), 7.62-7.85 (3H, m), 8.12-8.25 (2H, m), 12.05-12.30 (2H, bs), MS (LC/MS) m/z observed 892.79, expected 893.36 [M+H].

Example D1

Human Granzyme B Enzymatic Inhibition Assay

An assay buffer (50 mM HEPES pH 7.5, 10% (w/v) sucrose, 0.2% (w/v) CHAPS and 5 mM DTT) was prepared for testing Granzyme B activity. As the assay buffer included DTT, it was added immediately prior to running the assay. A 2×GzmB enzyme mix was prepared (10 nM enzyme, Substrate: Ac-IEPD-AMC (150 uM, California Peptide Research Inc., Napa, Calif., USA), excitation/emission wavelengths were 380 nm and 460 nm respectively. Assay temperature was 30° C.) at 80 uL per well. Compounds were screened at one or two appropriate concentrations (to determine the percent inhibition at those concentrations) and/or a full dose response curve (typically 8 points, to identify the $IC_{50}$) in duplicate, triplicate, or higher replicates as needed. Ac-IEPD-AMC (Biovision Inc., Milpitas, Calif., USA) was used as a control and was also assessed in full dose response, in duplicate for each assay/plate. Background control wells consisted of 1× assay buffer, DMSO (5% v/v) and substrate. Positive control wells consisted of GzmB enzyme, DMSO (5% v/v) and substrate. Test compounds and control compounds were diluted in DMSO to 40× the final desired concentration. For example, a test compound may be tested in dose response, in serial, tripling dilution condition starting at 20 uM and ending at 9.1 nM (or any appropriate concentration range and dilution scheme). Control compounds were prepared similarly. Diluted compounds were prepared in a dilution plate and transferred to the reaction plate (96-well medium binding plate (Greiner Bio-One FLUOTRAC™)) to allow for the desired final concentrations when added to the enzyme with the assay buffer. After mixing, the reaction plate was placed on a shaker (at 300 RPM) for 5 min, followed by incubation (covered) on the bench, for 20 min. Plates were warmed to 30° C. for a total incubation time of 30 min. Plates so prepared were ready for addition of substrate and the subsequent reaction.

The substrate assay was prepared in advance at 2× the final desired concentration in DMSO. The appropriate substrate mix was added to each appropriate well on the reaction plate, and the plate was read immediately in the TECAN plate reader (TECAN INFINITE® M1000 Pro), set to the correct wavelength using 25 cycles, kinetic interval of 1 min, number of reads per well of 20 with shaking set to 1 s, double orbital, 2 mm amplitude. The gain was set to optimal (50%). When appropriate, percent inhibition data was collected and fitted to generate $IC_{50}$ data using GraphPad Prism 5 (GraphPad Software, La Jolla Calif. USA, www.graphpad.com) and its non-linear regression analysis tools or other equivalent tools.

Select compounds of Examples C1-C8 exhibited inhibitory activity against hGzmB. Each of the compounds of the invention identified in Table 1 exhibited Granzyme B inhibitory activity.

In certain embodiments, select compounds exhibited $IC_{50}$<50,000 nM. In other embodiments, select compounds exhibited $IC_{50}$<10,000 nM. In further embodiments, select compounds exhibited $IC_{50}$<1,000 nM. In still further embodiments, select compounds exhibited $IC_{50}$<100 nM. In certain embodiments, select compounds exhibited $IC_{50}$ from 10 nM to 100 nM, preferably from 1 nM to 10 nM, more preferably from 0.1 nM to 1 nM, and even more preferably from 0.01 nM to 0.1 nM.

Example D2

Human Granzyme B Enzymatic Inhibition Assay (384 Well)

A 2× assay buffer (50 mM HEPES pH 7.5, 0.2% (w/v) CHAPS, 5 mM DTT) was prepared for the enzyme to be tested. Since the assay buffer included DTT, it was added immediately prior to running the assay. A 2× enzyme mix (10 nM enzyme, Substrate: Ac-IEPD-AMC (50 uM, California Peptide Research Inc., Napa, Calif., USA), excitation/emission wavelengths were 380 nm and 460 nm respectively. Assay temperature was 30° C.) was prepared at 26 uL per well. Compounds were screened at one or two appropriate concentrations (to determine the percent inhibition at those concentrations) and/or a full dose response curve (typically 12 points, to identify the $IC_{50}$) in duplicate, triplicate, or higher replicates as needed. Ac-IEPD-AMC (Biovision Inc., Milpitas, Calif., USA) was used as a control and was also assessed in full dose response, in duplicate for each assay/plate. Background control wells consisted of 1× assay buffer and substrate. Positive control wells consisted of GzmB enzyme (no DMSO) and substrate. Test compounds and control compounds were diluted in 1× Assay Buffer to 15× the final desired concentration. For example, a test compound may be tested in dose response, in serial, tripling dilution condition starting at 20 uM and ending at 0.1 nM (or any appropriate concentration range and dilution scheme). The control compound was prepared similarly. Diluted compounds were prepared in a dilution plate and transferred to the reaction plate (384-well medium binding plate (Greiner Bio-One FLUOTRAC™)) to allow for the desired final concentrations when added to the enzyme with AB. After mixing, the reaction plate was placed on a shaker (at 300 RPM) for 5 min, followed by incubation (covered) on the bench, for 20 min. Plates were warmed to 30° C. for 5 mins for a total incubation time of 30 min. Plates so prepared were ready for addition of substrate and the subsequent reaction.

The assay substrate was prepared in advance at 2× the final desired concentration (50 uM) in assay buffer. 30 uL of the substrate mix was added to each appropriate well on the reaction plate, and the plate was read immediately in the TECAN plate reader (TECAN INFINITE® M1000 Pro), set to the correct wavelength using 15 cycles, kinetic interval of 1 min, number of reads per well of 20 with shaking set to 1 s, double orbital, 2 mm amplitude. The gain was set to 85 (with the z set at 23000 um). When appropriate, percent inhibition data was collected and fitted to generate $IC_{50}$ data using GraphPad Prism 5 (GraphPad Software, La Jolla Calif. USA, www.graphpad.com) and its non-linear regression analysis tools or other equivalent tools.

Select compounds of Examples C1-C8 exhibited inhibitory activity against hGzmB. Each of the compounds of the invention identified in Table 1 exhibited Granzyme B inhibitory activity.

In certain embodiments, select compounds exhibited $IC_{50}$<50,000 nM. In other embodiments, select compounds exhibited $IC_{50}$<10,000 nM. In further embodiments, select compounds exhibited $IC_{50}$<1,000 nM. In still further embodiments, select compounds exhibited IC$_{50}$<100 nM. In certain embodiments, select compounds exhibited IC$_{50}$ from 10 nM to 100 nM, preferably from 1 nM to 10 nM, more preferably from 0.1 nM to 1 nM, and even more preferably from 0.01 nM to 0.1 nM.

Example D3

Inhibition of Fibronectin Cleavage by GzmB

Black, 96 well high-binding assay plates (Griener Bio-one) were treated overnight at 4° C. with 40 uL of 8 ug/mL Hilyte Fluor 488 labeled Fibronectin (Cytoskeleton, Inc). After fibronectin coating, plates were washed 3 times in buffer (20 mM Tris-HCl, pH 7.4, 20 mM NaCl) then once with granzyme B assay buffer (50 mM HEPES, pH 7.5, 0.1% CHAPS). After washing, 50 uL of granzyme B assay buffer was added to each fibronectin-coated well. In a separate non-binding 96 well assay plate 5 uL of 20× inhibitor serial dilution stocks were added to 45 uL of 2.22×GzmB mix to establish inhibition (enzyme/inhibitor mixes were all prepared in granzyme B assay buffer and were incubated first at room temperature for 20 minutes, then at 30° C. for another 10 minutes). After incubation, 50 uL of this 2× enzyme/inhibitor mix was added to the corresponding coated well to initiate fibronectin cleavage (20 nM final granzyme B concentration, 8-point inhibitor dilution series starting at 50 uM). The assay was conducted at 30° C. in the TECAN plate reader (TECAN INFINITE® M1000 Pro), which was programmed to monitor the kinetic fluorescence polarization signal (filter set Ex/Em 470 nm/527 nm) with readings taken every minute, for 1 hour. Proteolytic activity was evaluated as the rate of fluorescence enhancement in the parallel emission over the linear range of the reaction. % Inhibition values were calculated from assay controls and the resulting date is shown in Table 2.

TABLE 2

Inhibition of Fibronectin Cleavage by GzmB Results.

| Compound | Percent Inhibition at Inhibitor Concentration | | |
|---|---|---|---|
| | 50 uM | 5.56 uM | 0.62 uM |
| C1 | 95% | 87% | 60% |

The embodiments of the invention in which an exclusive property or privilege is claimed are defined as follows:

1. A compound selected from the group consisting of
    (S)-3-{[1-{2-[(2S,3S)-2-(3-carboxypropanamido)-3-methylpentanamido]acetyl}-2,3-dihydro-1H-indol-2-yl]formamido}-4-oxobutanoic acid;
    3-{[(2S)-1-(2-acetamidoacetyl)-2,3-dihydro-1H-indol-2-yl]formamido}-4-oxobutanoic acid;
    (S)-3-{[(2S)-1-{2-[(2S,3S)-3-methyl-2-[2-(2H-1,2,3,4-tetrazol-5-yl)acetamido]pentanamido]acetyl}-1H,2H,3H-pyrrolo[2,3-b]pyridin-2-yl]formamido}-4-oxobutanoic acid;
    (S)-4-(benzylcarbamoyl)-3-{[(2S)-1-{2-[(2S,3S)-3-methyl-2-[2-(2H-1,2,3,4-tetrazol-5-yl)acetamido]pentanamido]acetyl}-2,3-dihydro-1H-indol-2-yl]formamido}-4-oxobutanoic acid;
    (S)-3-{[(2S)-1-{2-[(2S,3S)-3-methyl-2-[2-(2H-1,2,3,4-tetrazol-5-yl)acetamido]pentanamido]acetyl}-2,3-dihydro-1H-indol-2-yl]formamido}-4-(methylcarbamoyl)-4-oxobutanoic acid;
    (S)-5-chloro-3-{[1-{2-[(2S,3S)-3-methyl-2-[2-(2H-1,2,3,4-tetrazol-5-yl)acetamido]pentanamido]acetyl}-2,3-dihydro-1H-indol-2-yl]formamido}-(S)-4-oxopentanoic acid;
    (S)-3-{[1-[(2S)-2-[(2S,3S)-2-(6-{5-[(3aS,4S,6aR)-2-oxo-hexahydro-1H-thieno[3,4-d]imidazolidin-4-yl]pentanamido}hexanamido)-3-methylpentanamido]-4-carboxybutanoyl]-1H,2H,3H-pyrrolo[2,3-b]pyridin-2-yl]formamido}-5-chloro-(S)-4-oxopentanoic acid; and
    stereoisomers, tautomers, and pharmaceutically acceptable salts thereof.

2. A pharmaceutical composition, comprising a compound of claim 1 and a pharmaceutically acceptable carrier.

3. A method for inhibiting Granzyme B in a subject, comprising administering an effective amount of a compound of claim 1 to a subject in need thereof.

4. A method for treating a disease, disorder, or condition treatable by inhibiting Granzyme B, comprising administering a therapeutically effective amount of a compound of claim 1 to a subject in need thereof.

5. The method of claim 4, wherein the disease, disorder, or condition treatable by inhibiting Granzyme B is selected from treating dissection, aneurysm, and atherosclerosis.

6. The method of claim 4, wherein the condition treatable by inhibiting Granzyme B is a wound and administering the compound or composition promotes wound healing.

7. The method of claim 4, wherein administering the compound or composition comprises topical administration, oral administration, and administration by injection.

8. A method for treating cutaneous scleroderma, epidermolysis bullosa, radiation dermatitis, alopecia areata, or discoid lupus erythematosus, comprising administering a therapeutically effective amount of a compound of claim 1 to a subject in need thereof.

9. The method of claim 8, wherein administering the compound or composition comprises topical administration.

* * * * *